United States Patent [19]
Hadlaczky et al.

[11] Patent Number: 6,025,155
[45] Date of Patent: Feb. 15, 2000

[54] ARTIFICIAL CHROMOSOMES, USES THEREOF AND METHODS FOR PREPARING ARTIFICIAL CHROMOSOMES

[75] Inventors: Gyula Hadlaczky, Szamos, Hungary; Aladar A. Szalay, Highland, Calif.

[73] Assignees: Chromos Molecular Systems, Inc., Canada; The Biological Research Center of the Hungarian Academy of Sciences, Hungary

[21] Appl. No.: 08/695,191

[22] Filed: Aug. 7, 1996

Related U.S. Application Data

[63] Continuation-in-part of application No. 08/682,080, Jul. 15, 1996, which is a continuation-in-part of application No. 08/629,822, Apr. 10, 1996, abandoned.

[51] Int. Cl.[7] .............................. C12N 5/10; C12N 15/67; C12P 21/00
[52] U.S. Cl. .................. 435/69.1; 435/172.3; 435/320.1; 435/325
[58] Field of Search ............................. 435/172.3, 320.1, 435/69.1, 325

[56] References Cited

U.S. PATENT DOCUMENTS

| 4,441,972 | 4/1984 | Pohl | 435/172.2 |
|---|---|---|---|
| 4,476,004 | 10/1984 | Pohl | 435/285.2 |
| 4,518,584 | 5/1985 | Mark et al. | 424/85.2 |

(List continued on next page.)

FOREIGN PATENT DOCUMENTS

| 0240373 | 10/1987 | European Pat. Off. . |
|---|---|---|
| 0254315 A2 | 1/1988 | European Pat. Off. . |
| 0254315 A3 | 1/1988 | European Pat. Off. . |

(List continued on next page.)

OTHER PUBLICATIONS

Blennow, et al., Swedish survey on extra structurally abnormal chromosomes in 39 105 consecutive prenatal diagnoses: Prevalence and characterization by fluorescence in situ hybridization, *Prenatal Diagnosis*, 14:1019–1028, 1994.

Brondum–Nielsen and Mikkelsen, A 10–year survey, 1980–1990, of prenatally diagnosed small supernumerary marker chromosomes, identified by fish analysis. Outcome and follow–up of 14 cases diagnosed in a series of 12 699 prenatal samples, *Prenatal Diagnosis*, 15:615–619, 1995.

Gogel, et al., Mapping of replication initiation sites in the mouse ribosomal gene cluster, *Chromosoma*, 104:511–518, 1996.

Gonzalez and Sylvester, Complete sequence of the 43–kb human ribosomal DNA repeat: Analysis of the intergenic space, *Genomics*, 27:320–328, 1985.

(List continued on next page.)

*Primary Examiner*—Johnny F. Railey, II
*Attorney, Agent, or Firm*—Stephanie L. Seidman; Heller Ehrman White & McAuliffe

[57] ABSTRACT

Methods for preparing cell lines that contain artificial chromosomes, methods for preparation of artificial chromosomes, methods for purification of artificial chromosomes, methods for targeted insertion of heterologous DNA into artificial chromosomes, and methods for delivery of the chromosomes to selected cells and tissues are provided. Also provided are cell lines for use in the methods, and cell lines and chromosomes produced by the methods. In particular, satellite artificial chromosomes that, except for inserted heterologous DNA, are substantially composed of heterochromatin are provided. Methods for use of the artificial chromosomes, including for gene therapy, production of gene products and production of transgenic plants and animals are also provided.

37 Claims, 5 Drawing Sheets

U.S. PATENT DOCUMENTS

| | | | |
|---|---|---|---|
| 4,608,339 | 8/1986 | Yoakum et al. | 435/6 |
| 4,684,611 | 8/1987 | Schilperoort et al. | 435/172.3 |
| 4,686,186 | 8/1987 | Sugden | 435/243 |
| 4,784,737 | 11/1988 | Ray et al. | 435/172.1 |
| 4,806,476 | 2/1989 | Coons et al. | 435/172.2 |
| 4,873,191 | 10/1989 | Wagner et al. | 435/172.3 |
| 4,873,316 | 10/1989 | Meade et al. | 530/412 |
| 4,906,576 | 3/1990 | Marshall, III | 435/285.2 |
| 4,923,814 | 5/1990 | Marshall, III | 435/173.6 |
| 4,935,350 | 6/1990 | Patel et al. | 435/69.4 |
| 4,946,952 | 8/1990 | Kiefer | 536/25.41 |
| 4,955,378 | 9/1990 | Grasso | 607/53 |
| 4,970,162 | 11/1990 | Aksamit | 435/346 |
| 4,997,764 | 3/1991 | Dalla Favera | 435/70.21 |
| 5,019,034 | 5/1991 | Weaver et al. | 604/20 |
| 5,021,344 | 6/1991 | Armau et al. | 435/172.3 |
| 5,063,162 | 11/1991 | Kiefer | 435/270 |
| 5,118,620 | 6/1992 | Armau et al. | 435/172.3 |
| 5,144,019 | 9/1992 | Rossi et al. | 536/23.1 |
| 5,149,796 | 9/1992 | Rossi et al. | 536/23.2 |
| 5,162,215 | 11/1992 | Bosselman et al. | 435/172.3 |
| 5,215,914 | 6/1993 | Lo et al. | 435/252.1 |
| 5,223,263 | 6/1993 | Hostetler et al. | 424/450 |
| 5,240,840 | 8/1993 | Feinberg et al. | 435/172.3 |
| 5,240,846 | 8/1993 | Collins et al. | 435/371 |
| 5,260,191 | 11/1993 | Yang | 435/6 |
| 5,266,600 | 11/1993 | Tenmyo et al. | 514/691 |
| 5,272,262 | 12/1993 | Rossi et al. | 536/23.2 |
| 5,288,625 | 2/1994 | Hadlaczky | 435/172.2 |
| 5,292,658 | 3/1994 | Cormier et al. | 435/252.33 |
| 5,298,429 | 3/1994 | Evans et al. | 436/501 |
| 5,324,655 | 6/1994 | Kriegler et al. | 435/357 |
| 5,354,674 | 10/1994 | Hodgson | 435/172.3 |
| 5,358,866 | 10/1994 | Mullen et al. | 435/357 |
| 5,364,761 | 11/1994 | Ariga | 435/6 |
| 5,396,767 | 3/1995 | Suzuki | 60/298 |
| 5,409,810 | 4/1995 | Larder et al. | 435/5 |
| 5,413,914 | 5/1995 | Franzusoff | 435/23 |
| 5,418,155 | 5/1995 | Cormier et al. | 435/189 |
| 5,424,409 | 6/1995 | Ely et al. | 536/23.71 |
| 5,434,086 | 7/1995 | Collins et al. | 436/125 |
| 5,436,392 | 7/1995 | Thomas et al. | 800/205 |
| 5,449,604 | 9/1995 | Shellenberg et al. | 435/6 |
| 5,453,357 | 9/1995 | Hogan | 435/7.21 |
| 5,457,182 | 10/1995 | Weiderrecht et al. | 530/402 |
| 5,461,032 | 10/1995 | Krapcho et al. | 514/12 |
| 5,468,615 | 11/1995 | Chio et al. | 435/7.2 |
| 5,468,634 | 11/1995 | Liu | 435/348 |
| 5,470,708 | 11/1995 | Yang et al. | 435/6 |
| 5,470,730 | 11/1995 | Greenberg et al. | 435/172.3 |
| 5,482,928 | 1/1996 | De Bolle et al. | 514/12 |
| 5,489,520 | 2/1996 | Adams et al. | 435/172.3 |
| 5,491,075 | 2/1996 | Desnick et al. | 435/69.7 |
| 5,496,731 | 3/1996 | Xu et al. | 435/320.1 |
| 5,501,662 | 3/1996 | Hofmann | 604/20 |
| 5,501,967 | 3/1996 | Offringa et al. | 435/172.3 |
| 5,503,999 | 4/1996 | Jilka et al. | 435/172.3 |
| 5,721,118 | 2/1998 | Scheffler | 435/69.1 |

FOREIGN PATENT DOCUMENTS

| | | |
|---|---|---|
| 0254315 B1 | 1/1988 | European Pat. Off. |
| 0350052 | 1/1990 | European Pat. Off. |
| 0375406 A2 | 6/1990 | European Pat. Off. |
| 0473253 | 3/1992 | European Pat. Off. |
| 0532050 | 9/1992 | European Pat. Off. |
| 0838526 | 4/1998 | European Pat. Off. |
| 9100358 | 1/1991 | WIPO |
| 9217582 | 10/1992 | WIPO |
| 9419456 | 9/1994 | WIPO |
| 9423049 | 10/1994 | WIPO |
| 9424300 | 10/1994 | WIPO |
| 9500178 | 1/1995 | WIPO |
| 9507643 | 3/1995 | WIPO |
| 9514769 | 6/1995 | WIPO |
| 9520044 | 7/1995 | WIPO |
| 9529992 | 11/1995 | WIPO |
| 9532297 | 11/1995 | WIPO |
| 9640965 | 12/1996 | WIPO |
| 9707668 | 3/1997 | WIPO |
| 9707669 | 3/1997 | WIPO |
| 9716533 | 5/1997 | WIPO |
| 9808964 | 3/1998 | WIPO |

OTHER PUBLICATIONS

Gravholt and Friedrich, Molecular cyotgenetic study of supernumerary marker chromosomes in an unselected group of children, *Am. J. Med. Gen.*, 56:106–111, 1995.

Maden, et al., Clones of human ribosomal DNA containing the complete 18 S–rRNA and 28 S–rRNA genes, *J. Biochem.*, 246:519–527, 1987.

Manuelidis, Heterochromatic features of an 11–megabase transgene in brain cells, *Proc. Natl. Acad. Sci. USA*, 88:1049–1053, 1991.

Miesfeld and Arnheim, Indentification of the in vivo and in vitro origin of transcription in human rDNA, *Nucleic Acid Rsch.*, vol. 10, No. 13, 1982.

Yoon, et al., Mapping of replication initiation sites in human ribosomal DNA by Nascent–Strand abundance analysis, *Mol. Cell. Bio.*, pp. 2482–2489, May 1995.

Heller, et al., Mini–chromosomes derived from the human Y chromosome by telomere directed chromosome breakage, *Proc. Natl. Acad. Sci. USA*, 93:7125–7130, 1996.

Lamb and Gearhart, YAC transgenics and the study of genetics and human disease, *Cur. Opin. Gen. Dev.*, 5:342–348, 1995.

Beck von Bodman, et al, "Expression of multiple eukaryotic cells from a single promoter," in *Nicotina, Bio/Technology* 13:587–591, (1995).

Brazolot, et al., "Efficient transfection of chicken cells by lipofection and introduction of transfected blastoderm cells into the embryo", *Mol. Repro. Dev.* 30:304–312, (1993).

Brown, "Mammalian artificial chromosomes", *Curr. Opin. Genes Dev.* 2:479–486, (1992).

Dieken, et al., "Efficient modification of human chromosomal allesles using recombination–proficient chicken/human microcell hybrids", *Nature Genet.* 12:174–182, (1996).

Etches, et al., "Chimeric chickens and their use in manipulation of the chicken genome", *Poultry Sci.* 72:882–889, (1993).

Farr, et al. "Generation of a human X–derived minichromosome using telomere–associated chromosome fragmentation", *EMBO J.* 14:5444–5454, (1995).

Fraser, et al., "Efficient incorporation of transfected blastodermal cells into chimeric chicken embryos", *Int. J. Dev. Biol.* 37:381–385, (1993).

Green, et al., "Chromosomal region of the cystic fibrosis gene in yeast artificial chromosomes: A model for human genome mapping", *Science* 250:94–98, (1990).

Hadlaczky et al., "Centromere formation in mouse cells cotransformed with human DNA and a dominant marker gene", *Proc. Natl. Acad. Sci.USA* 88:8106–8110, (1991).

Hollo, et al., "Evidence for a megareplicon covering megabases of centrome segments", *Chromosome Research* 4:1–14, (1996).

Huxley, "Mammalian artificial chromosomes: a new tool for gene therapy", *Gene Therapy*, 1:7–12, (1994).

Jabs, et al., "Characterization of a cloned DNA sequence that is present at centromeres of all human autosomes and the X chromosome and shows polymorphic variation", *Proc. Natl. Acad.* 81:4884–4888, (1994).

Le Bolc'h, et al., "Cationic phosphonolipids as non viral vectors for DNA transfection", *Tetrahedron Lett.* 36:6681–6684, (1995).

Love, et al., "Transgenic birds by microinjection", *Bio/Technology* 12:60–63, (1994).

McLean, "Improved techniques for immortalizing animal cells", *Tibtech* 11:232–238, (1993).

Petitte, et al., "Production of somatic and germline chimeras in the chicken by transfer of early blastodermal cells", *Development* 108:185–189, (1990).

Praznovsky, et al., "De novo chromosome formation in rodent cells", *Proc. Natl. Acad. Sci. USA* 88:11042–11046, (1991).

Raimondi, et al., "X-ray mediated size reduction, molecular characterization and transfer in model systems of a human artrificial minichromosome", Abstrct from International Symposium on *Gene Therapy of Cancer, AIDS and Genetic Disorders*, Trieste (Italy) (Apr. 10–13, 1996).

Roth, et al., "Artifizielle chromosomen", *Natur Wissenschaften* 74:78–85, (1987). Abstract English.

Sang, et al., "Transgenic chickens—methods and potential application", *Tibtech* 12:415–420.

Smith, et al., "Amplification of large artificial chromosomes", *Proc. Natl. Acad. Sci. USA*, 87:8242–8246, (1990).

Waring, et al., "Nucleotide sequence repetition: A rapidly reassociating fraction of mouse DNA", *Science* 154:791–794, (1966).

Zang, et al., "Production of recombinant proteins in Chinese hamster ovary cells using a protein-free cell culture medium", *Bio/Technology* 13:389–392, (1995).

Albrecht, et al., "Cationic lipide mediated tranfer of c–abl and bcr antisense oligonucleotides to immature normal myeloid cells: Uptake, biological effects and modulation of gene expression*", *Ann Hematol* 72:73–79, (1996).

Carsience, et al., "Germline chimeric chickens from dispersed donor blastodermal cells and compromised recipient embryos", *Develop* 117:669–675, (1993).

Dhar, et al., "Transfer of Chinese Hamster Chromosome 1 to Mouse Cells and Regional Assignment of 7 Genes: A Combination of Gene Transfer and Microcell Fusion", *Somatic Cell and Molecular Genetics*, 10:(6)547–559, (1984).

Fowler, et al., "Donor lymphoid cells of th2 cytokine phenotype reduce lethal graft versus host disease and facilitats fully allogenetic cell transfers in sublethally irradiated mice", *Advances in Bone Marrow Purging and Processing: Fourth International Symposium*, p. 533–540, (1994).

Gaub, et al., "The chicken ovalbumin promoter is under negative control which is relieved by steriod hormones", *The EMBO Journal*, 6:(8)2313–2320, (1987).

Holmen, et al., "Efficient Lipid–mediated transfection of DNA into Primary Rat Hepatocytes", In Vitro *Cell, Dev. Biol.* 30:347–351, (1995).

Loefler, et al., "Gene Transfer into Primary and Established Mammalian Cell Lines with Lipopolymamine–Coated DNA", *Methods for Transforming Animal and Plant Cells* 217:599–618, (1993).

Killary, et al., "Microcell Fusion", *Methods in Enzymology*, 254:133–152, (1995).

Park, et al., "Modulation of Transcriptional Activity of the Chicken ovalbumin gene promoter in primary cultures of chicken oviduct cells: effects of putative regulatory elements in the 5'–flanking region", *Biochem and Mol Biol International* 36:(4)811–816, (1995).

Remy, et al., "Gene Transfer with a Series of Lipophilc DNA–Binding Molecules", *Bioconjugate Chem.* 5:647–654, (1994).

Sanford, et al., "General Protocol for Microcell–Mediated Chromosome Transfer", *Somatic Cell and Molecular Genetics*, 13:(3)279–284, (1987).

Sher, et al., "Role of T–Cell derived cytokines in the downregulation of immune responses in parasitic and retroviral infection", *Immunolical Reviews* (127)183–204, (?).

Strauss, "Transfection of Mammalian Cells via Lipofection", *Meth Biol* 54:307–327, (1996).

Szybalska, et al., "DNA–Mediated heritable transformation of biochemical trait", *Proc. N.A.S.* 48:2026–2034, (1962).

Teifel, et al., "New Lipid Mixture for Efficient Lipid–Mediated Transfection of BHK Cells", *Biotechniques* 19:79–82, (1995).

Tora, et al., "Cell–specific activity of a GGTCA half–palindromic oestrogen–responsive element in the chicken ovalbumin gene promoter", *The EMBO Journal* 7:(12)3771–3778, (1988).

Zhang, et al.,"T–Cell cytokine responses in human infection with Mycobacterium tuberculosis", *Infection and Immunity*, pp. 3231–3234, (1995).

Willard, Chromosome manipulation: a systematic approach toward understanding human chromosome structure and function, *Proc. Natl. Acad. Sci. USA* 93: 6847–6850 (1996).

Brown et al., Mammalian artificial chromosomes, *Current Opionion: Genetics and Devt.* 6: 281–288 (1996).

Chisari et al., A transgenic mouse model of the chronic hepatitis B surface antigen carrier state, *Science* 230: 1157–1160 (1985).

Henikoff et al., Position–effect variegation after 60 years, *Trends in Genetics* 6: 422–426 (1990).

Kappel et al., Regulating gene expression in transgenic animals, *Current Biology*, p. 548–553, (1992).

Kereso et al., De novo chromosome formations by large–scale amplification of the centromeric region of mouse chromosomes, *Chromosome Research* 4:226–239, (1996).

Klotman et al. Transgenic models of HIV–1, *Current Sci Ltd.* 9:313–324, (1995).

Larsson et al., Reduced β2–microglobulin mRNA levels in transgenic mice expressing a designed hammerhead ribozyme, *Nucleic Acids Research* 22:2242–2248, (1994).

Strojek et al. The use of transgenic animal techniques for livestock improvement, *Genetic Engineering: Principles and Methods* 10:221–246, (1988).

Dialog Abstract 007268905, citing: EP 0240 373 A1.

Dialog Abstract 007389041, citing: EP 0254 315.

Medline Abstract:07235130 93103732 [Molecular cytogenetic study of an extra small chromosome] Fu S; Fu H; Xiao H; Song X; Chen J; Gao C; Qiu H; Cheng Z I Chuan Hsueh Pao (China) 1992, 19 (4) p294–7.

Baker, et al., "Suppression of human colorectal carcinoma cell growth by wild–type p53", *Science* 249:912–915, (1990).

Biggin et al., "Buffer gradient gels and $^{35}$S label as an aid to rapid DNA sequence determination", *Proc. Natl. Acad. Sci. USA*,80:3963–3965, (1983).

Blackburn, et al., "The molecular structure of centromeres and telomeres", *Ann. Rev. Biochem.*, 53:163–194, (1984).

Blattner, et al., "Charon phages: Safer derivatives of bacteriophage lambda for DNA cloning", *Science 196*:16, (1977).

Bostock and Christie, "Analysis of the frequency of sister chromatid exchange in different regions of chromosomes of the Kangaroo rat," (*Dipodomys ordii*), *Chromosome 56*: 275–287, (1976).

Bostock and Clark, "Satellite DNA in large marker chromosomes of methotrexate–resistant mouse cells", *Cell 19*: 709–715, (1980).

Bower, "Constructing a fully defined human minichromosome: Cloning a centromere", *Proc. 4th Eur. Congress Biotechnol. 3*:571, (1987).

Brewer and Fangman, "The localization of replication origins on ARS plasmids", in *S. cerevisiae, Cell 51*:463–471, (1987).

Brisson and Hohn, "[27] Plant virus vectors: Cauliflower mosaic vectors", *Methods for Plant Molecular Biology*, Weissbach et al., eds., Academic Press, N.Y., Section VIII, pp. 437–446, (1988).

Bullock and Botchan, "Molecular events in the excision of SV40 DNA from the chromosomes of cultured mammalian cells," In: *Gene Amplification.*, Schimke RT, ed. Cold Spring Harbor, NY: Cold Spring Harbor Laboratory Press, pp. 215–224, (1982).

Burhans et al., "Identification of an origin of bidirectional DNA replication in mammalian chromosomes", *Cell 62*:955–965, (1990).

Burhans and Huberman, "DNA replication origins in animal cells—a question of context?" *Science 263*: 639–640, (1994).

Burke, et al., "Cloning of large segments of exogenous DNA into yeast by means of artificial chromosome vectors", *Science*, 236:806–812, (1987).

Carine, et al., "Chinese hamster cells with a minichromosome containing centromere region of human chromosome 1", *Somatic Cell Molec. Genet. 12*:479–491, (1986).

Carine, et al., "Molecular characterization of human minichromosomes with centromere from chromsome 1 in hamster–human hybrids", *Somatic Cell Molec. Genet. 15*(15):445–460, (1989).

Carrano and Wolff, "Distribution of sister chromatid exchanges in the euchromatin and heterochromatin of the Indian muntjac", *Chromosoma 53*:361–369, (1975).

Chalfie, et al., "Green fluorescent protein as a marker for gene expression", *Science 263*:802–804, (1994).

Chang, et al., "Ribozyme–mediated site–specific cleavage of the HIV–1 genome", *Clin. Biotech. 2*:23–31, (1990).

Chen, et al., "High–efficiency transformation of mammalian cells by plasmid DNA", *Mol. Cell. Biol. 7*:2745–2752, (1987).

Chen, et al., "Genetic mechanism of tumor suppression by the human p53 gene", *Science 250*:1576, (1990).

Chikashige et al., "Composite motifs and repeat symmetry in S. pombe centromeres: Direct analysis by integration of NotI restriction sites", *Cell 57*:739–751, (1989).

Church, "Replication of chromatin in mouse mammary epithelial cells grown in vitro," *Genetics 52*: 843–849, (1965).

Clarke, et al., "The structure and function of yeast centromeres", *Ann. Rev. Genet. 19*:29–56, (1985).

Colbère–Garapin, et al., "A new dominant hybrid selective marker for higher eukaryotic cells", *J. Mol. Biol. 150*:1–14, (1981).

Collins and Newlon, "Chromosomal DNA replication initiates at the same origin in meiosis and mitosis", *Mol Cell Biol 14*:3524–3534, (1994).

Cooper and Tyler–Smith, "The putative centromere–forming sequence of λCM8 is a single copy sequence and is not a component of most human centromeres", *Hum. Mol. Gen. 1*(9):753–754, (1992).

Couto, et al., "Inhibition of intracellular *histoplasma capsulatum* replication by murine macrophages that produce human defensin", *Infect. Immun. 62*:2375–2378, (1994).

Cram, et al., "Polyamine buffer for bivariate human flow cytogenetic analysis and sorting", *Methods in Cell Biology 33*:377–382, (1990).

Current state of the art, *Chromos Molecular Systems—News Release* (May 29, 1996) (available at http://www.chromos.com/contents.html).

Cutler, "Electroporation: Being developed to transform crops", *Ag Biotechnology News 7*:3, (Sep./Oct. 1990).

Davidson, et al., "Improved techniques for the induction of mammalian cell hybridisation by polyethylene glycol", *Somatic Cell. Genet. 2*:165–176, (1976).

Dean, et al., "Multiple mutations in highly conserved residues are found in mildly affected cyctic fibrosis patients", *Cell 61*:863–870, (1990).

DePamphilis, "Eukaryotic DNA replication: Anatomy of an origin", *Annu. Rev. Biochem. 62*:29–63, (1993).

Dunckley, et al., "Retroviral–mediated transfer of a dystrophin minigene into mdx mouse myoblasts in vitro", *FEBS Lett. 296*:128–34, (1992).

Erlich, et al., "Recent advances in the polymerase chain reaction", *Science 252*:1643–1651, (1991).

Fangman and Brewer, "A question of time: replication origins of eukaryotic chromosomes", *Cell 71*: 363–366, (1992).

Farrel, et al., "p53 is frequently mutated in Burkitt's lymphoma cell lines", *EMBO J. 10*:2879–2887, (1991).

Fátyol, et al., "Cloning and molecular characterization of a novel chromosome specific centromere sequence of Chinese hamster", *Nucl. Acids Res. 22*:3728–3736, (1994).

Fechheimer, et al., "Transfection of mammalian cells with plasmid DNA by scrape loading and sonication loading", *Proc. Natl. Acad. Sci. USA 84*:8463–8467, (1987).

Ford and Fried, "Large inverted duplications are associated with gene amplification", *Cell 45*:425–430, (1986).

Fournier, "A general high–efficiency procedure for production of microcell hybrids", *Proc. Natl. Acad. Sci.USA 78*:6349–6353, (1981).

French, et al., "Construction of a retroviral vector incorporating mouse VL30 retrotransposon–dervived, transcriptional regulatory sequences", *Anal. Biochem. 228*:354–355, (1995).

Frohman and Martin, "Cut, paste, and save: new Approaches to altering specific genes in mice", *Cell 56*:145–147, (1989).

Fromm, et al., "Expression of genes transferred into monocot and dicot plant cells by electroporation", *Proc. Natl. Acad. Sci.USA 82*:5824–5828, (1985).

Gillespie, et al., "Tissue–specific expression of human CD4 in transgenic mice", *Mol. Cell. Biol. 13*:2952–2958, (1993).

Gluzman, "SV40–transformed simian cells support the replication of early SV40 mutants", *Cell 23*:175–182, (1981).

Goodfellow, et al., "Techniques for mammalian genome transfer", in *Genome Analysis a Practical Approach*, K.E. Davies, ed., IRL Press, Oxford, Washington DC. pp. 1–17, (1989).

Graham and van der Eb, "A new technique for the assay of infectivity of human adenovirus 5 DNA", *Virology* 52:456–457, (1973).

Grierson, et al. *Plant Molecular Biology*, 2d Ed., Blackie, London, Ch. 7–9, (1988).

Gritz, et al., "Plasmid–encoded hygromycin B resistance: the sequence of hygromycin B phosphotransferase gene and its expression in *Escherichia coli* and *Saccharomyces cerevisiae*", *Gene* 25:179–188, (1983).

"Guide to Techniques in Mouse Development", *Methods in Enzymology* 25:803–932, (1993).

Gunning, et al., "A human β–actin expression vector system directs high–level accumulation of antisense transcripts", *Proc. Natl. Acad. Sci.USA* 84:4831–4835, (1987).

Haase, et al., "Transcription inhibits the replication of autonomously replicating plasmids in human cells", *Mol. Cell. Biol.* 14:2516–2524, (1994).

Hadlaczky, et al., "Protein depleted chromosomes", *Chromosoma* 81:537–555, (1981).

Hadlaczky, et al., "Direct evidence for the non–random localization of mammalian chromosomes in the interphase nucleus", *Exp. Cell Res.* 167:1–15, (1986).

Hadlaczky, et al., "Centromere proteins", *Chromosoma* 97:282–288, (1989).

Hadlaczky and Szalay, "Mammalian artificial chromosomes: Potential vectors for gene therapy", Abstract from International Symposium on *Gene Therapy of Cancer, AIDS and Genetic Disorders*, Trieste (Italy) (Apr. 10–13, 1996).

Hadlaczky and Szalay, "Mammalian artificial chromosomes: Introduction of novel genes into mammalian artificial chromosomes", Abstract from International Symposium on *Gene Therapy of Cancer, AIDS and Genetic Disorders*, Trieste (Italy) (Apr. 10–13, 1996).

Hadlaczky, et al., "Structure of isolated protein–depleted chromosomes of plants", *Chromosoma* 86:643–659, (1982).

Hadlaczky, "Structure of metaphase chromosomes of plants", *Internatl. Rev. Cytol.* 94:57–76, (1985).

Hall, et al., "Expression and regulation of *Escherichia coli* lacZ gene fusions in mammalian cells", *J. Mol. Appl. Gen.* 2:101–109, (1983).

Handeli, et al., "Mapping replication units in animal cells", *Cell* 57:909–920, (1989).

Hanna, et al., "Specific expression of the human CD4 gene in mature CD4$^+$ CD8$^-$ and immature CD4$^+$ CD8$^+$ T cells and in macrophages of transgenic mice", *Mol. Cell. Biol.* 14:1084–1094, (1994).

Harper, et al., "Localization of single copy DNA sequences on G–banded human chromosomes by in situ hybridization", *Chromosoma* 83:431–439, (1981).

Hassan, et al., "Replication and transcription sites are colocalized in human cells", *J. Cell. Sci.* 107:425–434, (1994).

Hilwig and Gropp, "Decondensation of constitutive heterochromatin in L cell chromosomes by a benzimidazole compound ("33258 Hoechst")", *Exp Cell Res* 81:474–477, (1973).

Hogan, et al., *Manipulating the Mouse Embryo: A Laboratory Manual*, Cold Spring Harbor Laboratory Press, Cold Spring Harbor, NY, pp. 253–289, see, especially pp. 255–264 and Appendix 3, (1994).

Holmquist and Comings, "Sister chromatid exchange and chromosome organisation based on a bromodeoxyuridine Giemsa–C–banding technique (TC–banding)", *Chromosoma* 52:245–259, (1975).

Hsu and Markvong, "Chromosomes and DNA in Mus: Terminal DNA synthetic sequences in three species", *Chromosoma* 51:311–322, (1975).

Huberman and Riggs, "On the mechanism of DNA replication in mammalian chromosomes", *J Mol Biol* 32:327–341, (1968).

Huberman, et al., "The in vivo replication origin of the yeast 2 μm plasmid", *Cell* 51:473–481, (1987).

Hyde, et al., "Correction of the ion transport defect in cystic fibrosis transgenic mice by gene therapy", *Nature* 362:250–255, (1993).

Hyrien, et al., "The multicopy appearance of large inverted duplication and the sequence at the inversion joint suggest a new model for gene amplification", *EMBO J* 7:407–417, (1988).

Ish–Horowitz, et al., "Rapid and efficient cosmid cloning", *Nucleic Acids Res.* 9:2989–2998, (1981).

Jacob, et al., "On the regulation of DNA replication in bacteria", *Cold Spring Harb Symp Quant Biol* 28:329–348, (1963).

Joy and Gopinathan, "Expression of microinjected foreign DNA in the silkworm", *Bombex mori, Current Science* 66:145–150, (1991).

Keown, et al., "Methods for introducing DNA into mammalian cells", *Meth. Enzymol.* 185:527–537, (1990).

Kerem, et al., "Identification of the cystic fibrosis gene: genetic analysis", *Science* 245:1073–1080, (1989).

Kitsberg, et al., "Replication structure of the human b–globin gene domain", *Nature* 366:588–590, (1993).

Korenberg, et al., "Human genome organization: Alu, Lines, and the molecular structure of metaphase chromosome bands", *Cell* 53:391–400, (1988).

Kornberg and Baker, *DNA Replication.* 2nd. ed., New York: W.H. Freeman and Co, p. 474, (1992).

Lambert, et al., "Functional complementation of ataxia–telangiectasia group D (AT–D) cells by microcell–mediated chromosome transfer and mapping of the AT–D locus to the region 11q22–23", *Proc. Natl. Acad. Sci. USA* 88:5907–59, (1991).

Lawrence, et al., "Sensitve, high–resolution chromatin and chromosome mapping in situ: Presence and orientation of two closely integrated copies of EBV in a lymphoma line", *Cell* 52:51–61, (1988).

Leder, et al., "EK2 derivatives of bacteriophage lambda useful in the cloning of DNA from higher organisms: The μgtWES system", *Science* 196:175–177), (1977).

Liu, et al., "The pro region of human neutrophil defensin contains a motif that is essential for normal subcellular sorting", *Blood* 85:1095–1103, (1995).

Locardi, et al., "Persistent infection of normal mice with human immunodeficiency virus", *J. Virol.* 66:1649–1654, (1992).

Looney, et al., "The dihydrofolate reductase amplicons in different methotrexate–resistant Chinese hamster cell lines share at least a 273–kilobase core sequence, but the amplicons in some cell lines are much larger and remarkably uniform in structure", *Mol. Cell Biol.* 8:5268–5279, (1988).

Lorenz, et al., "Isolation and expression of a cDNA encoding *Renilla reniformis* luciferase", *Proc. Natl. Acad. Sci. USA* 88:4438–4442 (1991).

Lorenz, et al., Expression of the *Renilla reniformis* luciferase gene in mammalian cells, *J. Biolum. Chemilum.* 11:31–37, (1996).

Ma, et al., "Sister chromatid fusion initiates amplification of the dihydrofolate reductase gene in Chinese hamster cells", *Genes Develop.* 7:605–620, (1993).

Ma, et al., "Organisation and genesis fo dihydrofolate reductase amplicons in the genome of a methotrexate–resistant Chinese hamster ovary cell line", *Mol. Cell Biol.* 8:2316–2327, (1988).

Madan, et al., "Fluorescence analysis of late DNA replication in mouse metaphase chromosomes using BUdR and 33258 Hoechst", *Exp. Cell Res.* 99:438–444, (1976).

Maniatis, et al., "The isolation of structural genes from libraries of eucaryotic DNA", *Cell* 15:687–701, (1978).

Mansour, et al., "Disruption of the proto–oncogene int–2 in mouse embryo–derived stem cells: a general strategy for targeting mutations to non–selectable genes", *Nature* 336:348–352, (1988).

Matthews, et al., "Purification and properties of *Renilla reniformis* luciferase", *Biochemistry* 16:85–91, (1977).

Maxwell, et al., "Regulated expression of a diptheria toxin A–chain gene transfected into human cells: possible strategy for inducing cancer cell suicide", *Cancer Res.* 46:4660–4664, (1986).

McGill, et al., "μCM8, a human sequence with putative centrometric function, does not map to the centromere but is present in one or two copies at 9qter", *Hum. Mol. Gen.* 1(9):749–751.

Meinkoth and Wahl, "Hybridization of nucleic acids immobilized on solid supports", *Anal. Biochem.* 138:267–284, (1984).

Meyne, et al., "Distribution of non–telomeric sites of the $(TTAGGG)_n$ telomeric sequence in vertebrate chromosomes", *Chromosoma* 99:3–10, (1990).

Miller, in *Experiments in Molecular Genetics*, Cold Spring Harbor Press, pp. 352–355, (1972).

Miller, "Is the centrometric heterochromatin of *Mus musculus* late replicating?" *Chromosoma* 55:165–170, (1976).

Miller and Rosman, "Improved retroviral vectors for gene transfer and expression", *Biotechniques* 7:980–990, (1989).

Mitani, et al., "Delivering therapeutic genes—matching approach and application", *Trends Biotech.* 11:162–166, (1993).

Morgan and French Anderson, "Human gene therapy", *Annu. Rev. Biochem.* 62:191–217, (1993).

Morgenstern, et al., "Advanced mammalian gene transfer: High titre retroviral vectors with multiple drug selection markers and a complementary helper–free packaging cell line", *Nucleic Acids Res.* 18:3587–3596, (1990).

Mulligan, "The basic science of gene therapy", *Science* 260:926–932, (1993).

Murray, et al., "Construction of artifical chromosomes in yeast", *Nature* 305:189–193, (1983).

Nabel, et al., "Site–specific gene expression in vivo by direct gene transfer into the arterial wall", *Science* 249:1285–1288, (1990).

Nikolaev, et al., "Microinjection of recombinant DNA into early embryos of the mulberry silkworm *Bombyx mori*," *Mol. Biol. (Moscow)* 23:1177–87, (1989).

O'Keefe, et al., "Dynamic organization of DNA replication in mammalian cell nuclei: Spatially and temporally defined replication of chromosome–specific a–satellite DNA sequences", *J. Cell Biol.* 116:1095–1110, (1992).

Osborne, et al., "A mutation in the second nucleotide binding fold of the cystic fibrosis gene", *Am. J. Hum. Genetics* 48:608–612, (1991).

Paszowski and Saul, "[28] Direct gene transfer to plants", *Methods for Plant Molecular Biology*, Weissbach et al., eds., Academic Press, N.Y., Section VIII, pp. 447–463, (1988).

Perry and Wolff, "A new Giemsa method for the differential staining of sister chromatids", *Nature* 251:156–158, (1974).

Pinkel, et al., "Cytogenetic analysis using quantitative, high–sensivity, fluorescence hybridization", *Proc. Natl. Acad. Sci. USA*, 83:2934–2938, (1986).

Prasher, et al., "Primary structure of the *Aequorea victoria* green–fluorescent protein", *Gene* 111:229–233, (1992).

Priest, "Cytogenetics", In *Medical Technology Series*. R.M. French, M. Eichman, B. Fiorella, and H.F. Weisberg, eds. (Lea and Febiger, Philadelphia) pp. 189–190, (1969).

Quastler, et al., "Cell population kinetics in the intestinal epithelium of the mouse", *Exp. Cell Res.* 17:420–438, (1959).

Report and recommendations of the panel to assess the NIH investment in research on gene therapy, Orkin and Motulsky, co–chairs (Dec. 7, 1995).

Richia and Lo, "Introduction of human DNA into mouse eggs by injection of dissected chromosome fragments", *Science* 245:175–177, (1989).

Riordan, et al., "Identification of the cystic fibrosis gene: cloning and characterization of complementary DNA", *Science* 245:1066–1072, (1989).

Rogers, et al., "[26] Gene transfer in plants: Production of transformed plants using Ti plasmid vectors", *Methods for Plant Molecular Biology*, Weissbach et al., eds., Academic Press, N.Y., Section VIII, pp. 423–436, (1988).

Rommens, et al., "Identification of the cystic fibrosis gene: chromosome walking and jumping", *Science* 245:1059–1065, (1989).

Rosenfeld, et al., "In vivo transfer of the human cystic fibrosis transmembrane conductance regulator gene to the airway epithelium", *Cell* 68:143–155, (1992).

Sambrook, et al., *Molecular Cloning: A Laboratory Manual, Volume 1*. 2d Ed., Cold Spring Harbor Laboratory Press,, Section 2.18, (1989).

Sanes, et al., "Use of a recombinant retrovirus to study post–implantation cell lineage in mouse embryos", *EMBO J.* 5(12):3133–3142, (1986).

Sanger, et al., "Cloning in single–stranded bacteriophage as an aid to rapid DNA sequencing", *J. Mol. Biol.* 143:161–178, (1980).

Saxon, et al., "Selective transfer of individual human chromosomes to recipient cells", *Mol. Cell. Biol.* 1:140–146, (1985).

Schedl, et al., "A method for the generation of YAC transgenic mice by pronuclear microinjection", *Nuc. Acids Res.* 21:4783–4787, (1993).

Scientists report a major step in ralizing the commercial potential of engineered artificial chromosomes in significant life sciences sectors, including gene therapy, *Chromos Molecular Systems—News Release* (May 29, 1996).

Selig, et al., "Regulation of mouse satellite DNA replication time", *EMBO J.* 7:419–426, (1988).

Smith, et al., "Distinctive chromosomal structures are formed very early in the amplification of CAD genes in Syrian hamster cells", *Cell* 63:1219–1227, (1990).

Solus, et al., "Characterization of single–copy probe from vicinity of centromere of human chromosome 1", *Somatic Cell Mol. Genet.* 14:381–391, (1988).

Sugden, et al., "A vector that replicates as a plasmid and can be efficiently selected in B–lymphoblast transformed by Epstein–Barr virus", *Mol. Cell. Biol.* 5:410–413, (1985).

Sumner, "Scanning electron microscopy of mammalian chromosomes from prophase to telophase", *Chromosoma* *100*:410–418, (1991).

Sumner, "A simple technique for demonstrating centromeric heterochromatin", *Cell Res.* 75:304–306, (1972).

Szybalsky, et al., "Genetic studies with human cell lines", *Natl. Cancer Inst. Monogr.* 7:75–89, (1982).

Tamura, et al., "Microinjection of DNA into early embryo of *Bombyx mori*", *Bio Ind.* 8:26–31, (1991), (Chemical Abstracts # 114(21)200502z).

Toledo, et al., "Co–amplified markers alternate in megabase long chromosomal inverted repeats and cluster independently in interphase nuclei at early steps of mammalian gene amplification", *EMBO J.* *11*:2665–2673, (1992).

Tonghua, et al., "Effects of antisense epidermal growth factor and its receptor retroviral expression vectors on cell growth of human pancreatic carcinoma cell line", *Chin. Med. J. (Beijing, Engl. Ed.)* *108*:653–659, (1995).

"Transfection of DNA into eukaryotic cells", *Current Protocols in Molecular Biology, vol. 1*, Wiley Inter–Science, Supplement 14, Unit 9.1.1–9.1.9, (1990).

Uchimiya, et al., "Transgenic plants", *J. Biotechnol.* *12*:1–20, (1989).

Vig and Richards, "Formation of primary constriction and heterochromatin in mouse does not require minor satellite DNA", *Exp. Cell Res. 201*:292–298, (1992).

Wang and Fedoroff, "Banding of human chromosomes treated with trypsin", *Nature 235*:52–54, (1972).

Weinberg, "Tumor suppressor genes", *Science 254*:1138–1146, (1991).

White, et al., "A frame–shift mutation in the cystic fibrosis gene", *Nature 344*:665–667, (1990).

"Why are MACs in vogue", *Chromos Molecular Systems—News Release* (May 29, 1996).

Wigler, et al., "DNA–mediated transfer of the adenine phosphoribosyltransferase locus into mammalian cells", *Proc. Natl. Acad. Sci. USA 76*:1373–1376, (1979).

Willard and Waye, "Hierarchical order in chromosome specific human alpha satellite DNA", *Trends Genet.* *3*:192–198, (1987).

Williams and Blattner, "Construction and characterization of the hybrid bacteriophage lambda charon vectors for DNA cloning", *J. Virol.* 29:555–575, (1979).

Wong, et al., "Sequence organisation and cytological localization of the minor satellite of mouse", *Nucl. Acids Res.* *16*:11645–11661, (1988).

Yamada, et al., "Multiple chromosomes carrying tumor suppressor activity for a uterine endometrical carcinoma cell line identified by microcell–mediated chromosome transfer", *Oncogene 5*:1141–1147, (1990).

Yates, et al., "Stable replication of plasmids derived from Epstein–Barr virus in various mammalian cells", *Nature 313*:812–815, (1985).

Yates, et al., "A cis–acting element from the Epstein–Barr viral genome that permits stable replication of recombinant plasmids in latently infected cells", *Proc. Natl. Acad. Sci. USA 81*:3806–3810, (1984).

Yeung, et al., "Human CD4–major histocompatibility complex class II (Dqw6) transgenic mice in an endogenous CD4/CD8–deficient background: reconstruction of phenotype and humano–restricted function." *J. Exp. Med.* *180*:1911–1920, (1994).

Yurov, "Identification and characterization of two distinct polymorphic α–satellite DNA sequences from centromeric regions of the chromosomes 13 and 21 (A2299)", *Cytogenet. Cell Genet. 51*:1114, (1989).

Yurov, "Collection of α–satellite DNA probes: Highly polymorphic markers for centromeric regions of all human chromosomes (A2298)", *Cytogenet. Cell Genet. 51*:1114, (1989).

Chick, et al., "Beta cell culture on synthetic capillaries: an artificial endocrine pancreas", Elliot P. Joslin Reserach Laboratory, Harvard Medical School, pp. 847–849, (1975).

Barnett et al., Telomere directed fragmentation of mammalian chromosomes, *Nucleic Acids Res. 21* (1): 27–36 (1993).

Cooke, Non–programmed and engineered chromosome breakage, *Cold Spring Harbor Monograph Series 29*: 219–245 (1995).

Farr, Mammalian telomeres and chromosome fragmentation, *Cell Devtl. Biol. 7*: 41–48 (1996).

Lin et al., Isolation and identification of a novel tandemly repeated DNA sequence in the centromeric region of human chromosome 8, *Chromosome 102*: 333–339 (1993).

Lee et al., Human gamma X satellite DNA: an X chromosome specific centromeric DNA sequence, *Chromosoma 104*: 103–112 (1995).

McGuigan et al., Replication of yeast DNA and novel chromosome formation in mouse cells, *Nuclic Acids Res.* 24(12): 2271–2280 (1996).

Raimondi, Gene targeting to the centromeric DNA of a human minichromosome. *Hum. Gene Ther. 7*: 1103–1109 (1996).

Taylor et al., Analysis of extrachromsomal structures containing human centromeric alphoid satellite DNA sequences in mouse cells, *Chromosoma 105*: 70–81 (1996).

Tyler–Smith et al., Mammalian chromosome structure, *Curr. Opin. Genet. Devt. 3*: 390–397 (1993).

Cross et al., The structure of subterminal repeated sequence present on many human chromosomes, *Nucleic Acids Res.* *18*(22): 6649–6657 (1990).

Raynal et al., Complete nucleotide sequence of mouse 18 SrRNA gene: comparison with other available homologs, *FEBS Lett. 167* (2): 263–367 (1984).

Torczynski et al., Cloning and sequencing of a human 18S ribosomal RNA gene, DNA 4 (4): 283–291 (1985).

ARTIFICIAL CHROMOSOMES, USES THEREOF AND METHODS FOR PREPARING ARTIFICIAL CHROMOSOMES

RELATED APPLICATIONS

This application is a continuation-in-part of U.S. application Ser. No. 08/682,080, filed Jul. 15, 1996 by GYULA HADLACZKY and ALADAR SZALAY, entitled ARTIFICIAL CHROMOSOMES, USES THEREOF AND METHODS FOR PREPARING ARTIFICIAL CHROMOSOMES, which is a continuation-in-part of U.S. application Ser. No. 08/629,822, filed Apr. 10, 1996, now abandoned, by GYULA HADLACZKY and ALADAR SZALAY, entitled ARTIFICIAL CHROMOSOMES, USES THEREOF AND METHODS FOR PREPARING ARTIFICIAL CHROMOSOMES.

This application is related to U.S. application Ser. No. 07/759,558, now U.S. Pat. No. 5,288,625 and to U.S. application Ser. No. 08/375,271, filed 1/19/95, now U.S. Pat. No. 5,712,134, which is a continuation of U.S. application Ser. No. 08/080,097, filed 6/23/93, now abandoned, which is a continuation of U.S. application Ser. No. 07/892,487, filed Jun. 3, 1992, now abandoned, which is a continuation of U.S. application Ser. No. 07/521,073, filed May 19, 1990, now abandoned.

The subject matter of each of U.S. application Serial Nos. 08/682,080, 08/629,822, 08/375,271, 08/080,097, 07/892,487, and 07/521,073, and U.S. Pat. No. 5,288,625 is incorporated in its entirety by reference thereto.

FIELD OF THE INVENTION

The present invention relates to methods for preparing cell lines that contain artificial chromosomes, methods for isolation of the artificial chromosomes, targeted insertion of heterologous DNA into the chromosomes, delivery of the chromosomes to selected cells and tissues and methods for isolation and large-scale production of the chromosomes. Also provided are cell lines for use in the methods, and cell lines and chromosomes produced by the methods. Further provided are cell-based methods for production of heterologous proteins, gene therapy methods and methods of generating transgenic animals all using artificial chromosomes.

BACKGROUND OF THE INVENTION

Several viral vectors, non-viral, and physical delivery systems for gene therapy and recombinant expression of heterologous nucleic acids have been developed [see, e.g., Mitani et al. (1993) *Trends Biotech.* 11:162–166]. The presently available systems, however, have numerous limitations, particularly where persistent, stable, or controlled gene expression is required. These limitations include: (1) size limitations because there is a limit, generally on order of about ten kilobases [kB], at most, to the size of the DNA insert [gene] that can be accepted by viral vectors, whereas a number of mammalian genes of possible therapeutic importance are well above this limit, especially if all control elements are included; (2) the inability to specifically target integration so that random integration occurs which carries a risk of disrupting vital genes or cancer suppressor genes; (3) the expression of randomly integrated therapeutic genes may be affected by the functional compartmentalization in the nucleus and are affected by chromatin-based position effects; (4) the copy number and consequently the expression of a given gene to be integrated into the genome cannot be controlled. Thus, improvements in gene delivery and stable expression systems are needed [see, e.g., Mulligan (1993) *Science* 260:926–932].

In addition, safe and effective vectors and gene therapy methods should have numerous features that are not assured by the presently available systems. For example, a safe vector should not contain DNA elements that can promote unwanted changes by recombination or mutation in the host genetic material, should not have the potential to initiate deleterious effects in cells, tissues, or organisms carrying the vector, and should not interfere with genomic functions. In addition, it would be advantageous for the vector to be non-integrative, or designed for site-specific integration. Also, the copy number of therapeutic gene(s) carried by the vector should be controlled and stable, the vector should secure the independent and controlled function of the introduced gene(s); and the vector should accept large (up to Mb size) inserts and ensure the functional stability of the insert.

The limitations of existing gene delivery technologies, however, argue for the development of alternative vector systems suitable for transferring large [up to Mb size or larger] genes and gene complexes together with regulatory elements that will provide a safe, controlled, and persistent expression of the therapeutic genetic material.

At the present time, none of the available vectors fulfill all these requirements. Most of these characteristics, however, are possessed by chromosomes. Thus, an artificial chromosome would be an ideal vector for gene therapy, as well as for stable, high-level, controlled production of gene products that require coordination of expression of numerous genes or that are encoded by large genes, and other uses. Artificial chromosomes for expression of heterologous genes in yeast are available, but construction of defined mammalian artificial chromosomes has not been achieved. Such construction has been hindered by the lack of an isolated, functional, mammalian centromere and uncertainty regarding the requisites for its production and stable replication. Unlike in yeast, there are no selectable genes in close proximity to a mammalian centromere, and the presence of long runs of highly repetitive pericentric heterochromatic DNA makes the isolation of a mammalian centromere using presently available methods, such as chromosome walking, virtually impossible. Other strategies are required for production of mammalian artificial chromosomes, and some have been developed. For example, U.S. Pat. No. 5,288,625 provides a cell line that contains an artificial chromosome, a minichromosome, that is about 20 to 30 megabases. Methods provided for isolation of these chromosomes, however, provide preparations of only about 10–20% purity. Thus, development of alternative artificial chromosomes and perfection of isolation and purification methods as well as development of more versatile chromosomes and further characterization of the minichromosomes is required to realize the potential of this technology.

Therefore, it is an object herein to provide mammalian artificial chromosomes and methods for introduction of foreign DNA into such chromosomes. It is also an object herein to provide methods of isolation and purification of the chromosomes. It is also an object herein to provide methods for introduction of the mammalian artificial chromosome into selected cells, and to provide the resulting cells, as well as transgenic animals, birds, fish and plants that contain the artificial chromosomes. It is also an object herein to provide methods for gene therapy and expression of gene products using artificial chromosomes. It is a further object herein to provide methods for constructing species-specific artificial chromosomes de novo. Another object herein is to provide methods to generate de novo mammalian artificial chromosomes.

SUMMARY OF THE INVENTION

Mammalian artificial chromosomes [MACs] are provided. Also provided are artificial chromosomes for other higher eukaryotic species, such as insects, birds, fowl and fish, produced using the MACS and methods provided herein. Methods for generating and isolating such chromosomes are provided. Methods using the MACs to construct artificial chromosomes from other species, such as insect, bird, fowl and fish species are also provided. The artificial chromosomes are fully functional stable chromosomes. Two types of artificial chromosomes are provided. One type, herein referred to as SATACs [satellite artificial chromosomes] are stable heterochromatic chromosomes, and the other type are minichromosomes based on amplification of euchromatin.

Artificial chromosomes provide an extra-genomic locus for targeted integration of megabase pair size DNA fragments that contain single or multiple genes, including multiple copies of a single gene operatively linked to one promoter or each copy or several copies linked to separate promoters. Thus, methods using the MACs to introduce the genes into cells, tissues, and animals, as well as species such as birds, fowl, fish and plants, are also provided. The artificial chromosomes with integrated heterologous DNA may be used in methods of gene therapy, in methods of production of gene products, particularly products that require expression of multigenic biosynthetic pathways, and also are intended for delivery into the nuclei of germlne cells, such as embryo-derived stem cells [ES cells], for production of transgenic animals, birds, fowl and fish. Transgenic plants, including monocots and dicots, are also contemplated herein.

Mammalian artificial chromosomes provide extra-genomic specific integration sites for introduction of genes encoding proteins of interest and permit megabase size DNA integration so that, for example, genes encoding an entire metabolic pathway or a very large gene, such as the cystic fibrosis [CF; ~250 kb] genomic DNA gene, several genes, such as multiple genes encoding a series of antigens for preparation of a multivalent vaccine, can be stably introduced into a cell. Vectors for targeted introduction of such genes, including the tumor suppressor genes, such as p53, the cystic fibrosis transmembrane regulator cDNA [CFTR], and the genes for anti-HIV ribozymes, such as an anti-HIV gag ribozyme gene, into the artificial chromosomes are also provided.

The chromosomes provided herein are generated by introducing heterologous DNA that includes DNA encoding one or multiple selectable marker(s) into cells, preferably a stable cell line, growing the cells under selective conditions, and identifying from among the resulting clones those that include chromosomes with more than one centromere and/or fragments thereof. The amplification that produces the additional centromere occurs in cells that contain chromosomes in which the heterologous DNA has integrated near the centromere in the pericentric region of the chromosome. The selected clonal cells are then used to generate artificial chromosomes.

In preferred embodiments, the DNA with the selectable marker that is introduced into cells to generate artificial chromosomes includes sequences that target it to the pericentric region of the chromosome. For example, vectors, such as pTEMPUD [provided herein], which includes such DNA specific for mouse satellite DNA, are provided. Also provided are derivatives of pTEMPUD containing human satellite DNA sequences that specifically target human chromosomes. Upon integration into existing chromosomes in the cells, these vectors can induce the amplification that results in generation of additional centromeres.

Artificial chromosomes are generated by culturing the cells with the multi-centric, typically dicentric, chromosomes under conditions whereby the chromosome breaks to form a minichromosome and formerly dicentric chromosome. Among the MACs provided herein are the SATACs, which are primarily made up of repeating units of short satellite DNA and are fully heterochromatic, so that without insertion of heterologous or foreign DNA, the chromosomes preferably contain no genetic information. They gcan thus be used as "safe" vectors for delivery of DNA to mammalian hosts because they do not contain any potentially harmful genes. The SATACs are generated, not from the minichromosome fragment as, for example, in U.S. Pat. No. 5,288,625, but from the fragment of the formerly dicentric chromosome. In addition, methods for generating euchromatic minichromosomes and the use thereof are also provided herein. Methods for generating one type of MAC, the minichromosome, previously described in U.S. Pat. No. 5,288,625, and the use thereof for expression of heterologous DNA are provided. Cell lines containing the minichromosome and the use thereof for cell fusion are also provided.

In one embodiment, a cell line containing the mammalian minichromosome is used as recipient cells for donor DNA encoding a selected gene or multiple genes. To facilitate integration of the donor DNA into the minichromosome, the recipient cell line preferably contains the minichromosome but does not also contain the formerly dicentric chromosome. This may be accomplished by methods disclosed herein such as cell fusion and selection of cells that contain a minichromosome and no formerly dicentric chromosome. The donor DNA is linked to a second selectable marker and is targeted to and integrated into the minichromosome. The resulting chromosome is transferred by cell fusion into an appropriate recipient cell line, such as a Chinese hamster cell line [CHO]. After large-scale production of the cells carrying the engineered chromosome, the chromosome is isolated. In particular, metaphase chromosomes are obtained, such as by addition of colchicine, and they are purified from the cell lysate. These chromosomes are used for cloning, sequencing and for delivery of heterologous DNA into cells.

Also provided are SATACs of various sizes that are formed by repeated culturing under selective conditions and subcloning of cells that contain chromosomes produced from the formerly dicentric chromosomes. The exemplified SATACs are based on repeating DNA units that are about 15 Mb [two ~7.5 Mb blocks]. The repeating DNA unit of SATACs formed from other species and other chromosomes may vary, but typically would be on the order of about 7 to about 20 Mb. The repeating DNA units are referred to herein as megareplicons, which in the exemplified SATACs contain tandem blocks of satellite DNA flanked by non-satellite DNA, including heterologous DNA and non-satellite DNA. Amplification produces an array of chromosome segments [each called an amplicon] that contain two inverted megareplicons bordered by heterologous ["foreign"] DNA. Repeated cell fusion, growth on selective medium and/or BrdU [5-bromodeoxyuridine] treatment or other treatment with other genome destabilizing reagent or agent, such as ionizing radiation, including X-rays, and subcloning results in cell lines that carry stable heterochromatic or partially heterochromatic chromosomes, including a 150–200 Mb "sausage" chromosome, a 500–1000 Mb gigachromosome, a stable 250–400 Mb megachromosome and various smaller stable chromosomes derived therefrom. These chromosomes are based on these repeating units and can include heterologous DNA that is expressed.

Thus, methods for producing MACs of both types (i.e., SATACS and minichromosomes) are provided. These methods are applicable to the production of artificial chromosomes containing centromeres derived from any higher eukaryotic cell, including mammals, birds, fowl, fish, insects and plants.

The resulting chromosomes can be purified by methods provided herein to provide vectors for introduction of heterologous DNA into selected cells for production of the gene product(s) encoded by the heterologous DNA, for production of transgenic animals, birds, fowl, fish and plants or for gene therapy.

In addition, methods and vectors for fragmenting the minichromosomes and SATACs are provided. Such methods and vectors can be used for in vivo generation of smaller stable artificial chromosomes. Vectors for chromosome fragmentation are used to produce an artificial chromosome that contains a megareplicon, a centromere and two telomeres and will be between about 7.5 Mb and about 60 Mb, preferably between about 10 Mb–15 Mb and 30–50 Mb. As exemplified herein, the preferred range is between about 7.5 Mb and 50 Mb. Such artificial chromosomes may also be produced by other methods.

Isolation of the 15 Mb [or 30 Mb amplicon containing two 15 Mb inverted repeats] or a 30 Mb or higher multimer, such as 60 Mb, thereof should provide a stable chromosomal vector that can be manipulated in vitro. Methods for reducing the size of the MACs to generate smaller stable self-replicating artificial chromosomes are also provided.

Methods and vectors for targeting heterologous DNA into the artificial chromosomes are also provided as are methods and vectors for fragmenting the chromosomes to produce smaller but stable and self- replicating artificial chromosomes.

The chromosomes are introduced into cells to produce stable transformed cell lines or cells, depending upon the source of the cells. Introduction is effected by any suitable method including, but not limited to electroporation, direct uptake, such as by calcium phosphate precipitation, uptake of isolated chromosomes by lipofection, by microcell fusion, by lipid-mediated carrier systems or other suitable method. The resulting cells can be used for production of proteins in the cells. The chromosomes can be isolated and used for gene delivery.

Methods for isolation of the chromosomes based on the DNA content of the chromosomes, which differs in MACs versus the authentic chromosomes, are provided.

These artificial chromosomes can be used in gene therapy, gene product production systems, production of humanized genetically transformed animal organs, production of transgenic plants and animals, including mammals, birds, fowl, fish, invertebrates, vertebrate, reptiles and insects, any organism or device that would employ chromosomal elements as information storage vehicles, and also for analysis and study of centromere function, for the production of artificial chromosome vectors that can be constructed in vitro, and for the preparation of species-specific artificial chromosomes. The artificial chromosomes can be introduced into cells using microinjection, cell fusion, microcell fusion, electroporation, electrofusion, projectile bombardment, calcium phosphate precipitation, lipid-mediated transfer systems and other such methods. Cells particularly suited for use with the artificial chromosomes include, but are not limited to plant cells, particularly tomato, arabidopsis, and others, insect cells, including silk worm cells, insect larvae, fish, reptiles, amphibians, arachnids, mammalian cells, avian cells, embryonic stem cells, haematopoietic stem cells, embryos and cells for use in methods of genetic therapy, such as lymphocytes that are used in methods of adoptive immunotherapy and nerve or neural cells. Thus methods of producing gene products and transgenic animals and plants are provided. Also provided are the resulting transgenic animals and plants.

Exemplary cell lines that contain these chromosomes are also provided.

Methods for preparing artificial chromosomes for particular species and for cloning centromeres are also provided. For example, two methods for generating artificial chromosomes for use in different species are provided. First, the methods herein may applied to different species. Second, means for generating species-specific artificial chromosomes and for cloning centromeres are provided. In particular, a method for cloning a centromere from an animal or plant by preparing a library of DNA fragments that contain the genome of the plant or animal, introducing each of the fragments into a mammalian satellite artificial chromosome [SATAC] that contains a centromere from a different species, generally a mammal, from the selected plant or animal, generally a non-mammal, and a selectable marker. The selected plant or animal is one in which the mammalian species centromere does not function. Each of the SATACs is introduced into the cells, which are grown under selective conditions, and cells with SATACs are identified. Such SATACS should contain a centromere encoded by the DNA from the library or should contain the necessary elements for stable replication in the selected species.

Also provided are libraries in which the relatively large fragments of DNA are contained on artificial chromosomes.

Transgenic animals, invertebrates and vertebrates, plants and insects, fish, reptiles, amphibians, arachnids, birds, fowl, and mammals are also provided. Of particular interest are transgenic animals that express genes that confer resistance or reduce susceptibility to disease. Since multiple genes can be introduced on a MAC, a series of genes encoding an antigen can be introduced, which upon expression will serve to immunize [in a manner similar to a multivalent vaccine] the host animal against the diseases for which exposure to the antigens provide immunity or some protection.

Also of interest are transgenic animals that serve as models of certain diseases and disorders for use in studying the disease and developing therapeutic treatments and cures thereof. Such animal models of disease express genes [typically carrying a disease-associated mutation], which are introduced into the animal on a MAC and which induce the disease or disorder in the animal. Similarly, MACs carrying genes encoding antisense RNA may be introduced into animal cells to generate conditional "knock-out" transgenic animals. In such animals, expression of the antisense RNA results in decreased or complete elimination of the products of genes corresponding to the antisense RNA. Of further interest are transgenic mammals that harbor MAC-carried genes encoding therapeutic proteins that are expressed in the animal's milk. Transgenic animals for use in xenotransplantation, which express MAC-carried genes that serve to humanize the animal's organs, are also of interest. Genes that might be used in humanizing animal organs include those encoding human surface antigens.

Methods for cloning centromeres, such as mammalian centromeres, are also provided. In particular, in one embodiment, a library composed of fragments of SATACs are cloned into YACs [yeast artificial chromosomes] that include a detectable marker, such as DNA encoding tyrosinase, and then introduced into mammalian cells, such as albino mouse embryos. Mice produced from embryos containing such YACs that include a centromere that functions in mammals will express the detectable marker. Thus, if mice are produced from albino mouse embryos into which a functional mammalian centromere was introduced, the mice will be pigmented or have regions of pigmentation.

DETAILED DESCRIPTION OF PREFERRED EMBODIMENTS

Definitions

Figure 1:
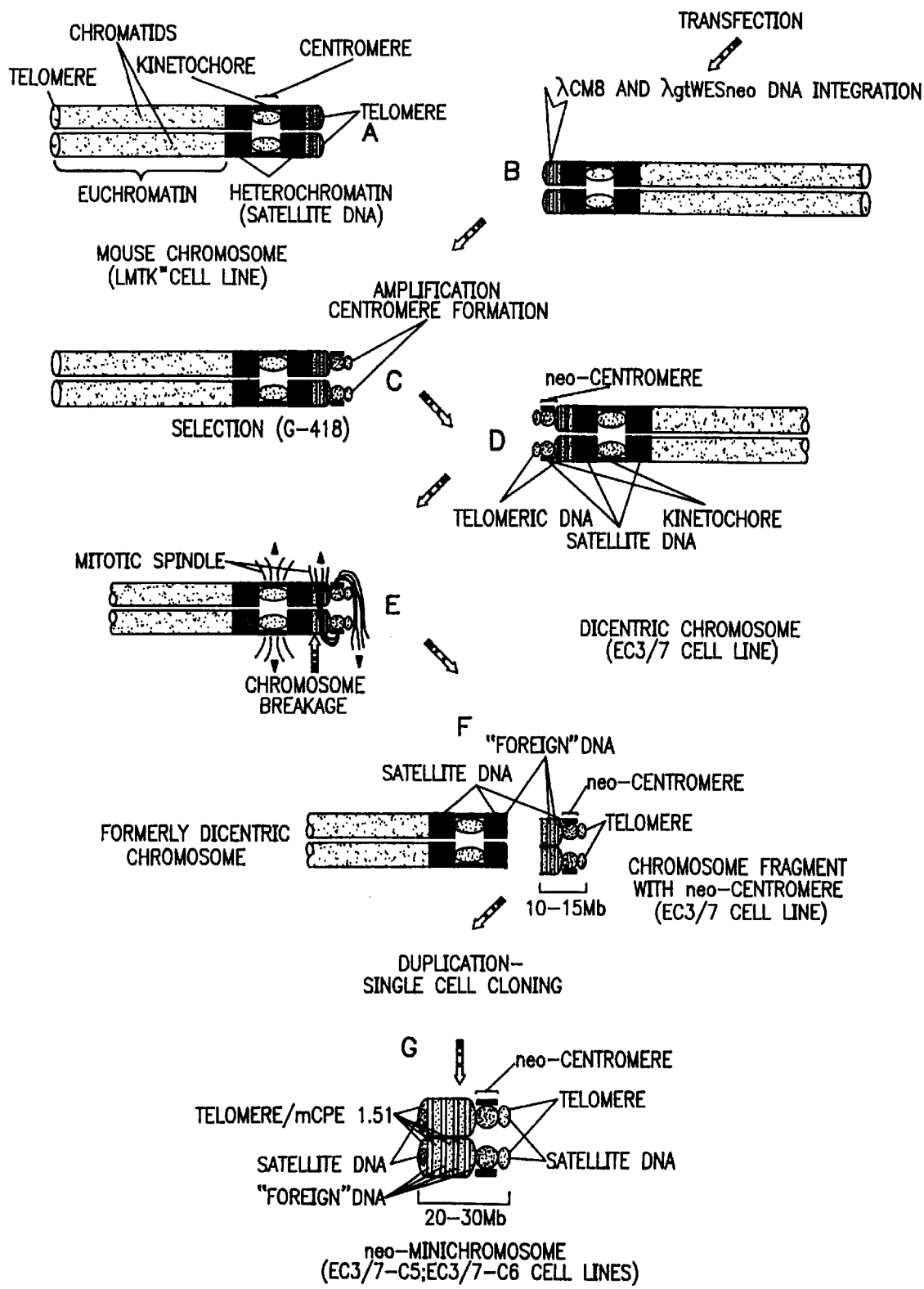
FIG. 1 is a schematic drawing depicting formation of the MMCneo [the minichromosome] chromosome. A–G represents the successive events consistent with observed data that would lead to the formation and stabilization of the minichromosome.

Unless defined otherwise, all technical and scientific terms used herein have the same meaning as is commonly understood by one of skill in the art to which this invention belongs. All patents and publications referred to herein are incorporated by reference.

As used herein, a mammalian artificial chromosome [MAC] is a piece of DNA that can stably replicate and segregate alongside endogenous chromosomes. It has the capacity to accommodate and express heterologous genes inserted therein. It is referred to as a mammalian artificial chromosome because it includes an active mammalian centromere(s). Plant artificial chromosomes, insect artificial chromosomes and avian artificial chromosomes refer to chromosomes that include plant and insect centromeres, respectively. A human artificial chromosome [HAC] refers to chromosomes that include human centromeres, BUGACs refer to insect artificial chromosomes, and AVACs refer to avian artificial chromosomes.

As used herein, stable maintenance of chromosomes occurs when at least about 85%, preferably 90%, more preferably 95%, of the cells retain the chromosome. Stability is measured in the presence of a selective agent. Preferably these chromosomes are also maintained in the absence of a selective agent. Stable chromosomes also retain their structure during cell culturing, suffering neither intrachromosomal nor interchromosomal rearrangements.

As used herein, growth under selective conditions means growth of a cell under conditions that require expression of a selectable marker for survival.

As used herein, euchromatin and heterochromatin have their recognized meanings, euchromatin refers to DNA that contains genes, and heterochromatin refers to chromatin that has been thought to be inactive. Highly repetitive DNA sequences [satellite DNA], at least with respect to mammalian cells, are usually located in regions of centromeric heterochromatin [pericentric heterochromatin]. Constitutive heterochromatin refers to heterochromatin that contains the highly repetitive DNA which is constitutively condensed and genetically inactive.

As used herein, BrdU refers to 5-bromodeoxyuridine, which during replication is inserted in place of thymidine. BrdU is used as a mutagen; it also inhibits condensation of metaphase chromosomes during cell division.

As used herein, a dicentric chromosome is a chromosome that contains two centromeres. A multicentric chromosome contains more than two centromeres.

As used herein, a formerly dicentric chromosome is a chromosome that is produced when a dicentric chromosome fragments and acquires new telomeres so that two chromosomes, each having one of the centromeres, are produced. Each of the fragments are replicable chromosomes. If one of the chromosomes undergoes amplification of euchromatic DNA to produce a full functionally chromosome that contains the newly introduced heterologous DNA and primarily [at least more than 50%] euchromatin, it is a minichromosome. The remaining chromosome is a formerly dicentric chromosome. If one of the chromosomes undergoes amplification, whereby heterochromatin [satellite DNA] is amplified and a euchromatic portion [or arm] remains, it is referred to as a sausage chromosome. A chromosome that is substantially all heterochromatin, except for portions of heterologous DNA, is called a SATAC. Such chromosomes [SATACs] can be produced from sausage chromosomes by culturing the cell containing the sausage chromosome under conditions, such as BrdU treatment and/or growth under selective conditions, that destabilize the chromosome so that a satellite artificial chromosomes [SATAC] is produced. For purposes herein, it is understood that SATACs may not necessarily be produced in multiple steps, but may appear after the initial introduction of the heterologous DNA and growth under selective conditions, or they may appear after several cycles of growth under selective conditions and BrdU treatment.

As used herein an amplicon is a repeated DNA amplification unit that contains a set of inverted repeats of the megareplicon. A megareplicon represents a higher order replication unit. For example, with reference to the SATACs, the megareplicon contains a set of tandem DNA blocks each containing satellite DNA flanked by non-satellite DNA. Contained within the megareplicon is a primary replication site, referred to as the megareplicator, which may be involved in organizing and facilitating replication of the pericentric heterochromatin and possibly the centromeres. Within the megareplicon there may be smaller [e.g., 50- 300 kb in some mammalian cells] secondary replicons. In the exemplified SATACS, the megareplicon is defined by two tandem ~7.5 Mb DNA blocks [see, e.g., FIG. 3]. Within each artificial chromosome [AC] or among a population thereof, each amplicon has the same gross structure but may contain sequence variations. Such variations will arise as a result of movement of mobile genetic elements, deletions or insertions or mutations that arise, particularly in culture. Such variation does not affect the use of the ACs or their overall structure as described herein.

As used herein, the minichromosome refers to a chromosome derived from a multicentric, typically dicentric, chromosome [see, e.g., FIG. 1 ] that contains more euchromatic than heterochromatic DNA.

As used herein, a megachromosome refers to a chromosome that, except for introduced heterologous DNA, is substantially composed of heterochromatin. Megachromosomes are made of an array of repeated amplicons that contain two inverted megareplicons bordered by introduced heterologous DNA [see, e.g., FIG. 3 for a schematic drawing of a megachromosome]. For purposes herein, a megachromosome is about 50 to 400 Mb, generally about 250–400 Mb. Shorter variants are also referred to as truncated megachromosomes [about 90 to 120 or 150 Mb], dwarf megachromosomes [~150–200 Mb] and cell lines, and a micromegachromosome [~60–90 Mb]. For purposes herein, the term megachromosome refers to the overall repeated structure based on an array of repeated chromosomal segments [amplicons] that contain two inverted megareplicons bordered by any inserted heterologous DNA. The size will be specified.

As used herein, genetic therapy involves the transfer or insertion of heterologous DNA into certain cells, target cells, to produce specific gene products that are involved in correcting or modulating disease. The DNA is introduced into the selected target cells in a manner such that the heterologous DNA is expressed and a product encoded thereby is produced. Alternatively, the heterologous DNA may in some manner mediate expression of DNA that encodes the therapeutic product. It may encode a product, such as a peptide or RNA, that in some manner mediates, directly or indirectly, expression of a therapeutic product. Genetic therapy may also be used to introduce therapeutic compounds, such as TNF, that are not normally produced in the host or that are not produced in therapeutically effective amounts or at a therapeutically useful time. Expression of the heterologous DNA by the target cells within an organism afflicted with the disease thereby enables modulation of the disease. The heterologous DNA encoding the therapeutic product may be modified prior to introduction into the cells of the afflicted host in order to enhance or otherwise alter the product or expression thereof.

As used herein, heterologous or foreign DNA and RNA are used interchangeably and refer to DNA or RNA that does not occur naturally as part of the genome in which it is present or which is found in a location or locations in the genome that differ from that in which it occurs in nature. It is DNA or RNA that is not endogenous to the cell and has been exogenously introduced into the cell. Examples of heterologous DNA include, but are not limited to, DNA that encodes a gene product or gene product(s) of interest, introduced for purposes of gene therapy or for production of an encoded protein. Other examples of heterologous DNA include, but are not limited to, DNA that encodes traceable marker proteins, such as a protein that confers drug resistance, DNA that encodes therapeutically effective substances, such as anti-cancer agents, enzymes and hormones, and DNA that encodes other types of proteins, such as antibodies. Antibodies that are encoded by heterologous DNA may be secreted or expressed on the surface of the cell in which the heterologous DNA has been introduced.

As used herein, a therapeutically effective product is a product that is encoded by heterologous DNA that, upon introduction of the DNA into a host, a product is expressed that effectively ameliorates or eliminates the symptoms, manifestations of an inherited or acquired disease or that cures said disease.

As used herein, transgenic plants refer to plants in which heterologous or foreign DNA is expressed or in which the expression of a gene naturally present in the plant has been altered.

As used herein, operative linkage of heterologous DNA to regulatory and effector sequences of nucleotides, such as promoters, enhancers, transcriptional and translational stop sites, and other signal sequences refers to the relationship between such DNA and such sequences of nucleotides. For example, operative linkage of heterologous DNA to a promoter refers to the physical relationship between the DNA and the promoter such that the transcription of such DNA is initiated from the promoter by an RNA polymerase that specifically recognizes, binds to and transcribes the DNA in reading frame.

As used herein, isolated, substantially pure DNA refers to DNA fragments purified according to standard techniques employed by those skilled in the art, such as that found in Maniatis et al. [(1982) *Molecular Cloning: A Laboratory Manual,* Cold Spring Harbor Laboratory Press, Cold Spring Harbor, N.Y.].

As used herein, expression refers to the process by which nucleic acid is transcribed into mRNA and translated into peptides, polypeptides, or proteins. If the nucleic acid is derived from genomic DNA, expression may, if an appropriate eukaryotic host cell or organism is selected, include splicing of the mRNA.

As used herein, vector or plasmid refers to discrete elements that are used to introduce heterologous DNA into cells for either expression of the heterologous DNA or for replication of the cloned heterologous DNA. Selection and use of such vectors and plasmids are well within the level of skill of the art.

As used herein, transformation/transfection refers to the process by which DNA or RNA is introduced into cells. Transfection refers to the taking up of exogenous nucleic acid, e.g., an expression vector, by a host cell whether or not any coding sequences are in fact expressed. Numerous methods of transfection are known to the ordinarily skilled artisan, for example, by direct uptake using calcium phosphate [CaPO4; see, e.g., Wigler et al. (1979) *Proc. Natl. Acad. Sci. U.S.A.* 76:1373–1376], polyethylene glycol [PEG]-mediated DNA uptake, electroporation, lipofection [see, e.g., Strauss (1996) *Meth. Mol. Biol.* 54:307–327], microcell fusion [see, EXAMPLES, see, also Lambert (1991) *Proc. Natl. Acad. Sci. U.S.A.* 88:5907–5911; U.S. Pat. No. 5,396,767, Sawford et al. (1987) *Somatic Cell Mol.*

Genet. 13:279–284; Dhar et al. (1984) Somatic Cell Mol. Genet. 10:547–559; and McNeill-Killary et al. (1995) Meth. Enzymol. 254:133–152], lipid-mediated carrier systems [see, e.g., Teifel et al. (1995) Biotechnigues 19:79–80; Albrecht et al. (1996) Ann. Hematol. 72:73–79; Holmen et al. (1995) In Vitro Cell Dev. Biol. Anim. 31:347–351; REmy et al. (1994) Bioconjug. Chem. 5:647–654; Le Bolch et al. (1995) Tetrahedron Lett. 36:6681–6684; Loeffler et al. (1993) Meth. Enzymol. 217:599–618] or other suitable method. Successful transfection is generally recognized by detection of the presence of the heterologous nucleic acid within the transfected cell, such as any indication of the operation of a vector within the host cell. Transformation means introducing DNA into an organism so that the DNA is replicable, either as an extrachromosomal element or by chromosomal integration.

As used herein, injected refers to the microinjection [use of a small syringe] of DNA into a cell.

As used herein, substantially homologous DNA refers to DNA that includes a sequence of nucleotides that is sufficiently similar to another such sequence to form stable hybrids under specified conditions.

It is well known to those of skill in this art that nucleic acid fragments with different sequences may, under the same conditions, hybridize detectably to the same "target" nucleic acid. Two nucleic acid fragments hybridize detectably, under stringent conditions over a sufficiently long hybridization period, because one fragment contains a segment of at least about 14 nucleotides in a sequence which is complementary [or nearly complementary] to the sequence of at least one segment in the other nucleic acid fragment. If the time during which hybridization is allowed to occur is held constant, at a value during which, under preselected stringency conditions, two nucleic acid fragments with exactly complementary base-pairing segments hybridize detectably to each other, departures from exact complementarity can be introduced into the base-pairing segments, and base-pairing will nonetheless occur to an extent sufficient to make hybridization detectable. As the departure from complementarity between the base-pairing segments of two nucleic acids becomes larger, and as conditions of the hybridization become more stringent, the probability decreases that the two segments will hybridize detectably to each other.

Two single-stranded nucleic acid segments have "substantially the same sequence," within the meaning of the present specification, if (a) both form a base-paired duplex with the same segment, and (b) the melting temperatures of said two duplexes in a solution of 0.5×SSPE differ by less than 10° C. If the segments being compared have the same number of bases, then to have "substantially the same sequence", they will typically differ in their sequences at fewer than 1 base in 10. Methods for determining melting temperatures of nucleic acid duplexes are well known [see, e.g., Meinkoth and Wahl (1984) Anal. Biochem. 138:267–284 and references cited therein].

As used herein, a nucleic acid probe is a DNA or RNA fragment that includes a sufficient number of nucleotides to specifically hybridize to DNA or RNA that includes identical or closely related sequences of nucleotides. A probe may contain any number of nucleotides, from as few as about 10 and as many as hundreds of thousands of nucleotides. The conditions and protocols for such hybridization reactions are well known to those of skill in the art as are the effects of probe size, temperature, degree of mismatch, salt concentration and other parameters on the hybridization reaction. For example, the lower the temperature and higher the salt concentration at which the hybridization reaction is carried out, the greater the degree of mismatch that may be present in the hybrid molecules.

To be used as a hybridization probe, the nucleic acid is generally rendered detectable by labelling it with a detectable moiety or label, such as $^{32}P$, $^{3}H$ and $^{14}C$, or by other means, including chemical labelling, such as by nick-translation in the presence of deoxyuridylate biotinylated at the 5'-position of the uracil moiety. The resulting probe includes the biotinylated uridylate in place of thymidylate residues and can be detected [via the biotin moieties] by any of a number of commercially available detection systems based on binding of streptavidin to the biotin. Such commercially available detection systems can be obtained, for example, from Enzo Biochemicals, Inc. [New York, N.Y.]. Any other label known to those of skill in the art, including non-radioactive labels, may be used as long as it renders the probes sufficiently detectable, which is a function of the sensitivity of the assay, the time available [for culturing cells, extracting DNA, and hybridization assays], the quantity of DNA or RNA available as a source of the probe, the particular label and the means used to detect the label.

Once sequences with a sufficiently high degree of homology to the probe are identified, they can readily be isolated by standard techniques, which are described, for example, by Maniatis et al. ((1982) Molecular Cloning: A Laboratory Manual, Cold Spring Harbor Laboratory Press, Cold Spring Harbor, N.Y.).

As used herein, conditions under which DNA molecules form stable hybrids and are considered substantially homologous are such that DNA molecules with at least about 60% complementarity form stable hybrids. Such DNA fragments are herein considered to be "substantially homologous". For example, DNA that encodes a particular protein is substantially homologous to another DNA fragment if the DNA forms stable hybrids such that the sequences of the fragments are at least about 60% complementary and if a protein encoded by the DNA retains its activity.

For purposes herein, the following stringency conditions are defined:

1) high stringency: 0.1×SSPE, 0.1% SDS, 65° C.
2) medium stringency: 0.2×SSPE, 0.1% SDS, 50° C.
3) low stringency: 1.0 x SSPE, 0.1% SDS, 50° C.

or any combination of salt and temperature and other reagents that result in selection of the same degree of mismatch or matching.

As used herein, immunoprotective refers to the ability of a vaccine or exposure to an antigen or immunity-inducing agent, to confer upon a host to whom the vaccine or antigen is administered or introduced, the ability to resist infection by a disease-causing pathogen or to have reduced symptoms. The selected antigen is typically an antigen that is presented by the pathogen.

As used herein, all assays and procedures, such as hybridization reactions and antibody-antigen reactions, unless otherwise specified, are conducted under conditions recognized by those of skill in the art as standard conditions.

A. Preparation of cell lines containing MACs

The methods, cells and MACs provided herein are produced by virtue of the discovery of the existence of a higher-order replication unit [megareplicon] of the centromeric region. This megareplicon is delimited by a primary replication initiation site [megareplicator], and appears to facilitate replication of the centromeric heterochromatin, and most likely, centromeres. Integration of heterologous DNA into the megareplicator region or in close proximity thereto, initiates a large-scale amplification of megabase-size chromosomal segments, which leads to de novo chromosome formation in living cells.

Cell lines containing MACs can be prepared by transforming cells, preferably a stable cell line, with a heterologous DNA fragment that encodes a selectable marker, culturing under selective conditions, and identifying cells that have a multicentric, typically dicentric, chromosome. These cells can then be manipulated as described herein to produce the minichromosomes and other MACs, particularly the heterochromatic SATACs as described herein.

Development of a multicentric, particularly dicentric, chromosome typically is effected through integration of the heterologous DNA in the pericentric heterochromatin. Thus, the probability of incorporation can be increased by including DNA, such as satellite DNA, in the heterologous fragment that encodes the selectable marker. The resulting cell lines can then be treated as the exemplified cells herein to produce cells in which the dicentric chromosome has fragmented and to introduce additional selective markers into the dicentric chromosome, whereby amplification of the pericentric heterochromatin will produce the heterochromatic chromosomes. The following discussion is with reference to the EC3/7 line and use of resulting cells. The same procedures can be applied to any other cells, particularly cell lines to create SATACs and euchromatic minichromosomes.

1. Formation of de novo chromosomes

De novo centromere formation in a transformed mouse LMTK-fibro-blast cell line [EC3/7] after cointegration of A constructs [ACM8 and AgtWESneo] carrying human and bacterial DNA [Hadlaczky et al. (1991) *Proc. Natl. Acad. Sci. U.S.A.* 88:8106–8110 and U.S. application Ser. No. 08/375,271] has been shown. The integration of the "heterologous" engineered human, bacterial and phage DNA, and the subsequent amplification of mouse and heterologous DNA that led to the formation of a dicentric chromosome, occurred at the centromeric region of the short arm of a mouse chromosome. By G-banding, this chromosome was identified as mouse chromosome 7. Because of the presence of two functionally active centromeres on the same chromosome, regular breakages occur between the centromeres. Such specific chromosome breakages gave rise to the appearance [in approximately 10% of the cells] of a chromosome fragment carrying the neo-centromere. From the EC3/7 cell line [see, U.S. Pat. No. 5,288,625, deposited at the European Collection of Animal Cell Culture (hereinafter ECACC) under accession no. 90051001; see, also Hadlaczky et al. (1991) *Proc. Natl. Acad. Sci. U.S.A.* 88:8106–8110, and U.S. application Ser. No. 08/375,271 and the corresponding published European application EP 0 473 253, two sublines [EC3/7C5 and EC3/7C6] were selected by repeated single-cell cloning. In these cell lines, the neo-centromere was found exclusively on a minichromosome [neo-minichromosome], while the formerly dicentric chromosome carried traces of "heterologous" DNA.

It has now been discovered that integration of DNA encoding a selectable marker in the heterochromatic region of the centromere led to formation of the dicentric chromosome.

2. The neo-minichromosome

The chromosome breakage in the EC3/7 cells, which separates the neo-centromere from the mouse chromosome, occurred in the G-band positive "heterologous" DNA region. This is supported by the observation of traces of λ and human DNA sequences at the broken end of the formerly dicentric chromosome. Comparing the G-band pattern of the chromosome fragment carrying the neo-centromere with that of the stable neo-minichromosome, it is apparent that the neo-minichromosome is an inverted duplicate of the chromosome fragment that bears the neo-centromere. This is supported by the observation that although the neo-minichromosome carries only one functional centromere, both ends of the minichromosome are heterochromatic, and mouse satellite DNA sequences were found in these heterochromatic regions by in situ hybridization.

Mouse cells containing the minichromosome, which contains multiple repeats of the heterologous DNA, which in the exemplified embodiment is λ DNA and the neomycin-resistance gene, can be used as recipient cells in cell transformation. Donor DNA, such as selected heterologous DNA containing λ DNA linked to a second selectable marker, such as the gene encoding hygromycin phosphotransferase which confers hygromycin resistance [hyg], can be introduced into the mouse cells and integrated into the minichromosomes by homologous recombination of λ DNA in the donor DNA with that in the minichromosomes. Integration is verified by in situ hybridization and Southern blot analyses. Transcription and translation of the heterologous DNA is confirmed by primer extension and immuno-blot analyses.

For example, DNA has been targeted into the neo-minichromosome in EC3/7C5 cells using a i DNA-containing construct [pNem1ruc] that also contains DNA encoding hygromycin resistance and the *Renilla luciferase* gene linked to a promoter, such as the cytomegalovirus [CMV] early promoter, and the bacterial neomycin resistance-encoding DNA. Integration of the donor DNA into the chromosome in selected cells [designated PHN4] was confirmed by nucleic acid amplification [PCR] and in situ hybridization. Events that would produce a neo-minichromosome are depicted in FIG. 1.

The resulting engineered minichromosome that contains the heterologous DNA can then be transferred by cell fusion into a recipient cell line, such as Chinese hamster ovary cells [CHO] and correct expression of the heterologous DNA can be verified. Following production of the cells, metaphase chromosomes are obtained, such as by addition of colchicine, and the chromosomes purified by addition of AT- and GC-specific dyes on a dual laser beam based cell sorter (see Example 10 B for a description of methods of isolating artificial chromomsomes). Preparative amounts of chromosomes [$5 \times 10^4$–$5 \times 10^7$ chromosomes/ml] at a purity of 95% or higher can be obtained. The resulting chromosomes are used for delivery to cells by methods such as microinjection and liposome-mediated transfer.

Thus, the neo-minichromosome is stably maintained in cells, replicates autonomously, and permits the persistent long-term expression of the neo gene under non-selective culture conditions. It also contains megabases of heterologous known DNA [λ DNA in the exemplified embodiments] that serves as target sites for homologous recombination and integration of DNA of interest. The neo-minichromosome is, thus, a vector for genetic engineering of cells.

The methods herein provide means to induce the events that lead to formation of the neo-minichromosome by introducing heterologous DNA with a selective marker [preferably a dominant selectable marker] into cells and culturing the cells under selective conditions. As a result, cells that contain a multicentric, e.g., dicentric chromosome, or fragments thereof, generated by amplification are produced. Cells with the dicentric chromosome can then be treated to destabilize the chromosomes with agents, such as BrdU and/or culturing under selective conditions, resulting in cells in which the dicentric chromosome has formed two chromosomes, a so-called minichromosome, and a formerly dicentric chromosome that has typically undergone amplification in the heterochromatin where the heterologous DNA has integrated to produce a SATAC or a sausage chromosome [discussed below]. These cells can be fused with other cells to separate the minichromosome from the formerly dicentric chromosome into different cells so that each type of MAC can be manipulated separately.

3. Preparation of SATACs

Figure 2:
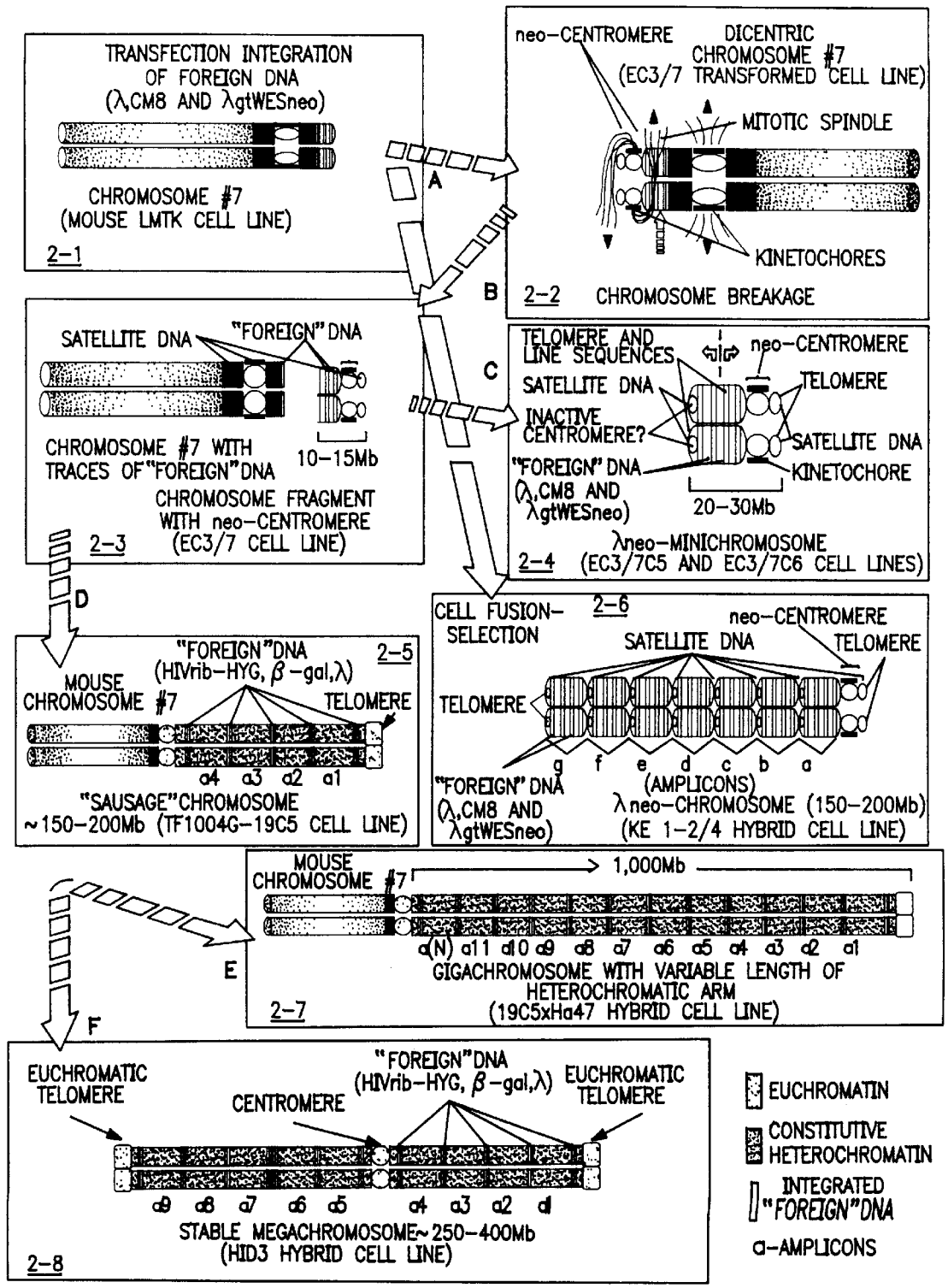
FIG. 2 shows a schematic summary of the manner in which the observed new chromosomes would form, and the relationships among the different de novo formed chromosomes. In particular, this figure shows a schematic drawing of the de novo chromosome formation initiated in the centromeric region of mouse chromosome 7. (A) A single E-type amplification in the centromeric region of chromosome 7 generates a neo-centromere linked to the integrated "foreign" DNA, and forms a dicentric chromosome. Multiple E-type amplification forms the λ neo-chromosome, which separates from the remainder of mouse chromosome 7 through a specific breakage between the centromeres of the dicentric chromosome and which was stabilized in a mouse-hamster hybrid cell line; (B) Specific breakage between the centromeres of a dicentric chromosome 7 generates a chromosome fragment with the neo-centromere, and a chromosome 7 with traces of heterologous DNA at the end; (C) Inverted duplication of the fragment bearing the neo-centromere results in the formation of a stable neo-minichromosome; (D) Integration of exogenous DNA into the heterologous DNA region of the formerly dicentric chromosome 7 initiates H-type amplification, and the formation of a heterochromatic arm. By capturing a euchromatic terminal segment, this new chromosome arm is stabilized in the form of the "sausage" chromosome; (E) BrdU [5-bromodeoxyuridine] treatment and/or drug selection induce further H-type amplification, which results in the formation of an unstable gigachromosome: (F) Repeated BrdU treatments and/or drug selection induce further H-type amplification including a centromere duplication, which leads to the formation of another heterochromatic chromosome arm. It is split off from the chromosome 7 by chromosome breakage, and by acquiring a terminal segment, the stable megachromosome is formed.
Figure 3:
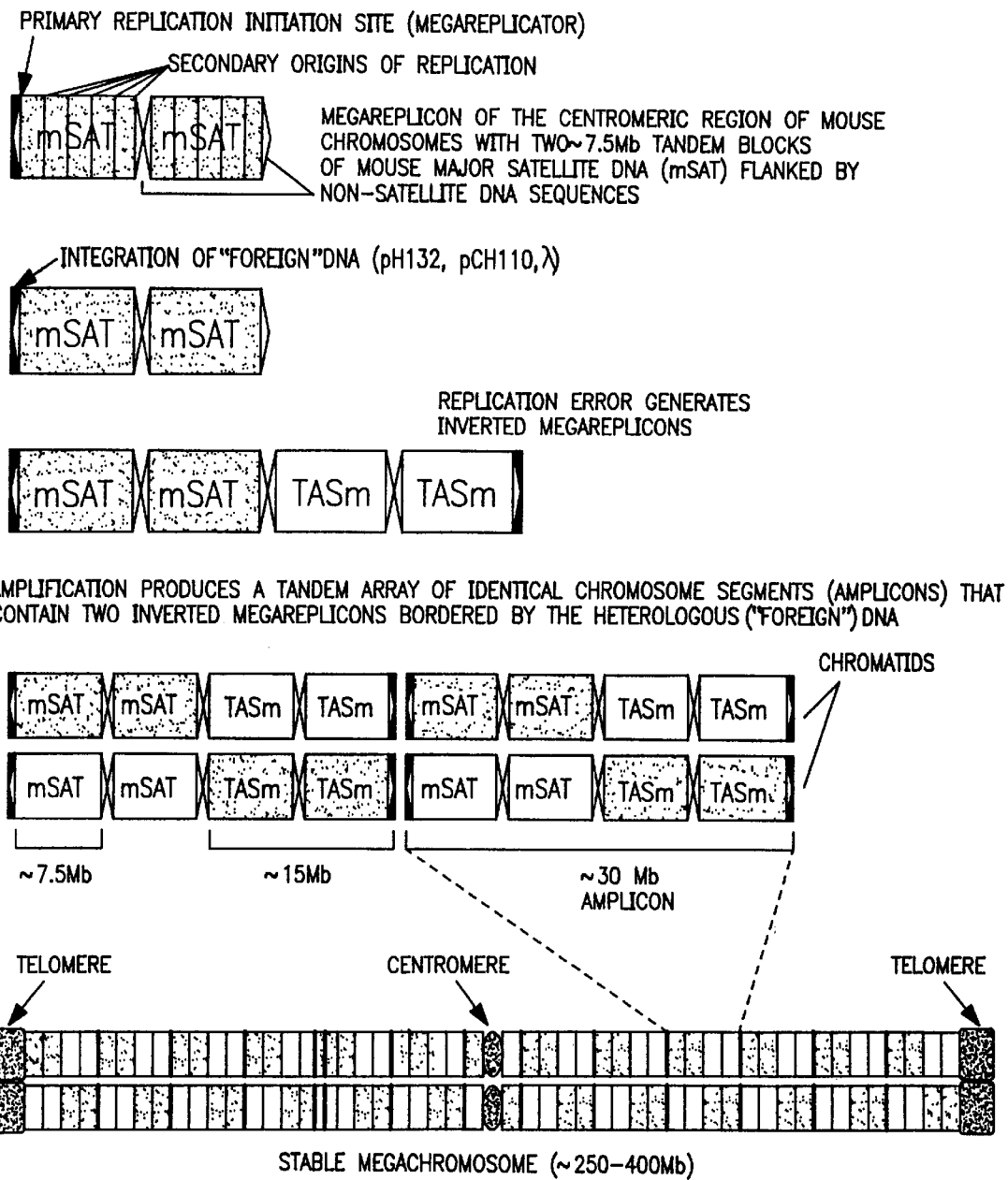
FIG. 3 is a schematic diagram of the replicon structure and a scheme by which a megachromosome could be produced.

An exemplary protocol for preparation of SATACs is illustrated in FIG. 2 [particularly D, E and F] and FIG. 3 [see, also the EXAMPLES, particularly EXAMPLES 4–7].

To prepare a SATAC, the starting materials are cells, preferably a stable cell line, such as a fibroblast cell line, and a DNA fragment that includes DNA that encodes a selective marker. The DNA fragment is introduced into the cell by methods of DNA transfer, including but not limited to direct uptake using calcium phosphate, electroporation, and lipid-mediated transfer. To insure integration of the DNA fragment in the heterochromatin, it is preferable to start with DNA that will be targeted to the pericentric heterochromatic region of the chromosome, such as ACM8 and vectors provided herein, such as pTEMPUD [FIG. 5] that include satellite DNA. After introduction of the DNA, the cells are grown under selective conditions. The resulting cells are examined and any that have multicentric, particularly dicentric, chromosomes, or heterochromatic chromosomes or sausage chromosomes or other such structure [see, FIGS. 2D, 2E and 2F] are selected.

In particular, if a cell with a dicentric chromosome is selected, it can be grown under selective conditions, or, preferably, additional DNA encoding a second selectable marker is introduced, and the cells grown under conditions selective for the second marker. The resulting cells should include chromosomes that have structures similar to those depicted in FIGS. 2D, 2E, 2F. Cells with a structure, such as the sausage chromosome, FIG. 2D, can be selected and fused with a second cell line to eliminate other chromosomes that are not of interest. If desired, cells with other chromosomes can be selected and treated as described herein. If a cell with a sausage chromosome is selected, it can be treated with an agent, such as BrdU, that destabilizes the chromosome so that the heterochromatic arm forms a chromosome that is substantially heterochromatic [i.e., a megachromosome, see, FIG. 2F]. Structures such as the gigachromsome in which the heterochromatic arm has amplified but not broken off from the euchromatic arm, will also be observed. The megachromosome is a stable chromosome. Further manipulation, such as fusions and growth in selective conditions and/or BrdU treatment or other such treatment, can lead to fragmentation of the megachromosome to form smaller chromosomes that have the amplicon as the basic repeating unit.

Figure 5:
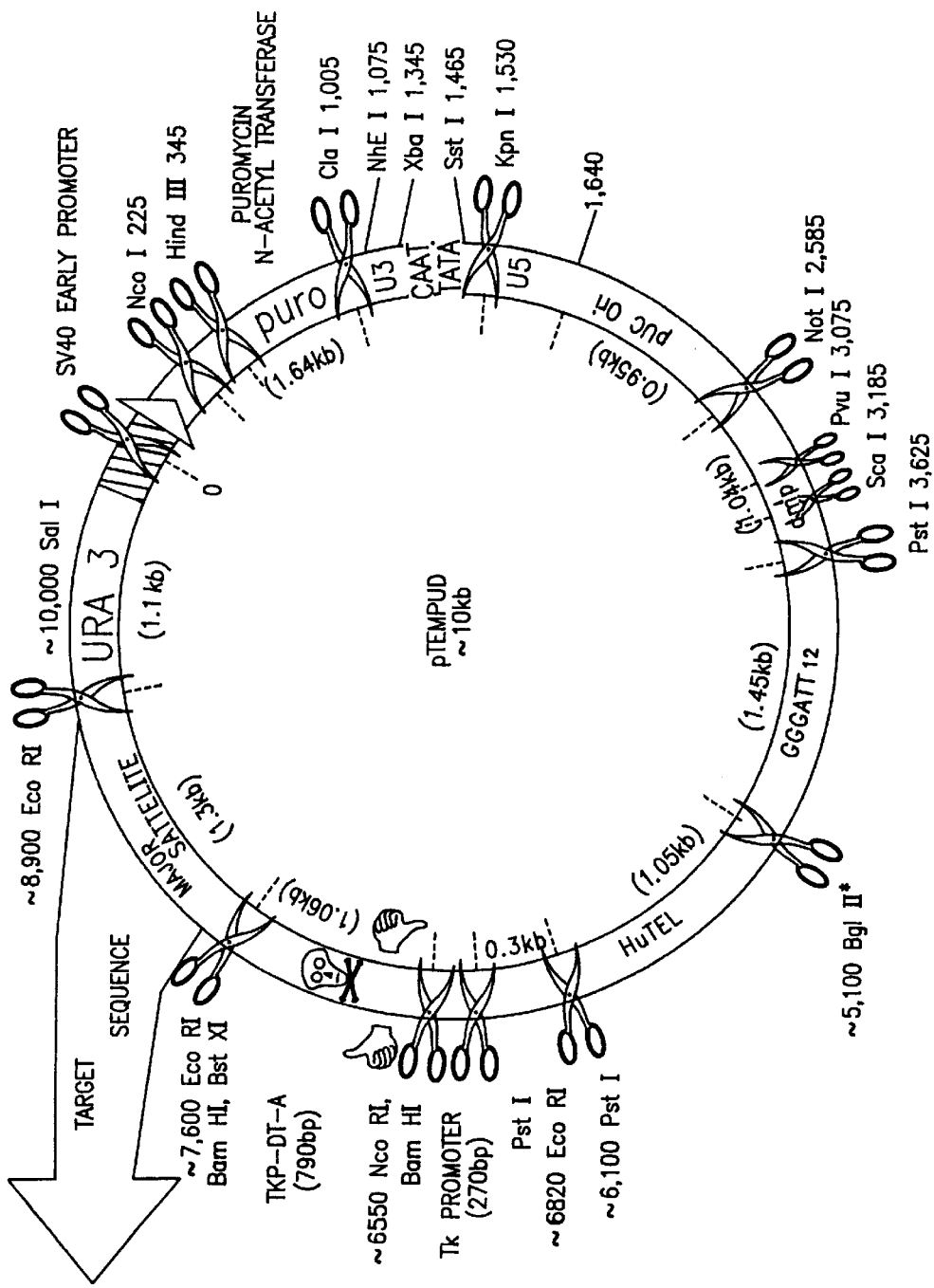
FIG. 5 is a diagram of the plasmid pTEMPUD.

The megachromosome can be further fragmented in vivo using a chromosome fragmentation vector, such as pTEMPUD [see, FIG. 5 and EXAMPLE 12] to ultimately produce a chromosome that comprises a smaller stable replicable unit, about 15 Mb–60 Mb, containing one to four megareplicons.

Thus, the stable chromosomes formed de novo that originate from the short arm of mouse chromosome 7 have been analyzed. This chromosome region shows a capacity for amplification of large chromosome segments, and promotes de novo chromosome formation. Large-scale amplification at the same chromosome region leads to the formation of dicentric and multicentric chromosomes, a minichromosome, the 150–200 Mb size λ neo-chromosome, the "sausage" chromosome, the 500–1000 Mb gigachromosome, and the stable 250–400 Mb megachromosome.

A clear segmentation is observed along the arms of the megachromosome, and analyses show that the building units of this chromosome are amplicons of ~30 Mb composed of mouse major satellite DNA with the integrated "foreign" DNA sequences at both ends. The ~30 Mb amplicons are composed of two ~15 Mb inverted doublets of ~7.5 Mb mouse major satellite DNA blocks, which are separated from each other by a narrow band of non-satellite sequences [see, e.g., FIG. 3]. The wider non-satellite regions at the amplicon borders contain integrated, exogenous [heterologous] DNA, while the narrow bands of non-satellite DNA sequences within the amplicons are integral parts of the pericentric heterochromatin of mouse chromosomes. These results indicate that the ~7.5 Mb blocks flanked by non-satellite DNA are the building units of the pericentric heterochromatin of mouse chromosomes, and the ~15 Mb size pericentric regions of mouse chromosomes contain two ~7.5 Mb units.

Apart from the euchromatic terminal segments, the whole megachromosome is heterochromatic, and has structural homogeneity. Therefore, this large chromosome offers a unique possibility for obtaining information about the amplification process, and for analyzing some basic characteristics of the pericentric constitutive heterochromatin, as a vector for heterologous DNA, and as a target for further fragmentation.

As shown herein, this phenomenon is generalizable and can be observed with other chromosomes. Also, although these de novo formed chromosome segments and chromosomes appear different, there are similarities that indicate that a similar amplification mechanism plays a role in their formation: (i) in each case, the amplification is initiated in the centromeric region of the mouse chromosomes and large (Mb size) amplicons are formed; (ii) mouse major satellite DNA sequences are constant constituents of the amplicons, either by providing the bulk of the heterochromatic amplicons [H-type amplification], or by bordering the aeuchromatic amplicons [E-type amplification]; (iii) formation of inverted segments can be demonstrated in the λ neo-chromosome and megachromosome; (iv) chromosome arms and chromosomes formed by the amplification are stable and functional.

The presence of inverted chromosome segments seems to be a common phenomenon in the chromosomes formed de novo at the centromeric region of mouse chromosome 7. During the formation of the neo-minichromosome, the event leading to the stabilization of the distal segment of mouse chromosome 7 that bears the neo-centromere may have been the formation of its inverted duplicate. Amplicons of the megachromosome are inverted doublets of ~7.5 Mb mouse major satellite DNA blocks.

4. Cell lines

Cell lines that contain MACs, such as the minichromosome, the λ-neo chromosome, and the SATACs are provided herein or can be produced by the methods herein. Such cell lines provide a convenient source of these chromosomes and can be manipulated, such as by cell fusion or production of microcells for fusion with selected cell lines, to deliver the chromosome of interest into hybrid cell lines. Exemplary cell lines are described herein and some have been deposited with the ECACC.

a. EC3/7C5 and EC3/7C6

Cell lines EC3/7C5 and EC3/7C6 were produced by single cell cloning of EC3/7. For exemplary purposes EC3/7C5 has been deposited with the ECACC. These cell lines contain a minichromosome and the formerly dicentric chromosome from EC3/7. The stable mini-chromosomes in cell lines EC3/7C5 and EC3/7C6 appear to be the same and they seem to be duplicated derivatives of the 10–15 Mb "broken-off" fragment of the dicentric chromosome. Their similar size in these independently generated cell lines might indicate that ~20–30 Mb is the minimal or close to the minimal physical size for a stable minichromosome.

b. TF1004G19

Introduction of additional heterologous DNA, including DNA encoding a second selectable marker, hygromycin phosphotransferase, i.e., the hygromycin-resistance gene, and also a detectable marker, β-galactosidase (i.e., encoded by the lacz gene), into the EC3/7C5 cell line and growth under selective conditions produced cells designated TF1004G19. In particular, this cell line was produced from the EC3/7C5 cell line by cotransfection with plasmids pH132, which contains an anti-HIV ribozyme and hygromycin-resistance gene, pCH110 [encodes, β-galactosidase] and λ phage [λcI 875 Sam 7] DNA and selection with hygromycin B.

Detailed analysis of the TF1004G19 cell line by in situ hybridization with λ phage and plasmid DNA sequences revealed the formation of the sausage chromosome. The formerly dicentric chromosome of the EC3/7C5 cell line translocated to the end of another acrocentric chromosome. The heterologous DNA integrated into the pericentric heterochromatin of the formerly dicentric chromosome and is amplified several times with megabases of mouse pericentric heterochromatic satellite DNA sequences [FIG. 2D] forming the "sausage" chromosome. Subsequently the acrocentric mouse chromosome was substituted by a euchromatic telomere.

In situ hybridization with biotin-labeled subfragments of the hygromycin-resistance and, β-galactosidase genes resulted in a hybridization signal only in the heterochromatic arm of the sausage chromosome, indicating that in TF1004G19 transformant cells these genes are localized in the pericentric heterochromatin.

A high level of gene expression, however, was detected. In general, heterochromatin has a silencing effect in Drosophila, yeast and on the HSV-tk gene introduced into satellite DNA at the mouse centromere. Thus, it was of interest to study the TF1004G19 transformed cell line to confirm that genes located in the heterochromatin were indeed expressed, contrary to recognized dogma.

For this purpose, subclones of TF1004G19, containing a different sausage chromosome [see FIG. 2D], were established by single cell cloning. Southern hybridization of DNA isolated from the subclones with subfragments of hygromycin phosphotransferase and lacZ genes showed a close correlation between the intensity of hybridization and the length of the sausage chromosome. This finding supports the conclusion that these genes are localized in the heterochromatic arm of the sausage chromosome.

(1) TF1004G-19C5

TF1 004G-19C5 is a mouse LMTK- fibroblast cell line containing neo-minichromosomes and stable "sausage" chromosomes. It is a subclone of TF1004G19 and was generated by single-cell cloning of the TF1004G19 cell line. It has been deposited with the ECACC as an exemplary cell line and exemplary source of a sausage chromosome. Subsequent fusion of this cell line with CHO K20 cells and selection with hygromycin and G418 and HAT (hypoxanthine, aminopteria, and thymidine medium; see Szybalski et al. (1962) *Proc. Natl. Acad. Sci.* 48:2026) resulted in hybrid cells (designated 19C5xHa4) that carry the sausage chromosome and the neo-minichromosome. BrdU treatment of the hybrid cells, followed by single cell cloning and selection with G418 and/or hygromycin produced various cells that carry chromosomes of interest, including G43 and G3D5.

(2) other subclones

Cell lines GB43 and G3D5 were obtained by treating 19C5xHa4 cells with BrdU followed by growth in G418-containing selective medium and retreatment with BrdU. The two cell lines were isolated by single cell cloning of the selected cells. GB43 cells contain the neo-minichromosome only. G3D5, which has been deposited with the ECACC, carries the neo-minichromosome and the megachromosome. Single cell cloning of this cell line followed by growth of the subclones in G418- and hygromycin-containing medium yielded subclones such as the GHB42 cell line carrying the neo-minichromosome and the megachromosome. H1D3 is a mouse-hamster hybrid cell line carrying the megachromosome, but no neo-minichromosome, and was generated by treating 19C5xHa4 cells with BrdU followed by growth in hygromycin- containing selective medium and single cell subcloning of selected cells. Fusion of this cell line with the CD4+HeLa cell line that also carries DNA encoding an additional selection gene, the neomycin-resistance gene, produced cells [designated H1xHE41 cells] that carry the megachromosome as well as a human chromosome that carries CD4neo. Further BrdU treatment and single cell cloning produced cell lines, such as 1B3, that include cells with a truncated megachromosome.

5. DNA constructs used to transform the cells

Figure 4:
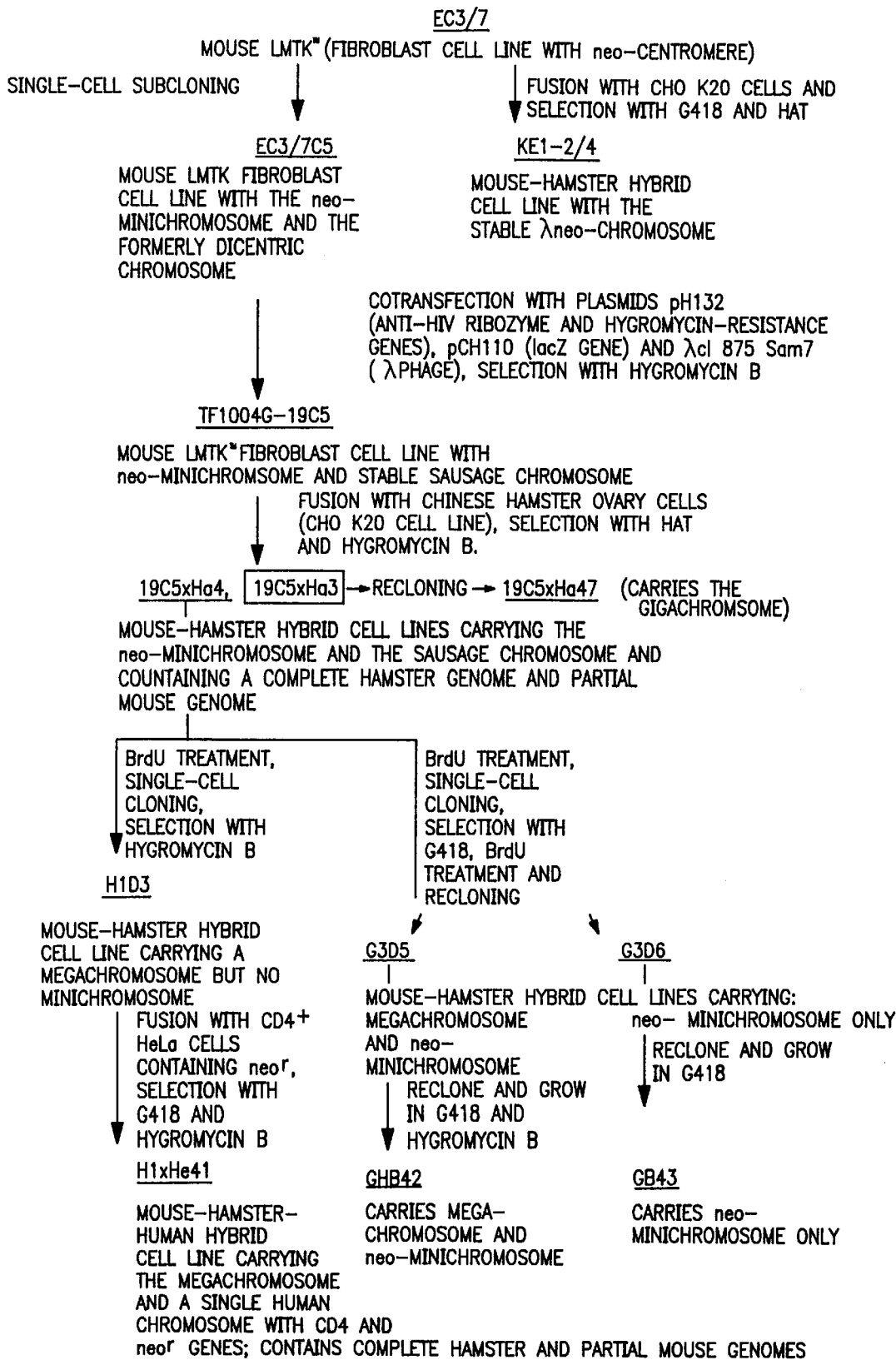
FIG. 4 sets forth the relationships among some of the exemplary cell lines described herein.

Heterologous DNA can be introduced into the cells by transfection or other suitable method at any stage during preparation of the chromosomes [see, e.g., FIG. 4]. In general, incorporation of such DNA into the MACs is assured through site-directed integration, such as may be accomplished by inclusion of λ-DNA in the heterologous DNA (for the exemplified chromosomes), and also an additional selective marker gene. For example, cells containing a MAC, such as the minichromosome or a SATAC, can be cotransfected with a plasmid carrying the desired heterologous DNA, such as DNA encoding an HIV ribozyme, the cystic fibrosis gene, and DNA encoding a second selectable marker, such as hygromycin resistance. Selective pressure is then applied to the cells by exposing them to an agent that is harmful to cells that do not express the new selectable marker. In this manner, cells that include the heterologous DNA in the MAC are identified. Fusion with a second cell line can provide a means to produce cell lines that contain one particular type of chromosomal structure or MAC.

Various vectors for this purpose are provided herein [see, Examples] and others can be readily constructed. The vectors preferably include DNA that is homologous to DNA contained within a MAC in order to target the DNA to the MAC for integration therein. The vectors also include a selectable marker gene and the selected heterologous gene (s) of interest. Based on the disclosure herein and the knowledge of the skilled artisan, one of skill can construct such vectors.

Of particular interest herein is the vector pTEMPUD and derivatives thereof that can target DNA into the heterochromatic region of selected chromosomes. These vectors can also serve as fragmentation vectors [see, e.g., Example 12].

Heterologous genes of interest include any gene that encodes a therapeutic product and DNA encoding gene products of interest. These genes and DNA include, but are not limited to: the cystic fibrosis gene [CF], the cystic fibrosis transmembrane regulator (CFTR) gene [see, e.g., U.S. Pat. No. 5,240,846; Rosenfeld et al. (1992) *Cell* 68:143–155; Hyde et al. (1993) *Nature* 362: 250–255;

Kerem et al. (1989) *Science* 245:1073–1080; Riordan et al.(1989) *Science* 245:1066–1072; Rommens et al. (1989) *Science* 245:1059–1065; Osborne et al. (1991) *Am. J. Hum. Genetics* 48:6089–6122; White et al. (1990) *Nature* 344:665–667; Dean et al. (1990) *Cell* 61:863–870; Erlich et al. (1991) *Science* 252:1643; and U.S. Pat. Nos. 5,453,357, 5,449,604, 5,434,086, and 5,240,846, which provides a retroviral vector encoding the normal CFTR gene].

B. Isolation of artificial chromosomes

The MACs provided herein can be isolated by any suitable method known to those of skill in the art. Also, a method is provided herein for effecting substantial purification, particularly of the SATACs. SATACs have been isolated by fluorescence-activated cell sorting [FACS]. This method takes advantage of the nucleotide base content of the SATACs, which, by virtue of their heterochromatic DNA content, will differ from any other chromosomes in a cell. In particular, metaphase chromosomes are isolated (e.g., by addition of colchicine) and stained with base-specific dyes, such as Hoechst 33258 and chromomycin A3. Fluorescence-activated cell sorting will separate the SATACs from the genomic chromosomes. A dual-laser cell sorter [FACStar Plus and FAXStar Vantage Becton Dickinson Immunocytometry System] in which two lasers were set to excite the dyes separately, allowed a bivariate analysis of the chromosomes by base-pair composition and size. Cells containing such SATACs can be similarly sorted.

C. Introduction of artificial chromosomes into cells, tissues, animals and plants Suitable hosts for introduction of the MACs provided herein, include, but are not limited to, any animal or plant, cell or tissue thereof, including, but not limited to: mammals, birds, reptiles, amphibians, insects, fish, arachnids, tobacco, tomato, wheat, plants and algae. The MACs, if contained in cells, may be introduced by cell fusion or microcell fusion or, if the MACs have been isolated from cells, they may be introduced into host cells by any method known to those of skill in this art, including but not limited to: direct DNA transfer, electroporation, lipid-mediated transfer, e.g., lipofection and liposomes, micro-projectile bombardment, microinjection in cells and embryos, protoplast regeneration for plants, and any other suitable method [see, e.g., Weissbach et al. (1988) Methods for Plant Molecular Biology, Academic Press, N.Y., Section VIII, pp. 421–463; Grierson et al. (1988) Plant Molecular Biology, 2d Ed., Blackie, London, Ch. 7–9; see, also U.S. Pat. Nos. 5,491,075; 5,482,928; and 5,424,409; see, also, e.g., U.S. Pat. No. 5,470,708, which describes particle-mediated transformation of mammalian unattached cells].

Other methods for introducing DNA into cells include nuclear microinjection and bacterial protoplast fusion with intact cells. Polycations, such as polybrene and polyornithine, may also be used. For various techniques for transforming mammalian cells, see e.g., Keown et al. *Methods in Enzymology* (1990) Vol. 185, pp. 527–537; and Mansour et al. (1988) *Nature* 336:348–352.

For example, isolated, purified artificial chromosomes can be injected into an embryonic cell line such as a human kidney primary embryonic cell line [ATCC accession number CRL 1573] or embryonic stem cells [see, e.g., Hogan et al. (1994) *Manipulating the Mouse Embryo, A :Laboratory Manual,* Cold Spring Harbor Laboratory Press, Cold Spring Harbor, N.Y., see, especially, pages 255–264 and Appendix 3]. Preferably the chromosomes are introduced by microinjection, using a system such as the Eppendorf automated microinjection system, and grown under selective conditions, such as in the presence of hygromycin B or neomycin.

1. Methods for introduction of chromosomes into hosts

Depending on the host cell used, transformation is done using standard techniques appropriate to such cells. These methods include any, including those described herein, known to those of skill in the art.

a. DNA uptake

For mammalian cells that do not have cell walls, the calcium phosphate precipitation method for introduction of exogenous DNA [see, e.g., Graham et al. (1978) *Virology* 52:456–457; Wigler et al. (1979) *Proc. Natl. Acad. Sci. U.S.A.* 76:1373–1376; and *Current Protocols in Molecular Biology,* Vol. 1, Wiley Inter-Science, Supplement 14, Unit 9.1.1–9.1.9 (1990)] is often preferred. DNA uptake can be accomplished by DNA alone or in the presence of polyethylene glycol [PEG-mediated gene transfer], which is a fusion agent, or by any variations of such methods known to those of skill in the art [see, e.g., U.S. Pat. No. 4,684,611].

Lipid-mediated carrier systems are also among the preferred methods for introduction of DNA into cells [see, e.g., Teifel et al. (1995) *Biotechniques* 19:79–80; Albrecht et al. (1996) *Ann. Hematol.* 72:73–79; Holmen et al. (1995) *In Vitro Cell Dev. Biol. Anim.* 31:347–351; Remy et al. (1994) *Bioconjug. Chem.* 5:647–654; Le Bolch et al. (1995) *Tetrahedron Lett.* 36:6681–6684; Loeffler et al. (1993) *Meth. Enzymol.* 217:599–618]. Lipofection [see, e.g., Strauss (1996) *Meth. Mol. Biol.* 54:307–327] may also be used to introduce DNA into cells. This method is particularly well-suited for transfer of exogenous DNA into chicken cells (e.g., chicken blastodermal cells and primary chicken fibroblasts; see Brazolot et al. (1991) *Mol. Repro. Dev.* 30:304–312). In particular, DNA of interest can be introduced into chickens in operative linkage with promoters from genes, such as lysozyme and ovalbumin, that are expressed in the egg, thereby permitting expression of the heterologous DNA in the egg.

Additional methods useful in the direct transfer of DNA into cells include particle gun electrofusion [see, e.g., U.S. Pat. Nos. 4,955,378, 4,923,814, 4,476,004, 4,906,576 and 4,441,972] and virion-mediated gene transfer.

A commonly used approach for gene transfer in land plants involves the direct introduction of purified DNA into protoplasts. The three basic methods for direct gene transfer into plant cells include: 1) polyethylene glycol [PEG]-mediated DNA uptake, 2) electroporation-mediated DNA uptake and 3) microinjection. In addition, plants may be transformed using ultrasound treatment [see, e.g., International PCT application publication No. WO 91/00358].

b. Electroporation

Electroporation involves providing high-voltage electrical pulses to a solution containing a mixture of protoplasts and foreign DNA to create reversible pores in the membranes of plant protoplasts as well as other cells. Electroporation is generally used for prokaryotes or other cells, such as plants that contain substantial cell-wall barriers. Methods for effecting electroporation are well known [see, e.g., U.S. Pat. Nos. 4,784,737, 5,501,967, 5,501,662, 5,019,034, 5,503,999; see, also Frommet al. (1985) *Proc. Natl. Acad. Sci. U.S.A.* 82:5824–5828].

For example, electroporation is often used for transformation of plants [see, e.g., *Ag Biotechnology News* 7:3 and 17 (September/October 1990)]. In this technique, plant protoplasts are electroporated in the presence of the DNA of interest that also includes a phenotypic marker. Electrical impulses of high field strength reversibly permeabilize biomembranes allowing the introduction of the plasmids. Electroporated plant protoplasts reform the cell wall, divide, and form plant callus. Transformed plant cells will be identified by virtue of the expressed phenotypic marker. The exogenous DNA may be added to the protoplasts in any form such as, for example, naked linear, circular or supercoiled DNA, DNA encapsulated in liposomes, DNA in spheroplasts, DNA in other plant protoplasts, DNA complexed with salts, and other methods.

c. Microcells

The chromosomes can be transferred by preparing microcells containing an artificial chromosome and then fusing with selected target cells. Methods for such preparation and fusion of microcells are well known [see the Examples and also see, e.g., U.S. Pat. Nos. 5,240,840, 4,806,476, 5,298,429, 5,396,767, Fournier (1981) *Proc. Natl. Acad. Sci. U.S.A.* 78:6349–6353; and Lambert et al. (1991) *Proc. Natl. Acad. Sci. U.S.A.* 88:5907–59]. Microcell fusion, using microcells that contain an artificial chromosome, is a particularly useful method for introduction of MACs into avian cells, such as DT40 chicken pre-B cells [for a description of DT40 cell fusion, see, e.g., Dieken et al. (1996) *Nature Genet.* 12:174–182].

2. Hosts

Suitable hosts include any host known to be useful for introduction and expression of heterologous DNA. Of particular interest herein, animal and plant cells and tissues, including, but not limited to insect cells and larvae, plants, and animals, particularly transgenic animals, and animal cells. Other hosts include, but are not limited to mammals, birds, particularly fowl such as chickens, reptiles, amphibians, insects, fish, arachnids, tobacco, tomato, wheat, monocots, dicots and algae, and any host into which introduction of heterologous DNA is desired. Such introduction can be effected using the MACs provided herein, or, if necessary by using the MACs provided herein to identify species-specific centromeres and/or functional chromosomal units and then using the resulting centromeres or chromosomal units as artificial chromosomes, or alternatively, using the methods exemplified herein for production of MACs to produce species-specific artificial chromosomes.

a. Introduction of DNA into embryos for production of transgenic animals and introduction of DNA into animal cells Transgenic animals can be produced by introducing exogenous genetic material into a pronucleus of a mammalian zygote by microinjection [see, e.g., U.S. Pat. Nos. 4,873,191 and 5,354,674; see, also, International PCT application publication No. WO95/14769, which is based on U.S. application Ser. No. 08/159,084]. The zygote is capable of development into a mammal. The embryo or zygote is transplanted into a host female uterus and allowed to develop. Detailed protocols and examples are set forth below.

Transgenic chickens can be produced by injection of dispersed blastodermal cells from Stage X chicken embryos into recipient embryos at a similar stage of development [see e.g., Etches et al. (1993) *Poultry Sci.* 72:882–889; Petitte et al. (1990) *Development* 108:185–189]. Heterologous DNA is first introduced into the donor blastodermal cells using methods such as, for example, lipofection [see, e.g., Brazolot et al. (1991) *Mol. Repro. Dev.* 30:304–312] or microcell fusion [see, e.g., Dieken et al. (1996) *Nature Genet.* 12:174–182]. The transfected donor cells are then injected into recipient chicken embryos [see e.g., Carsience et al. (1993) *Development* 117: 669–675]. The recipient chicken embryos within the shell are candled and allowed to hatch to yield a germline chimeric chicken.

DNA can be introduced into animal cells using any known procedure, including, but not limited to: direct uptake, incubation with polyethylene glycol [PEG], microinjection, electroporation, lipofection, cell fusion, microcell fusion, particle bombardment, including microprojectile bombardment [see, eg., U.S. Pat. No. 5,470,708, which provides a method for transforming unattached mammalian cells via particle bombardment], and any other such method. For example, the transfer of plasmid DNA in liposomes directly to human cells in situ has been approved by the FDA for use in humans [see, eg., Nabel, et al. (1990) *Science* 249:1285–1288 and U.S. Pat. No. 5,461,032].

b. Introduction of heterologous DNA into plants.

Numerous methods for producing or developing transgenic plants are available to those of skill in the art. The method used is primarily a function of the species of plant. These methods include, but are not limited to: direct transfer of DNA by processes, such as PEG-induced DNA uptake, protoplast fusion, microinjection, electroporation, and microprojectile bombardment [see, e.g., Uchimiya et al. (1989) *J. of Biotech.* 12: 1–20 for a review of such procedures, see, also, e.g., U.S. Pat. Nos. 5,436,392 and 5,489,520 and many others]. For purposes herein, when introducing a MAC, microinjection, protoplast fusion and particle gun bombardment are preferred.

Plant species, including tobacco, rice, maize, rye, soybean, *Brassica napus*, cotton, lettuce, potato and tomato, have been used to produce transgenic plants. Tobacco and other species, such as petunias, often serve as experimental models in which the methods have been developed and the genes first introduced and expressed.

DNA uptake can be accomplished by DNA alone or in the presence of PEG, which is a fusion agent, with plant protoplasts or by any variations of such methods known to those of skill in the art [see, e.g., U.S. Pat. No. 4,684,611 to Schilperoot et al.]. Electroporation, which involves high-voltage electrical pulses to a solution containing a mixture of protoplasts and foreign DNA to create reversible pores, has been used, for example, to successfully introduce foreign genes into rice and *Brassica napus*. Microinjection of DNA into plant cells, including cultured cells and cells in intact plant organs and embryoids in tissue culture and microprojectile bombardment [acceleration of small high density particles, which contain the DNA, to high velocity with a particle gun apparatus, which forces the particles to penetrate plant cell walls and membranes] have also been used. All plant cells into which DNA can be introduced and that can be regenerated from the transformed cells can be used to produce transformed whole plants which contain the transferred artificial chromosome. The particular protocol and means for introduction of the DNA into the plant host may need to be adapted or refined to suit the particular plant species or cultivar.

c. Insect cells

Insects are useful hosts for introduction of artificial chromosomes for numerous reasons, including, but not limited to: (a) amplification of genes encoding useful proteins can be accomplished in the artificial chromosome to obtain higher protein yields in insect cells; (b) insect cells support required post-translational modifications, such as glycosylation and phosphorylation, that can be required for protein biological functioning; (c) insect cells do not support mammalian viruses, and, thus, eliminate the problem of cross-contamination of products with such infectious agents; (d) this technology circumvents traditional recombinant baculovirus systems for production of nutritional, industrial or medicinal proteins in insect cell systems; (e) the low temperature optimum for insect cell growth (28° C.) permits reduced energy cost of production; (f) serum-free growth medium for insect cells permits lower production costs; (g) artificial chromosome-containing cells can be stored indefinitely at low temperature; and (h) insect larvae will be biological factories for production of nutritional, medicinal or industrial proteins by microinjection of fertilized insect eggs [see, eq., Joy et al. (1991) Current Science 66:145–150, which provides a method for microinjecting heterologous DNA into Bombyx mori eggs].

Either MACs or insect-specific artificial chromosomes [BUGACs] will be used to introduce genes into insects. As described in the Examples, it appears that MACs will function in insects to direct expression of heterologous DNA contained thereon. For example, as described in the Examples, a MAC containing the B. mori actin gene promoter fused to the lacZ gene has been generated by transfection of EC3/7C5 cells with a plasmid containing the fusion gene. Subsequent fusion of the B. mori cells with the transfected EC3/7C5 cells that survived selection yielded a MAC-containing insect-mouse hybrid cell line in which, β-galactosidase expression was detectable.

Insect host cells include, but are not limited to, hosts such as Spodoptera frugiperda [caterpillar], Aedes aegypti [mosquito], Aedes albopictus [mosquito], Drosphila melanogaster [fruitfly], Bombyx mori [silkworm], Manduca sexta [tomato horn worm] and Trichoplusia ni [cabbage looper]. Efforts have been directed toward propagation of insect cells in culture. Such efforts have focused on the fall armyworm, Spodoptera frugiperda. Cell lines have been developed also from other insects such as the cabbage looper, Trichoplusia ni and the silkworm, Bombyx mori. It has also been suggested that analogous cell lines can be created using the tomato hornworm, Manduca sexta. To introduce DNA into an insect, it should be introduced into the larvae, and allowed to proliferate, and then the hemolymph recovered from the larvae so that the proteins can be isolated therefrom.

The preferred method herein for introduction of artificial chromosomes into insect cells is microinjection [see, e.g., Tamura et al. (1991) Bio Ind. 8:26–31; Nikolaev et al. (1989) Mol. Biol. (Moscow) 23:1177–87; and methods exemplified and discussed herein].

D. Applications for and Uses of Artificial chromosomes

Artificial chromosomes provide convenient and useful vectors, and in some instances [e.g., in the case of very large heterologous genes] the only vectors, for introduction of heterologous genes into hosts. Virtually any gene of interest is amenable to introduction into a host via artificial chromosomes. Such genes include, but are not limited to, genes that encode receptors, cytokines, enzymes, proteases, hormones, growth factors, antibodies, tumor suppressor genes, therapeutic products and multigene pathways.

The artificial chromosomes provided herein will be used in methods of protein and gene product production, particularly using insects as host cells for production of such products, and in cellular (e.g., mammalian cell) production systems in which the artificial chromomsomes (particularly MACs) provide a reliable, stable and efficient means for optimizing the biomanufacturing of important compounds for medicine and industry. They are also intended for use in methods of gene therapy, and in for production of transgenic plants and animals [discussed above, below and in the EXAMPLES].

1. Gene Therapy

Any nucleic acid encoding a therapeutic gene product or product of a multigene pathway may be introduced into a host animal, such as a human, or into a target cell line for introduction into an animal, for therapeutic purposes. Such therapeutic purposes include, genetic therapy to cure or to provide gene products that are missing or defective, to deliver agents, such as anti-tumor agents, to targeted cells or to an animal, and to provide gene products that will confer resistance or reduce susceptibility to a pathogen or ameliorate symptoms of a disease or disorder. The following are some exemplary genes and gene products. Such exemplification is not intended to be limiting.

a. Anti-HIV ribozymes

As exemplified below, DNA encoding anti-HIV ribozymes can be introduced and expressed in cells using MACs, including the euchromatin-based minichromosomes and the SATACs. These MACs can be used to make a transgenic mouse that expresses a ribozyme and, thus, serves as a model for testing the activity of such ribozymes or from which ribozyme-producing cell lines can be made. Also, introduction of a MAC that encodes an anti-HIV ribozyme into human cells will serve as treatment for HIV infection. Such systems further demonstrate the viability of using any disease-specific ribozyme to treat or ameliorate a particular disease.

b. Tumor Suppressor Genes

Tumor suppressor genes are genes that, in their wild-type alleles, express proteins that suppress abnormal cellular proliferation. When the gene coding for a tumor suppressor protein is mutated or deleted, the resulting mutant protein or the complete lack of tumor suppressor protein expression may result in a failure to correctly regulate cellular proliferation. Consequently, abnormal cellular proliferation may take place, particularly if there is already existing damage to the cellular regulatory mechanism. A number of well-studied human tumors and tumor cell lines have been shown to have missing or nonfunctional tumor suppressor genes.

Examples of tumor suppression genes include, but are not limited to, the retinoblastoma susceptibility gene or RB gene, the p53 gene, the gene that is deleted in colon carcinoma [i.e., the DCC gene] and the neurofibromatosis type 1 [NF-1] tumor suppressor gene [see, e.g., U.S. Pat. No. 5,496,731; Weinberg et al. (1991) 254:1138–1146]. Loss of function or inactivation of tumor suppressor genes may play a central role in the initiation and/or progression of a significant number of human cancers.

The p53 Gene

5 Somatic cell mutations of the p53 gene are said to be the most frequent of the gene mutations associated with human cancer [see, e.g., Weinberg et al. (1991) Science 254:1138–1146]. The normal or wild-type p53 gene is a negative regulator of cell growth, which, when damaged, favors cell transformation. The p53 expression product is found in the nucleus, where it may act in parallel or cooperatively with other gene products. Tumor cell lines in which p53 has been deleted have been successfully treated with wild-type p53 vector to reduce tumorigenicity [see, Baker et al. (1990) Science 249:912–915].

DNA encoding the p53 gene and plasmids containing this DNA are well known [see, e.g., U.S. Pat. No. 5,260,191; see, also Chen et al. (1990) Science 250:1576; Farrel et al. (1991) EMBO J. 10:2879–2887; plasmids containing the gene are available from the ATCC, and the sequence is in the GenBank Database, accession nos. X54156, X60020, M14695, M16494, K03199].

c. The CFTR gene

Cystic fibrosis [CF] is an autosomal recessive disease that affects epithelia of the airways, sweat glands, pancreas, and other organs. It is a lethal genetic disease associated with a defect in chloride ion transport, and is caused by mutations in the gene coding for the cystic fibrosis transmembrane conductance regulator [CFTRI, a 1480 amino acid protein that has been associated with the expression of chloride conductance in a variety of eukaryotic cell types. Defects in CFTR destroy or reduce the ability of epithelial cells in the airways, sweat glands, pancreas and other tissues to transport chloride ions in response to cAMP-mediated agonists and impair activation of apical membrane channels by cAMP-dependent protein kinase A [PKA]. Given the high incidence and devastating nature of this disease, development of effective CF treatments is imperative.

The CFTR gene [~250 kb] can be transferred into a MAC for use, for example, in gene therapy as follows. A CF-YAC [see Green et al. *Science* 250:94–98] may be modified to include a selectable marker, such as a gene encoding a protein that confers resistance to puromycin or hygromycin, and λ-DNA for use in site-specific integration into a neo-minichromosome or a SATAC. Such a modified CF-YAC can be introduced into MAC-containing cells, such as EC3/7C5 or 19C5xHa4 cells, by fusion with yeast protoplasts harboring the modified CF-YAC or microinjection of yeast nuclei harboring the modified CF-YAC into the cells. Stable transformants are then selected on the basis of antibiotic resistance. These transformants will carry the modified CF-YAC within the MAC contained in the cells.

2. Animals, birds, fish and plants that are genetically altered to possess desired traits such as resistance to disease Artificial chromosomes are ideally suited for preparing animals, including vertebrates and invertebrates, including birds and fish as well as mammals, that possess certain desired traits, such as, for example, disease resistance, resistance to harsh environmental conditions, altered growth patterns, and enhanced physical characteristics.

One example of the use of artificial chromosomes in generating disease-resistant organisms involves the preparation of multivalent vaccines. Such vaccines include genes encoding multiple antigens that can be carried in a MAC, or species-specific artificial chromosome, and either delivered to a host to induce immunity, or incorporated into embryos to produce transgenic animals and plants that are immune or less susceptible to certain diseases.

Disease-resistant animals and plants may also be prepared in which resistance or decreased susceptibility to disease is conferred by introduction into the host organism or embryo of artificial chromosomes containing DNA encoding gene products (e.g., ribozymes and proteins that are toxic to certain pathogens) that destroy or attenuate pathogens or limit access of pathogens to the host.

Animals and plants possessing desired traits that might, for example, enhance utility, processibility and commercial value of the organisms in areas such as the agricultural and ornamental plant industries may also be generated using artificial chromosomes in the same manner as described above for production of disease-resistant animals and plants. In such instances, the artificial chromosomes that are introduced into the organism or embryo contain DNA encoding gene products that serve to confer the desired trait in the organism.

Birds, particularly fowl such as chickens, fish and crustaceans will serve as model hosts for production of genetically altered organisms using artificial chromosomes.

3. Use of MACs and other artificial chromosomes for preparation and screening of libraries Since large fragments of DNA can be incorporated into each artificial chromosome, the chromosomes are well-suited for use as cloning vehicles that can accommodate entire genomes in the preparation of genomic DNA libraries, which then can be readily screened. For example, MACs may be used to prepare a genomic DNA library useful in the identification and isolation of functional centromeric DNA from different species of organisms. In such applications, the MAC used to prepare a genomic DNA library from a particular organism is one that is not functional in cells of that organism. That is, the MAC does not stably replicate, segregate or provide for expression of genes contained within it in cells of the organism. Preferably, the MACs contain an indicator gene (e.g., the lacZ gene encoding β-galactosidase or genes encoding products that confer resistance to antibiotics such as neomycin, puromycin, hygromycin) linked to a promoter that is capable of promoting transcription of the indicator gene in cells of the organism. Fragments of genomic DNA from the organism are incorporated into the MACs, and the MACs are transferred to cells from the organism. Cells that contain MACs that have incorporated functional centromeres contained within the genomic DNA fragments are identified by detection of expression of the marker gene.

4. Use of MACs and other artificial chromosomes for stable, high-level protein production Cells containing the MACs and/or other artificial chromosomes provided herein are advantageously used for production of proteins, particularly several proteins from one cell line, such as multiple proteins involved in a biochemical pathway or multivalent vaccines. The genes encoding the proteins are introduced into the artificial chromosomes which are then introduced into cells. Alternatively, the heterologous gene(s) of interest are transferred into a production cell line that already contains artificial chromosomes in a manner that targets the gene(s) to the artificial chromosomes. The cells are cultured under conditions whereby the heterologous proteins are expressed. Because the proteins will be expressed at high levels in a stable permanent extra-genomic chromosomal system, selective conditions are not required.

Any transfectable cells capable of serving as recombinant hosts adaptable to continuous propagation in a cell culture system [see, e.g., McLean (1993) *Trends In Biotech.* 1 1 :232–238] are suitable for use in an artificial chromosome-based protein production system. Exemplary host cell lines include, but are not limited to, the following: Chinese hamster ovary (CHO) cells [see, e.g., Zang et al. (1995) *Biotechnology* 13:389–392], HEK 293, Ltk-, COS-7, DG44, and BHK cells. CHO cells are particularly preferred host cells. Selection of host cell lines for use in artificial chromosome-based protein production systems is within the skill of the art, but often will depend on a variety of factors, including the properties of the heterologous protein to be produced, potential toxicity of the protein in the host cell, any requirements for post-translational modification (e.g., glycosylation, amination, phosphorylation) of the protein, transcription factors available in the cells, the type of promoter element(s) being used to drive expression of the heterologous gene, whether production will be completely intracellular or the heterologous protein will preferably be secreted from the cell, and the types of processing enzymes in the cell.

The artificial chromosome-based system for heterologous protein production has many advantageous features. For example, as described above, because the heterologous DNA is located in an independent, extra-genomic artificial chromosome (as opposed to randomly inserted in an unknown area of the host cell genome or located as extrachromosomal element(s) providing only transient expression) it is stably maintained in an active transcription unit and is not subject to ejection via recombination or elimination during cell division. Accordingly, it is unnecessary to include a selection gene in the host cells and thus growth under selective conditions is also unnecessary. Furthermore, because the artificial chromosomes are capable of incorporating large segments of DNA, multiple copies of the heterologous gene and linked promoter element(s) can be retained in the chromosomes, thereby providing for high-level expression of the foreign protein(s). Alternatively, multiple copies of the gene can be linked to a single promoter element and several different genes may be linked in a fused polygene complex to a single promoter for expression of, for example, all the key proteins constituting a complete metabolic pathway [see, e.g., Beck von Bodman et al. (1995) *Biotechnology* 13:587–591]. Alternatively, multiple copies of a single gene can be operatively linked to a single promoter, or each or one or several copies may be linked to different promoters or multiple copies of the same promoter. Additionally, because artificial chromosomes have an almost unlimited capacity for integration and expression of foreign genes, they can be used not only for the expression of genes encoding end-products of interest, but also for the expression of genes associated with optimal maintenance and metabolic management of the host cell, e.g., genes encoding growth factors, as well as genes that may facilitate rapid synthesis of correct form of the desired heterologous protein product, e.g., genes encoding processing enzymes and transcription factors.

The MACS are suitable for expression of any proteins or peptides, including proteins and peptides that require in vivo posttranslational modification for their biological activity. Such proteins include, but are not limited to antibody fragments, full-length antibodies, and multimeric antibodies, tumor suppressor proteins, naturally occurring or artificial antibodies and enzymes, heat shock proteins, and others.

Thus, such cell-based "protein factories" employing MACs can generated using MACs constructed with multiple copies [theoretically an unlimited number or at least up to a number such that the resulting MAC is about up to the size of a genomic chromosome] of protein-encoding genes with appropriate promoters, or multiple genes driven by a single promoter, i.e., a fused gene complex [such as a complete metabolic pathway in plant expression system; see, e.g., Beck von Bodman (1995) *Biotechnology* 13:587–591]. Once such MAC is constructed, it can be transferred to a suitable cell culture system, such as a CHO cell line in protein-free culture medium [see, e.g., (1995) *Biotechnology* 13:389–39] or other immortalized cell lines [see, e.g., (1993) *TIBTECH* 11:232–238] where continuous production can be established.

The ability of MACs to provide for high-level expression of heterologous proteins in host cells is demonstrated, for example, by analysis of the H1D3 and G3D5 cell lines described herein and deposited with the ECACC. Northern blot analysis of mRNA obtained from these cells reveals that expression of the hygromycin-resistance and β-galactosidase genes in the cells correlates with the amplicon number of the megachromosome(s) contained therein.

The following examples are included for illustrative purposes only and are not intended to limit the scope of the invention.

EXAMPLE 1

General Materials and Methods

The following materials and methods are exemplary of methods that are used in the following Examples and that can be used to prepare cell lines containing artificial chromosomes. Other suitable materials and methods known to those of skill in the art may used. Modifications of these materials and methods known to those of skill in the art may also be employed.

A. Culture of cell lines, cell fusion, and transfection of cells

1. Chinese hamster K-20 cells and mouse A9 fibroblast cells were cultured in F-12 medium. EC3/7 [see, U.S. Pat. No. 5,288,625, and deposited at the European Collection of Animal cell Culture (ECACC) under accession no. 90051001; see, also Hadlaczky et al. (1991) *Proc. Natl. Acad. Sci. U.S.A.* 88:8106–8110 and U.S. application Ser. No. 08/375,271] and EC3/7C5 [see, U.S. Pat. No. 5,288,625 and Praznovszky et al. (1991) *Proc. Natl. Acad. Sci. U.S.A.* 88:11042–11046] mouse cell lines, and the KE1–2/4 hybrid cell line were maintained in F-1 2 medium containing 400 μg/ml G418 [SIGMA, St. Louis, Mo.].

2. TF1004G 19 and TF1004G-19C5 mouse cells, described below, and the 19C5xHa4 hybrid, described below, and its sublines were cultured in F-1 2 medium containing up to 400 μg/ml Hygromycin B [Calbiochem]. LP1 1 cells were maintained in F-12 medium containing 3–15 μg/ml Puromycin [SIGMA, St. Louis, Mo.].

3. Cotransfection of EC3/7C5 cells with plasmids [pH 132, pCH 110 available from Pharmacia, see, also Hall et al. (1983) *J. Mol. Appl. Gen.* 2:101–109] and with λ DNA was conducted using the calcium phosphate DNA precipitation method [see, eg., Chen et al. (1987) *Mol. Cell. Biol.* 7:2745–2752], using 2–5 μg plasmid DNA and 20 μg λ phage DNA per $5 \times 10^6$ recipient cells.

4. Cell fusion

Mouse and hamster cells were fused using polyethylene glycol [Davidson et al. (1976) *Som. Cell Genet.* 2:165–176]. Hybrid cells were selected in HAT medium containing 400 μg/ml Hygromycin B.

Approximately $2 \times 10^7$ recipient and $2 \times 10^6$ donor cells were fused using polyethylene glycol [Davidson et al. (1976) *Som. Cell Genet.* 2:165–176]. Hybrids were selected and maintained in F-12/HAT medium [Szybalsky et al. (1962) *Natl. Cancer Inst. Monoqr.* 7:75–89] containing 10% FCS and 400 μg/ml G418. The presence of "parental"] chromosomes in the hybrid cell lines was verified by in situ hybridization with species-specific probes using biotin-labeled human and hamster genomic DNA, and a mouse long interspersed repetitive DNA [pMCPE1.51].

5. Microcell fusion

Microcell-mediated transfer of artificial chromosomes from EC3/7C5 cells to recipient cells was done according to Saxon et al. [(1985) *Mol. Cell. Biol.* 1:140–146] with the modifications of Goodfellow et al. [(1989) Techniques for mammalian genome transfer. In *Genome Analysis a Practical Approach.* K. E. Davies, ed., IRL Press, Oxford, Washington D.C. pp.1–17] and Yamada et al. [(1990) *Oncogene* 5:1141–1147]. Briefly, $5 \times 10^6$ EC3/7C5 cells in a T25 flask were treated first with 0.05 μg/ml colcemid for 48 hr and then with 10 μg/ml cytochalasin B for 30 min. The T25 flasks were centrifuged on edge and the pelleted microcells were suspended in serum free DME medium. The microcells were filtered through first a 5 micron and then a 3 micron polycarbonate filter, treated with 50 μg/ml of phytohemagglutin, and used for polyethylene glycol mediated fusion with recipient cells. Selection of cells containing the MMCneo was started 48 hours after fusion in medium containing 400–800 μg/ml G418.

Microcells were also prepared from 1B3 and GHB42 donor cells as follows in order to be fused with E2D6K cells

[a CHO K-20 cell line carrying the puromycin N-acetyltransferase gene, i.e., the puromycin resistance gene, under the control of the SV40 early promoter]. The donor cells were seeded to achieve 60–75% confluency within 24–36 hours. After that time, the cells were arrested in mitosis by exposure to colchicine (10 μg/ml) for 12 or 24 hours to induce micronucleation. To promote micronucleation of GHB42 cells, the cells were exposed to hypotonic treatment (10 min at 37° C.). After colchicine treatment, or after colchicine and hypotonic treatment, the cells were grown in colchicine-free medium.

The donor cells were trypsinized and centrifuged and the pellets were suspended in a 1:1 Percoll medium and incubated for 30–40 min at 37° C. After the incubation, 1–3×10$^7$ cells (60–70% micronucleation index) were loaded onto each Percoll gradient (each fusion was distributed on 1–2 gradients). The gradients were centrifuged at 19,000 rpm for 80 min in a Sorvall SS-34 rotor at 34–37° C. After centrifugation, two visible bands of cells were removed, centrifuged at 2000 rpm, 10 min at 4° C., resuspended and filtered through 8 μm pore size nucleopore filters.

The microcells prepared from the 1B3 and GHB42 cells were fused with E2D6K. The E2D6K cells were generated by CaPO$_4$ transfection of CHO K-20 cells with pCHTV2. Plasmid pCHTV2 contains the puromycin-resistance gene linked to the SV40 promoter and polyadenylation signal, the *Saccharomyces cerevisiae URA*3 gene, 2.4- and 3.2-kb fragments of a Chinese hamster chromosome 2-specific satellite DNA (HC-2 satellite; see Fatyol et al. (1994) *Nuc. Acids Res.* 22:3728–3736), two copies of the diptheria toxin-A chain gene (one linked to the herpes simplex virus thymidine kinase (HSV-TK) gene promoter and SV40 polyadenylation signal and the other linked to the HSV-TK promoter without a polyadenylation signal), the ampicillin-resistance gene and the ColE1 origin of replication. Following transfection, puromycin-resistant colonies were isolated. THe presence of the pCHTV2 plasmid in the E2D6K cell line was confirmed by nucleic acid amplification of DNA isolated from the cells.

The purified microcells were centrifuged as described above and resuspended in 2 ml of phytohemagglutinin-P (PHA-P, 100 μg/ml). The microcell suspension was then added to a 60–70% confluent recipient culture of E2D6K cells. The preparation was incubated at room temperature for 30–40 min to agglutinate the microcells. After the PHA-P was removed, the cells were incubated with 1 ml of 50% polyethyleneglycol (PEG) for one min. The PEG was removed and the culture was washed three times with F-12 medium without serum. The cells were incubated in non-selective medium for 48–60 hours. After this time, the cell culture was trypsinized and plated in F-12 medium containing 400 μg/ml hygromycin B and 10 g/ml puromycin to select against the parental cell lines.

Hybrid clones were isolated from the cells that had been cultured in selective medium. These clones were then analyzed for expression of β-galactosidase by the X-gal staining method. Four of five hybrid clones analyzed that had been generated by fusion of GHB42 microcells with E2D6K cells yielded positive staining results indicating expression of β-galactosidase from the lacZ gene contained in the megachromosome contributed by the GHB42 cells. Similarly, a hybrid clone that had been generated by fusion of 1 B3 microcells with E2D6K cells yielded positive staining results indicating expression of β-galactosidase from the lacZ gene contained in the megachromosome contributed by the 1 B3 cells. In situ hybridization analysis of the hybrid clones is also performed to analyze the mouse chromosome content of the mouse-hamster hybrid cells.

B. Chromosome banding

Trypsin G-banding of chromosomes was performed using the method of Wang & Fedoroff [(1972) *Nature* 235:52–54], and the detection of constitutive heterochromatin with the BSG. C-banding method was done according to Sumner [(1972) *Exp. Cell Res.* 75:304–306]. For the detection of chromosome replication by bromodeoxyuridine [BrdU] incorporation, the Fluorescein Plus Giemsa [FPG] staining method of Perry & Wolff [(1974) *Nature* 251:156–158] was used.

C. Immunolabelling of chromosomes and in situ hybridization

Indirect immunofluorescence labelling with human anti-centromere serum LU851 [Hadlaczkyetal. (1986) *Exp. Cell Res.* 167:1–15], and indirect immunofluorescence and in situ hybridization on the same preparation were performed as described previously [see, Hadlaczky et al. (1991) *Proc. Natl. Acad. Sci. U.S.A.* 88:8106–8110, see, also U.S. application Ser. No. 08/375,271]. Immunolabelling with fluorescein-conjugated anti-BrdU monoclonal antibody [Boehringer] was performed according to the procedure recommended by the manufacturer, except that for treatment of mouse A9 chromosomes, 2 M hydrochloric acid was used at 37° C. for 25 min, and for chromosomes of hybrid cells, 1 M hydrochloric acid was used at 37° C. for 30 min.

D. Scanning electron microscopy

Preparation of mitotic chromosomes for scanning electron microscopy using osmium impregnation was performed as described previously [Sumner (1991) *Chromosoma* 100:410–418]. The chromosomes were observed with a Hitachi S-800 field emission scanning electron microscope operated with an accelerating voltage of 25 kV.

E. DNA manipulations, plasmids and probes

1. General methods

All general DNA manipulations were performed by standard procedures [see, e.g., Sambrook et al. (1989) *Molecular cloning: A Laboratory Manual* Cold Spring Harbor Laboratory Press, Cold Spring Harbor, N.Y.]. The mouse major satellite probe was provided by Dr. J. B. Rattner [University of Calgary, Alberta, Canada]. Cloned mouse satellite DNA probes [see Wong et al. (1988) *Nucl. Acids Res.* 16:11645–11661], including the mouse major satellite probe, were gifts from Dr. J. B. Rattner, University of Calgary. Hamster chromosome painting was done with total hamster genomic DNA, and a cloned repetitive sequence specific to the centromeric region of chromosome 2 [Fatyol et al. (1994) *Nucl. Acids Res.* 22:3728–3736] was also used. Mouse chromosome painting was done with a cloned long interspersed repetitive sequence [pMCP1.51] specific for the mouse euchromatin.

For cotransfection and for in situ hybridization, the pCH 110, β-galactosidase construct [Pharmacia or Invitrogen], and λcl 875 Sam7 phage DNA [New England Biolabs] were used.

2. Construction of Plasmid pPuroTel

Plasmid pPuroTel, which carries a Puromycin-resistance gene and a cloned 2.5 kb human telomeric sequence [see SEQ ID No. 3], was constructed from the pBabe-puro retroviral vector [Morgenstern et al. (1990) *Nucl. Acids Res.* 18:3587–3596; provided by Dr. L. Székely (Microbiology and Tumorbiology Center, Karolinska Institutet, Stockholm); see, also Tonghua et al. (1995) *Chin. Med. J.* (Beijing, Engl. Ed.) 108:653–659; Couto et al. (1994) *Infect. Immun.* 62:2375–2378; Dunckley et al. (1992) *FEBS Lett.* 296:128–34; French et al. (1995) *Anal. Biochem.* 228:354–355; Liu et al. (1995) *Blood* 85:1095–1103; International PCT application Nos. WO 9520044; WO 9500178, and WO 9419456].

F. Deposited cell lines

Cell lines KE1-2/4, EC3/7C5, TF1004G19C5, 19C5xHa4, G3D5 and H1D3 have been deposited in accord with the Budapest Treaty at the European Collection of Animal Cell Culture (ECACC) under Accession Nos. 96040924, 96040925, 96040926, 96040927, 96040928 and 96040929, respectively. The cell lines were deposited on Apr. 9, 1996, at the European Collection of Animal Cell Cultures (ECACC) Vaccine Research and Production Laboratory, Public Health Laboratory Service, Centre for Applied Microbiology and Research, Porton Down, Salisbury, Wiltshire SP4 OJG, United Kingdom.

EXAMPLE 2

Preparation of EC3/7, EC3/7C5 and related cell lines

The EC3/7 cell line is an LMTK- mouse cell line that contains the neo-centromere. The EC3/7C5 cell line is a single-cell subclone of EC3/7 that contains the neo-minichromosome.

A. EC3/7 Cell line

As described in U.S. Pat. No. 5,288,625 [see, also Praznovszky etal. (1991) *Proc. Natl. Acad. Sci. U.S.A.* 88:11042–11046 and Hadlaczky etal. (1991) *Proc. Natl. Acad. Sci. U.S.A.* 88:8106–8110] de novo centromere formation occurs in a transformed mouse LMTK$^-$ fibro-blast cell line [EC3/7] after cointegration of A constructs [ACM8 and λgtWESneo] carrying human and bacterial DNA.

By cotransfection of a 14 kb human DNA fragment cloned in A [λCM8] and a dominant marker gene [λgtWESneo], a selectable centromere linked to a dominant marker gene [neo-centromere] was formed in mouse LMTK$^-$ cell line EC3/7 [Hadlaczky et al. (1991) *Proc. Natl. Acad. Sci. U.S.A.* 88:8106–8110, see FIG. 1]. Integration of the heterologous DNA [the λ DNA and marker gene-encoding DNA] occurred into the short arm of an acrocentric chromosome [chromosome 7 (see, FIG. 1B)], where an amplification process resulted in the formation of the new centromere [neo-centromere (see FIG. 1C)]. On the dicentric chromosome (FIG. 1C), the newly formed centromere region contains all the heterologous DNA (human, λ, and bacterial) introduced into the cell and an active centromere.

Having two functionally active centromeres on the same chromosome causes regular breakages between the centromeres [see, FIG. 1E]. The distance between the two centromeres on the dicentric chromosome is estimated to be ~10–15 Mb, and the breakage that separates the minichromosome occurred between the two centromeres. Such specific chromosome breakages result in the appearance [in approximately 10% of the cells] of a chromosome fragment that carries the neo-centromere [FIG. 1F]. This chromosome fragment is principally composed of human, λ, plasmid, and neomycin-resistance gene DNA, but it also has some mouse chromosomal DNA. Cytological evidence suggests that during the stabilization of the MMCneo, there was an inverted duplication of the chromosome fragment bearing the neo-centromere. The size of minichromosomes in cell lines containing the MMCneo is approximately 20–30 Mb; this finding indicates a two-fold increase in size.

From the EC3/7 cell line, which contains the dicentric chromosome [FIG. 1E], two sublines [EC3/7C5 and EC3/7C6] were selected by repeated single-cell cloning. In these cell lines, the neo-centromere was found exclusively on a small chromosome [neo-minichromosome], while the formerly dicentric chromosome carried detectable amounts of the exogenously-derived DNA sequences but not an active neo-centromere [FIGS. 1F and 1G].

The minichromosomes of cell lines EC3/7C5 and EC3/7C6 are similar. No differences are detected in their architectures at either the cytological or molecular level. The minichromosomes were indistinguishable by conventional restriction endonuclease mapping or by long-range mapping using pulsed field electrophoresis and Southern hybridization. The cytoskeleton of cells of the EC3/7C6 line showed an increased sensitivity to colchicine, so the EC3/7C5 line was used for further detailed analysis.

B. Preparation of the EC3/7C5 and EC3/7C6 cell lines

The EC3/7C5 cells, which contain the neo-minichromosome, were produced by subcloning the EC3/7 cell line in high concentrations of G418 [40-fold the lethal dose] for 350 generations. Two single cell-derived stable cell lines [EC3/7C5 and EC3/7C6] were established. These cell lines carry the neo-centromere on minichromosomes and also contain the remaining fragment of the dicentric chromosome. Indirect immunofluorescence with anti-centromere antibodies and subsequent in situ hybridization experiments demonstrated that the minichromosomes derived from the dicentric chromosome. In EC3/7C5 and EC3/7C6 cell lines (140 and 128 metaphases, respectively) no intact dicentric chromosomes were found, and minichromosomes were detected in 97.2% and 98.1% of the cells, respectively. The minichromosomes have been maintained for over 150 cell generations. They do contain the remaining portion of the formerly dicentric chromosome.

Multiple copies of telomeric DNA sequences were detected in the marker centromeric region of the remaining portion of the formerly dicentric chromosome by in situ hybridization. This indicates that mouse telomeric sequences were coamplified with the foreign DNA sequences. These stable minichromosome-carrying cell lines provide direct evidence that the extra centromere containing human DNA is functioning and is capable of maintaining the minichromosomes [see, U.S. Pat. No. 5,288,625].

The chromosome breakage in the EC3/7 cells, which separates the neo-centromere from the mouse chromosome, occurred in the G-band positive "foreign" DNA region. This is supported by the observation of traces of λ and human DNA sequences at the broken end of the formerly dicentric chromosome. Comparing the G-band pattern of the chromosome fragment carrying the neo-centromere with that of the stable neo-minichromosome, reveals that the neo-minichromosome is an inverted duplicate of the chromosome fragment that bears the neo-centromere. This is also evidenced by the observation that although the neo-minichromosome carries only one functional centromere, both ends of the minichromosome are heterochromatic, and mouse satellite DNA sequences were found in these heterochromatic regions by in situ hybridization.

These two cell lines, EC3/7C5 and EC3/7C6, thus carry a selectable mammalian minichromosome [MMCneo] with a centromere linked to a dominant marker gene [Hadlaczky et al. (1991) *Proc. Natl. Acad. Sci. U.S.A.* 88:8106–8110]. MMCneo is intended to be used as a vector for minichromosome-mediated gene transfer and has been used as model of a minichromosome-based vector system.

Long range mapping studies of the MMCneo indicated that human DNA and the neomycin-resistance gene constructs integrated into the mouse chromosome separately, followed by the amplification of the chromosome region that contains the exogenous DNA. The MMCneo contains about 30–50 copies of the λCM8 and λgtWESneo DNA in the form of approximately 160 kb repeated blocks, which together cover at least a 3.5 Mb region. In addition to these, there are mouse telomeric sequences [Praznovszky et al. (1991) *Proc. Natl. Acad. Sci. U.S.A.* 88:11042–11046] and any DNA of mouse origin necessary for the correct higher-ordered structural organization of chromatids.

Using a chromosome painting probe mCPE1.51 [mouse long interspersed repeated DNA], which recognizes exclusively euchromatic mouse DNA, detectable amounts of interspersed repeat sequences were found on the MMCneo by in situ hybridization. The neo-centromere is associated with a small but detectable amount of satellite DNA. The chromosome breakage that separates the neo-centromere from the mouse chromosome occurs in the "foreign" DNA region. This is demonstrated by the presence of A and human DNA at the broken end of the formerly dicentric chromosome. At both ends of the MMCneo, however, there are traces of mouse major satellite DNA as evidenced by in situ hybridization. This observation suggests that the doubling in size of the chromosome fragment carrying the neo-centromere during the stabilization of the MMCneo is a result of an inverted duplication. Although mouse telomere sequences, which coamplified with the exogenous DNA sequences during the neo-centromere formation, may provide sufficient telomeres for the MMCneo, the duplication could have supplied the functional telomeres for the minichromosome.

The nucleotide sequence of portions of the neo-minichromosomes was determined as follows. Total DNA was isolated from EC3/7C5 cells according to standard procedures. The DNA was subjected to nucleic acid amplification using the Expand Long Template PCR system [Boehringer Mannheim] according to the manufacturer's procedures. The amplification procedure required only a single 33-mer oligonucleotide primer corresponding to sequence in a region of the phage λ right arm, which is contained in the neo-minichromosome. The sequence of this oligonucleotide is set forth as the first 33 nucleotides of SEQ ID No. 13. Because the neo-minichromosome contains a series of inverted repeats of this sequence, the single oligonucleotide was used as a forward and reverse primer resulting in amplification of DNA positioned between sets of inverted repeats of the phage λ DNA. Three products were obtained from the single amplification reaction, which suggests that the sequence of the DNA located between different sets of inverted repeats may differ. In a repeating nucleic acid unit within an artificial chromosome, minor differences may be present and may occur during culturing of cells containing the artificial chromosome. For example, base pair changes may occur as well as integration of mobile genetic elements and deletions of repeated sequences.

Each of the three products was subjected to DNA sequence analysis. The sequences of the three products are set forth in SEQ ID Nos. 13, 14, and 15, respectively. To be certain that the sequenced products were amplified from the neo-minichromosome, control amplifications were conducted using the same primers on DNA isolated from negative control cell lines (mouse Ltk- cells) lacking minichromosomes and the formerly dicentric chromosome, and positive control cell lines [the mouse-hamster hybrid cell line GB43 generated by treating 19C5xHa4 cells (see FIG. 4) with BrdU followed by growth in G418-containing selective medium and retreatment with BrdU] containing the neo-minichromosome only. Only the positive control cell line yielded the three amplification products; no amplification product was detected in the negative control reaction. The results obtained in the positive control amplification also demonstrate that the neo-minichromosome DNA, and not the fragment of the formerly dicentric mouse chromosome, was amplified.

The sequences of the three amplification products were compared to those contained in the Genbank/EMBL database. SEQ ID Nos. 13 and 14 showed high (~96%) homology to portions of DNA from intracisternal A-particles from mouse. SEQ ID No. 15 showed no significant homology with sequences available in the database. All three of these sequences may be used for generating gene targeting vectors as homologous DNAs to the neo-minichromosome.

C. Isolation and partial purification of minichromosomes

Mitotic chromosomes of EC3/7C5 cells were isolated as described by Hadlaczky et al. [(1981) *Chromosoma* 81:537–555], using a glycine-hexylene glycol buffer system [Hadlaczky et al. (1982) *Chromosoma* 86:643–659]. Chromosome suspensions were centrifuged at 1,200×g for 30 minutes. The supernatant containing minichromosomes was centrifuged at 5,000×g for 30 minutes and the pellet was resuspended in the appropriate buffer. Partially purified minichromosomes were stored in 50% glycerol at $-_{20}$° C.

D. Stability of the MMCneo maintenance and neo expression

EC3/7C5 cells grown in non-selective medium for 284 days and then transferred to selective medium containing 400 μg/ml G418 showed a 96% plating efficiency (colony formation) compared to control cells cultured permanently in the presence of G418. Cytogenetic analysis indicated that the MMCneo is stably maintained at one copy per cell under selective and non-selective culture conditions. Only two metaphases with two MMCneo were found in 2,270 metaphases analyzed.

Southern hybridization analysis showed no detectable changes in DNA restriction patterns, and similar hybridization intensities were observed with a neo probe when DNA from cells grown under selective or non-selective culture conditions were compared.

Northern analysis of RNA transcripts from the neo gene isolated from cells grown under selective and non-selective conditions showed only minor and not significant differences. Expression of the neo gene persisted in EC3/7C5 cells maintained in F-12 medium free of G418 for 290 days under non-selective culture conditions. The long-term expression of the neo gene(s) from the minichromosome may be influenced by the nuclear location of the MMCneo. In situ hybridization experiments revealed a preferential peripheral location of the MMCneo in the interphase nucleus. In more than 60% of the 2,500 nuclei analyses, the minichromosome was observed at the perimeter of the nucleus near the nuclear envelope.

EXAMPLE 3

Minichromosome transfer and production of the A-neo-chromosome

A. Minichromosome transfer

The neo-minichromosome [referred to as MMCneo, FIG. 2C] has been used for gene transfer by fusion of minichromosome-containing cells [EC3/7C5 or EC3/7C6] with different mammalian cells, including hamster and human. Thirty-seven stable hybrid cell lines have been produced. All established hybrid cell lines proved to be true hybrids as evidenced by in situ hybridization using biotinylated human, and hamster genomic, or pMCPE1.51 mouse long interspersed repeated DNA probes for "chromosome painting". The MMCneo has also been successfully transferred into mouse A9, L929 and pluripotent F9 teratocarcinoma cells by fusion of microcells derived from EC3/7C5 cells. Transfer was confirmed by PCR, Southern blotting and in situ hybridization with minichromosome-specific probes. The cytogenetic analysis confirmed that, as expected for microcell fusion, a few cells [1–5%] received [or retained] the MMCneo.

These results demonstrate that the MMCneo is tolerated by a wide range of cells. The prokaryotic genes and the extra dosage for the human and λ sequences carried on the minichromosome seem to be not disadvantageous for tissue culture cells.

The MMCneo is the smallest chromosome of the EC3/7C5 genome and is estimated to be approximately 20–30 Mb, which is significantly smaller than the majority of the host cell (mouse) chromosomes. By virtue of the smaller size, minichromosomes can be partially purified from a suspension of isolated chromosomes by a simple differential centrifugation. In this way, minichromosome suspensions of 15–20% purity have been prepared. These enriched minichromosome preparations can be used to introduce, such as by microinjection or lipofection, the minichromosome into selected target cells. Target cells include therapeutic cells that can be use in methods of gene therapy, and also embryonic cells for the preparation of transgenic animals.

The MMCneo is capable of autonomous replication, is stably maintained in cells, and permits persistent expression of the neo gene(s), even after long-term culturing under non-selective conditions. It is a non-integrative vector that appears to occupy a territory near the nuclear envelope. Its peripheral localization in the nucleus may have an important role in maintaining the functional integrity and stability of the MMCneo. Functional compartmentalization of the host nucleus may have an effect on the function of foreign sequences. In addition, MMCneo contains megabases of λ DNA sequences that should serve as a target site for homologous recombination and thus integration of desired gene(s) into the MMCneo. It can be transferred by cell and microcell fusion, microinjection, electroporation, lipid-mediated carrier systems or chromosome uptake. The neo-centromere of the MMCneo is capable of maintaining and supporting the normal segregation of a larger 150–200 Mb Aneo-chromosome. This result demonstrates that the MMCneo chromosome should be useful for carrying large fragments of heterologous DNA.

B. Production of the Aneo-chromosome

In the hybrid cell line KE1-2/4 made by fusion of EC3/7 and Chinese hamster ovary cells [FIG 2], the separation of the neo-centromere from the dicentric chromosome was associated with a further amplification process. This amplification resulted in the formation of a stable chromosome of average size [i.e., the Aneo-chromosome; see, Praznovszky et al. (1991) Proc. Natl. Acad. Sci. U.S.A. 88:11042–11046]. The Aneo-chromosome carries a terminally located functional centromere and is composed of seven large amplicons containing multiple copies of λ, human, bacterial, and mouse DNA sequences [see FIG. 2]. The amplicons are separated by mouse major satellite DNA [Praznovszky et al. (1991) Proc. Natl. Acad. Sci. U.S.A. 88:11042–11046] which forms narrow bands of constitutive heterochromatin between the amplicons.

EXAMPLE 4
Formation of the "sausage chromosome" [SC]

The findings set forth in the above EXAMPLES demonstrate that the centromeric region of the mouse chromosome 7 has the capacity for large-scale amplification [other results indicate that this capacity is not unique to chromosome 7]. This conclusion is further supported by results from cotransfection experiments, in which a second dominant selectable marker gene and a non-selected marker gene were introduced into EC3/7C5 cells carrying the formerly dicentric chromosome 7 and the neo-minichromosome. The EC3/7C5 cell line was transformed with λ phage DNA, a hygromycin-resistance gene construct [pH132], and a β-galactosidase gene construct [pCH110]. Stable transformants were selected in the presence of high concentrations [400 μg/ml] Hygromycin B, and analyzed by Southern hybridization. Established transformant cell lines showing multiple copies of integrated exogenous DNA were studied by in situ hybridization to localize the integration site(s), and by LacZ staining to detect β-galactosidase expression.

A. Materials and methods

1. Construction of pH132

The pH 132 plasmid carries the hygromycin B resistance gene and the anti-HIV-1 gag ribozyme [see, SEQ ID NO. 6 for DNA sequence that corresponds to the sequence of the ribozyme] under control of the β-actin promoter. This plasmid was constructed from pHyg plasmid [Sugden et al. (1985) Mol. Cell. Biol. 5:410–413; a gift from Dr. A. D. Riggs, Beckman Research Institute, Duarte; see, also, e.g., U.S. Pat. No. 4,997,764], and from pPC-RAG1 2 plasmid [see, Chang et al. (1990) Clin Biotech 2:23–31; provided by Dr. J. J. Rossi, Beckman Research Institute, Duarte; see, also U.S. Pat. Nos. 5,272,262, 5,149,796 and 5,144,019, which describes the anti-HIV gag ribozyme and construction of a mammalian expression vector containing the ribozyme insert linked to the β-actin promoter and SV40 late gene transcriptional termination and polyA signals]. Construction of pPC-RAG12 involved insertion of the ribozyme insert flanked by BamHI linkers was into BamHI-digested pHβ-Apr-1gpt [see, Gunning et al. (1987) Proc. Natl. Acad. Sci. U.S.A. 84:4831–4835, see, also U.S. Pat. No. 5,144,019].

Plasmid pH132 was constructed as follows. First, pPC-RAG12 [described by Chang et al. (1990) Clin. Biotech. 2:23–31] was digested with BamHI to excise a fragment containing an anti-HIV ribozyme gene [referred to as ribozyme D by Chang et al. [(1990) Clin. Biotech. 2:23–31]; see also U.S. Pat. No. 5,144,019 to Rossi et al., particularly FIG. 4 of the patent] flanked by the human β-actin promoter at the 5' end of the gene and the SV40 late transcriptional termination and polyadenylation signals at the 3' end of the gene. As described by Chang et al. [(1990) Clin. Biotech. 2:23–31], ribozyme D is targeted for cleavage of the translational initiation region of the HIV gag gene. This fragment of pPC-RAG12 was subcloned into pBluescript-KS(+) [Stratagene, La Jolla, CA] to produce plasmid 132. Plasmid 132 was then digested with XhoI and EcoRI to yield a fragment containing the ribozyme D gene flanked by the β-actin promoter at the 5' end and the SV40 termination and polyadenylation signals at the 3' end of the gene. This fragment was ligated to the largest fragment generated by digestion of pHyg [Sugden et al. (1985) Mol. Cell. Biol. 5:410–413] with EcoRI and SalI to yield pH132. Thus, pH 132 is an ~9.3 kb plasmid containing the following elements: the β-actin promoter linked to an anti-HIV ribozyme gene followed by the SV40 termination and polyadenylation signals, the thymidine kinase gene promoter linked to the hygromycin-resistance gene followed by the thymidine kinase gene polyadenylation signal, and the E. coli ColE1 origin of replication and the ampicillin-resistance gene.

The plasmid pHyg [see, e.g., U.S. Pat. Nos. 4,997,764, 4,686,186 and 5,162,215], which confers resistance to hygromycin B using transcriptional controls from the HSV-1 tk gene, was originally constructed from pKan2 [Yates et al. (1984) *Proc. Natl. Acad. Sci. U.S.A.* 81:3806–3810] and pLG89 [see, Gritz et al. (1983) *Gene* 25:179–188]. Briefly pKan2 was digested with Smal and Bqlll to remove the sequences derived from transposon Tn5. The hygromycin-resistance hph gene was inserted into the digested pKan2 using blunt-end ligation at the Snal site and "sticky-end" ligation [using 1 Weiss unit of T4 DNA ligase (BRL) in 20 microliter volume] at the Bglll site. The Smal and Bglll sites of pKan2 were lost during ligation.

The resulting plasmid pH 132, produced from introduction of the anti-HIV ribozyme construct with promoter and polyA site into pHyg, includes the anti-HIV ribozyme under control of the β-actin promoter as well as the hygromycin-resistance gene under control of the TK promoter.

2. Chromosome banding

Trypsin G-banding of chromosomes was performed as described in EXAMPLE 1.

3. Cell cultures

TF1004G 19 and TF1004G-19C5 mouse cells and the 19C5xHa4 hybrid, described below, and its sublines were cultured in F-12 medium containing 400 $\mu$g/ml Hygromycin B [Calbiochem].

B. Cotransfection of EC3/7C5 to produce TF1004G19

Cotransfection of EC3/7C5 cells with plasmids [pH 132, pCH 110 available from Pharmacia, see, also Hall et al. (1983) *J. Mol. Appl. Gen.* 2:101–109] and with λ DNA [λcl 875 Sam 7(New England Biolabs)] was conducted using the calcium phosphate DNA precipitation method [see, e.g., Chen et al. (1987) *Mol. Cell. Biol.* 7:2745–2752], using 2–5 $\mu$g plasmid DNA and 20 $\mu$g λ phage DNA per $5 \times 10^6$ recipient cells.

C. Cell lines containing the sausage chromosome

Analysis of one of the transformants, designated TF1004G19, revealed that it has a high copy number of integrated pH 132 and pCH110 sequences, and a high level of β-galactosidase expression. G-banding and in situ hybridization with a human probe [CM8; see, eg., U.S. application Ser. No. 08/375,271] revealed unexpectedly that integration had occurred in the formerly dicentric chromosome 7 of the EC3/7C5 cell line. Furthermore, this chromosome carried a newly formed heterochromatic chromosome arm. The size of this heterochromatic arm varied between ~150 and ~800 Mb in individual metaphases.

By single cell cloning from the TF1004G19 cell line, a subclone TF1004G-19C5 [FIG 2D], which carries a stable chromosome 7 with a ~100–150 Mb heterochromatic arm [the sausage chromosome] was obtained. This cell line has been deposited in the ECACC under Accession No. 96040926. This chromosome arm is composed of four to five satellite segments rich in satellite DNA, and evenly spaced integrated heterologous "foreign" DNA sequences. At the end of the compact heterochromatic arm of the sausage chromosome, a less condensed euchromatic terminal segment is regularly observed. This subclone was used for further analyses.

D. Demonstration that the sausage chromosome is derived from the formerly dicentric chromosome In situ hybridization with λ phage and pH132 DNA on the TF1004G-19C5 cell line showed positive hybridization only on the minichromosome and on the heterochromatic arm of the "sausage" chromosome [FIG. 2D]. It appears that the "sausage" chromosome [herein also referred to as the SC] developed from the formerly dicentric chromosome (FD) of the EC3/7C5 cell line.

To establish this, the integration sites of pCH110 and pH132 plasmids were determined. This was accomplished by in situ hybridization on these cells with biotin-labeled subfragments of the hygromycin-resistance gene and the β-galactosidase gene. Both experiments resulted in narrow hybridizing bands on the heterochromatic arm of the sausage chromosome. The same hybridization pattern was detected on the sausage chromosome using a mixture of biotin-labeled λ probe and pH 132 plasmid, proving the cointegration of λ phages, pH132 and pCH110 plasmids.

To examine this further, the cells were cultured in the presence of the DNA-binding dye Hoechst 33258. Culturing of mouse cells in the presence of this dye results in under-condensation of the pericentric heterochromatin of metaphase chromosomes, thereby permitting better observation of the hybridization pattern. Using this technique, the heterochromatic arm of the sausage chromosome of TF1004G-19C5 cells showed regular under-condensation revealing the details of the structure of the "sausage" chromosome by in situ hybridization. Results of in situ hybridization on Hoechst-treated TF1004G-19C5 cells with biotin-labeled subfragments of hygromycin-resistance and β-galactosidase genes shows that these genes are localized only in the heterochromatic arm of the sausage chromosome. In addition, an equal banding hybridization pattern was observed. This pattern of repeating units [amplicons] clearly indicates that the sausage chromosome was formed by an amplification process and that the λ phage, pH132 and pCH110 plasmid DNA sequences border the amplicons.

In another series of experiments using fluorescence in situ hybridization [FISH] carried out with mouse major satellite DNA, the main component of the mouse pericentric heterochromatin, the results confirmed that the amplicons of the sausage chromosome are primarily composed of satellite DNA.

E. The sausage chromosome has one centromere

To determine whether mouse centromeric sequences had participated in the amplification process forming the "sausage" chromosome and whether or not the amplicons carry inactive centromeres, in situ hybridization was carried out with mouse minor satellite DNA. Mouse minor satellite DNA is localized specifically near the centromeres of all mouse chromosomes. Positive hybridization was detected in all mouse centromeres including the sausage chromosome, which, however, only showed a positive signal at the beginning of the heterochromatic arm.

Indirect immunofluorescence with a human anti-centromere antibody [LU 851] which recognizes only functional centromeres [see, e.g., Hadlaczky et al. (1989) *Chromosoma* 97:282–2881] proved that the sausage chromosome has only one active centromere. The centromere comes from the formerly dicentric part of the chromosome and co-localizes with the in situ hybridization signal of the mouse minor DNA probe.

F. The selected and non-selected heterologous DNA in the heterochromatin of the sausage chromosome is expressed 1. High levels of the heterologous genes are expressed The TF1004G-19C5 cell line thus carries multiple copies of hygromycin-resistance and β-galactosidase genes localized only in the heterochromatic arm of the sausage chromosome. The TF1004G-19C5 cells can grow very well in the presence of 200 $\mu$g/ml or even 400 $\mu$g/ml hygromycin B. [The level of expression was determined by Northern hybridization with a subfragment of the hygromycin-resistance gene and single copy gene.]

The expression of the non-selected β-galactosidase gene in the TF1004G-19C5 transformant was detected with LacZ staining of the cells. By this method one hundred percent of the cells stained dark blue, showing that there is a high level of β-galactosidase expression in all of TF1004G-19C5 cells.

2. The heterologous genes that are expressed are in the heterochromatin of the sausage chromosome To demonstrate that the genes localized in the constitutive heterochromatin of the sausage chromosome provide the hygromycin resistance and the LacZ staining capability of TF1004G-19C5 transformants [i.e. β-gal expression], PEG-induced cell fusion between TF1004G-19C5 mouse cells and Chinese hamster ovary cells was performed. The hybrids were selected and maintained in HAT medium containing G418 [400 μg/ml] and hygromycin [200 μg/ml]. Two hybrid clones designated 19C5xHa3 and 19C5xHa4, which has been deposited in the ECACC under Accession No. 96040927, were selected. Both carry the sausage chromosome and the minichromosome.

Twenty-seven single cell derived colonies of the 19C5xHa4 hybrid were maintained and analyzed as individual subclones. In situ hybridization with hamster and mouse chromosome painting probes and hamster chromosome 2-specific probes verified that the 19C5xHa4 clone contains the complete Chinese hamster genome and a partial mouse genome. All 19C5xHa4 subclones retained the hamster genome, but different subclones showed different numbers of mouse chromosomes indicating the preferential elimination of mouse chromosomes.

To promote further elimination of mouse chromosomes, hybrid cells were repeatedly treated with BrdU. The BrdU treatments, which destabilize the genome, result in significant loss of mouse chromosomes. The BrdU-treated 19C5xHa4 hybrid cells were divided to three groups. One group of the hybrid cells (GH) were maintained in the presence of hygromycin (200 μg/ml) and G418 (400 μg/ml), and the other two groups of the cells were cultured under G418 (G) or hygromycin (H) selection conditions to promote the elimination of the sausage chromosome or minichromosome.

One month later, single cell derived subclones were established from these three subcultures of the 19C5xHa4 hybrid line. The subclones were monitored by in situ hybridization with biotin-labeled A phage and hamster chromosome painting probes. Four individual clones [G2B5, G3C5, G4D6, G2B4] selected in the presence of G418 that had lost the sausage chromosome but retained the minichromosome were found. Under hygromycin selection only one subclone [H1D3] lost the minichromosome. In this clone the megachromosome [see Example 5] was present.

Since hygromycin-resistance and β-galactosidase genes were thought to be expressed from the sausage chromosome, the expression of these genes was analyzed in the four subclones that had lost the sausage chromosome. In the presence of 200 μg/ml hygromycin, one hundred percent of the cells of four individual subclones died. In order to detect the β-galactosidase expression hybrid, subclones were analyzed by LacZ staining. One hundred percent of the cells of the four subclones that lost the sausage chromosome also lost the LacZ staining capability. All of the other hybrid subclones that had not lost the sausage chromosome under the non-selective culture conditions showed positive LacZ staining.

These findings demonstrate that the expression of hygromycin-resistance and β-galactosidase genes is linked to the presence of the sausage chromosome. Results of in situ hybridizations show that the heterologous DNA is expressed from the constitutive heterochromatin of the sausage chromosome.

In situ hybridization studies of three other hybrid subclones IG2C6, G2D1, and G4D5] did not detect the presence of the sausage chromosome. By the LacZ staining method, some stained cells were detected in these hybrid lines, and when these subclones were transferred to hygromycin selection some colonies survived. Cytological analysis and in situ hybridization of these hygromycin-resistant colonies revealed the presence of the sausage chromosome, suggesting that only the cells of G2C6, G2D1 and G4D5 hybrids that had not lost the sausage chromosome were able to preserve the hygromycin resistance and β-galactosidase expression. These results confirmed that the expression of these genes is linked to the presence of the sausage chromosome. The level of β-galactosidase expression was determined by the immunoblot technique using a monoclonal antibody.

Hygromycin resistance and β-galactosidase expression of the cells which contained the sausage chromosome were provided by the genes localized in the mouse pericentric heterochromatin. This was demonstrated by performing Southern DNA hybridizations on the hybrid cells that lack the sausage chromosome using PCR-amplified subfragments of hygromycin-resistance and β-galactosidase genes as probes. None of the subclones showed hybridization with these probes; however, all of the analyzed clones contained the minichromosome. Other hybrid clones that contain the sausage chromosome showed intense hybridization with these DNA probes. These results lead to the conclusion that hygromycin resistance and β-galactosidase expression of the cells that contain the sausage chromosome were provided by the genes localized in the mouse pericentric heterochromatin.

EXAMPLE 5

The gigachromosome

As described in Example 4, the sausage chromosome was transferred into Chinese hamster cells by cell fusion. Using Hygromycin B/HAT and G418 selection, two hybrid clones 19C5xHa3 and 19C5xHa4 were produced that carry the sausage chromosome. In situ hybridization, using hamster and mouse chromosome-painting probes and a hamster chromosome 2-specific probe, verified that clone 19C5xHa4 contains a complete Chinese hamster genome as well as partial mouse genomes. Twenty-seven separate colonies of 19C5xHa4 cells were maintained and analyzed as individual subclones. Twenty-six out of 27 subclones contained a morphologically unchanged sausage chromosome.

In one subclone of the 19C5xHa3 cell line, 19C5xHa47 [see FIG. 2E], the heterochromatic arm of the sausage chromosome became unstable and showed continuous intrachromosomal growth. In extreme cases, the amplified chromosome arm exceeded 1000 Mb in size (gigachromosome).

EXAMPLE 6

The stable megachromosome

A. Generation of cell lines containing the megachromosome

All 19C5xHa4 subclones retained a complete hamster genome, but different subclones showed different numbers of mouse chromosomes, indicating the preferential elimination of mouse chromosomes. As described in Example 4, to promote further elimination of mouse chromosomes, hybrid cells were treated with BrdU, cultured under G418 (G) or hygromycin (H) selection conditions followed by repeated treatment with $10^{-4}$ M BrdU for 16 hours and single cell subclones were established. The BrdU treatments appeared to destabilize the genome, resulting in a change in the sausage chromosome as well. A gradual increase in a cell population in which a further amplification had occurred was observed. In addition to the ~100–150 Mb heterochromatic arm of the sausage chromosome, an extra centromere and a ~150–250 Mb heterochromatic chromosome arm were formed, which differed from those of mouse chromosome 7. By the acquisition of another euchromatic terminal segment, a new submetacentric chromosome (megachromosome) was formed. Seventy-nine individual subclones were established from these BrdU-treated cultures by single-cell cloning: 42 subclones carried the intact megachromosome, 5 subclones carried the sausage chromosome, and in 32 subclones fragments or translocated segments of the megachromosome were observed. Twenty-six subclones that carried the megachromosome were cultured under non-selective conditions over a two-month period. In 19 out of 26 subclones, the megachromosome was retained. Those subclones which lost the megachromosomes all became sensitive to Hygromycin B and had no β-galactosidase expression, indicating that both markers were linked to the megachromosome.

Two sublines (G3D5 and H1D3), which were chosen for further experiments, showed no changes in the morphology of the megachromosome during more than 100 generations under selective conditions. The G3D5 cells had been obtained by growth of 19C5xHa4 cells in G418-containing medium followed by repeated BrdU treatment, whereas H1D3 cells had been obtained by culturing 19C5xHa4 cells in hygromycin-containing medium followed by repeated BrdU treatment.

B. Structure of the megachromosome

The following results demonstrate that, apart from the euchromatic terminal segments and the integrated foreign DNA, the whole megachromosome is constitutive heterochromatin, containing a tandem array of at least 40 [~7.5 Mb] blocks of mouse major satellite DNA [see FIGS. 2 and 3]. Four satellite DNA blocks are organized into a giant palindrome [amplicon] carrying integrated exogenous DNA sequences at each end. The long and short arms of the submetacentric megachromosome contains 6 and 4 amplicons, respectively.

1. The megachromosome is composed primarily of heterochromatin

Except for the terminal regions and the integrated foreign DNA, the megachromosome is composed primarily of heterochromatin. This was demonstrated by C-banding of the megachromosome, which resulted in positive staining characteristic of constitutive heterochromatin. Apart from the terminal regions and the integrated foreign DNA, the whole megachromosome appears to be heterochromatic. Mouse major satellite DNA is the main component of the pericentric, constitutive heterochromatin of mouse chromosomes and represents ~10% of the total DNA [Waring et al. (1966) *Science* 154:791–794]. Using a mouse major satellite DNA probe for in situ hybridization, strong hybridization was observed throughout the megachromosome, except for its terminal regions. The hybridization showed a segmented pattern: four large blocks appeared on the short arm and usually 4–7 blocks were seen on the long arm. By comparing these segments with the pericentric regions of normal mouse chromosomes that carry ~15 Mb of major satellite DNA, the size of the blocks of major satellite DNA on the megachromosome was estimated to be ~30 Mb.

Using a mouse probe specific to euchromatin [pMCPE1.51; a mouse long interspersed repeated DNA probe], positive hybridization was detected only on the terminal segments of the megachromosome of the H1D3 hybrid subline. In the G3D5 hybrids, hybridization with a hamster-specific probe revealed that several megachromosomes contained terminal segments of hamster origin on the long arm. This observation indicated that the acquisition of the terminal segments on these chromosomes happened in the hybrid cells, and that the long arm of the megachromosome was the recently formed one arm. When a mouse minor satellite probe was used, specific to the centromeres of mouse chromosomes [Wong et al. (1988) *Nucl. Acids Res.* 16:11645–11661], a strong hybridization signal was detected only at the primary constriction of the megachromosome, which colocalized with the positive immunofluorescence signal produced with human anti-centromere serum [LU 851].

In situ hybridization experiments with pH132, pCH110, and λ DNA probes revealed that all heterologous DNA was located in the gaps between the mouse major satellite DNA segments. Each segment of mouse major satellite DNA was bordered by a narrow band of integrated heterologous DNA, except at the second segment of the long arm where a double band of heterologous DNA existed, indicating that the major satellite DNA segment was missing or considerably reduced in size here. This chromosome region served as a useful cytological marker in identifying the long arm of the megachromosome. At a frequency of $10^{-4}$, "restoration" of these missing satellite DNA blocks was observed in one chromatid, when the formation of a whole segment on one chromatid occurred.

After Hoechst 33258 treatment (50 μg/ml for 16 hours), the megachromosome showed undercondensation throughout its length except for the terminal segments. This made it possible to study the architecture of the megachromosome at higher resolution. In situ hybridization with the mouse major satellite probe on undercondensed megachromosomes demonstrated that the ~30 Mb major satellite segments were composed of four blocks of ~7.5 Mb separated from each other by a narrow band of non-hybridizing sequences [FIG. 3]. Similar segmentation can be observed in the large block of pericentric heterochromatin in metacentric mouse chromosomes from the LMTK⁻ and A9 cell lines.

2. The megachromosome is composed of segments containing two tandem ~7.5 Mb blocks followed by two inverted blocks Because of the asymmetry in thymidine content between the two strands of the DNA of the mouse major satellite, when mouse cells are grown in the presence of BrdU for a single S phase, the constitutive heterochromatin shows lateral asymmetry after FPG staining. Also, in the 19C5xHa4 hybrids, the thymidine-kinase [Tk] deficiency of the mouse fibroblast cells was complemented by the hamster Tk gene, permitting BrdU incorporation experiments.

A striking structural regularity in the megachromosome was detected using the FPG technique. In both chromatids, alternating dark and light staining that produced a checkered appearance of the megachromosome was observed. A similar picture was obtained by labelling with fluorescein-conjugated anti-BrdU antibody. Comparing these pictures to the segmented appearance of the megachromosome showed that one dark and one light FPG band corresponded to one ~30 Mb segment of the megachromosome. These results suggest that the two halves of the ~30 Mb segment have an inverted orientation. This was verified by combining in situ hybridization and immunolabelling of the incorporated BrdU with fluorescein-conjugated anti-BrdU antibody on the same chromosome. Since the ~30 Mb segments [or amplicons] of the megachromosome are composed of four blocks of mouse major satellite DNA, it can be concluded that two tandem ~7.5 Mb blocks are followed by two inverted blocks within one segment.

Large-scale mapping of megachromosome DNA by pulsed-field electrophoresis and Southern hybridization with "foreign" DNA probes revealed a simple pattern of restriction fragments. Using endonucleases with none, or only a single cleavage site in the integrated foreign DNA sequences, followed by hybridization with a hyg probe, 1-4 predominant fragments were detected. Since the megachromosome contains 10–12 amplicons with an estimated 3–8 copies of hyg sequences per amplicon (30–90 copies per megachromosome), the small number of hybridizing fragments indicates the homogeneity of DNA in the amplified segments.

3. Scanning electron microscopy of the megachromosome confirmed the above findings The homogeneous architecture of the heterochromatic arms of the megachromosome was confirmed by high resolution scanning electron microscopy. Extended arms of megachromosomes, and the pericentric heterochromatic region of mouse chromosomes, treated with Hoechst 33258, showed similar structure. The constitutive heterochromatic regions appeared more compact than the euchromatic segments. Apart from the terminal regions, both arms of the megachromosome were completely extended, and showed faint grooves, which should correspond to the border of the satellite DNA blocks in the non-amplified chromosomes and in the megachromosome. Without Hoechst treatment, the grooves seemed to correspond to the amplicon borders on the megachromosome arms. In addition, centromeres showed a more compact, finely fibrous appearance than the surrounding heterochromatin.

C. Summary of the formation of the megachromosome

FIG. 2 schematically sets forth events leading to the formation of a stable megachromosome beginning with the generation of a dicentric chromosome in a mouse LMTK⁻ cell line: (A) A single E-type amplification in the centromeric region of the mouse chromosome 7 following transfection of LMTK⁻ cells with λCM8 and λgtWESneo generates the neo-centromere linked to the integrated foreign DNA, and forms a dicentric chromosome. Multiple E-type amplification forms the λneo-chromosome, which was derived from chromosome 7 and stabilized in a mouse-hamster hybrid cell line; (B) Specific breakage between the centromeres of a dicentric chromosome 7 generates a chromosome fragment with the neo-centromere, and a chromosome 7 with traces of foreign DNA at the end; (C) Inverted duplication of the fragment bearing the neo-centromere results in the formation of a stable neo-minichromosome; (D) Integration of exogenous DNA into the foreign DNA region of the formerly dicentric chromosome 7 initiates H-type amplification, and the formation of a heterochromatic arm. By capturing a euchromatic terminal segment, this new chromosome arm is stabilized in the form of the "sausage" chromosome; (E) BrdU treatment and/or drug selection appears to induce further H-type amplification, which results in the formation of an unstable gigachromosome: (F) Repeated BrdU treatments and/or drug selection induce further H-type amplification including a centromere duplication, which leads to the formation of another heterochromatic chromosome arm. It is split off from the chromosome 7 by chromosome breakage and acquires a terminal segment to form the stable megachromosome.

EXAMPLE 7

Summary of some of the cell lines with SATACS and minichromosomes that have been constructed 1. EC3/7-Derived cell lines The LMTK⁻-derived cell line, which is a mouse fibroblast cell line, was transfected with λCM8 and λgtWESneo DNA [see, EXAMPLE 2] to produce transformed cell lines. Among these cell lines was EC3/7, deposited at the European Collection of Animal cell Culture (ECACC) under Accession No. 90051001 [see, U.S. Pat. No. 5,288,625; see, also Hadlaczky et al. (1991) *Proc. Natl. Acad. Sci. U.S.A.* 88:8106–8110 and U.S. application Ser. No. 08/375,271]. This cell line contains the dicentric chromosome with the neo-centromere. Recloning and selection produced cell lines such as EC3/7C5, which are cell lines with the stable neo-minichromosome and the formerly dicentric chromosome [see, FIG. 2C].

2. KE1-2/4 Cells

Fusion of EC3/7 with CHO-K20 cells and selection with G418/HAT produced hybrid cell lines, among these was KE1-2/4, which has been deposited with the ECACC under Accession No. 96040924. KE1-2/4 is a stable cell line that contains the λneo-chromosome [see, FIG. 2D; see, also U.S. Pat. No. 5,288,625], produced by E-type amplifications. KE1-2/4 has been transfected with vectors containing λ DNA, selectable markers, such as the puromycin-resistance gene, and genes of interest, such as p53 and the anti-HIV ribozyme gene. These vectors target the gene of interest into the λneo-chromosome by virtue of homologous recombination with the heterologous DNA in the chromosome.

3. C5pMCT53 Cells

The EC3/7C5 cell line has been co-transfected with pH132, pCH110 and λ DNA [see, EXAMPLE 2] as well as other constructs. Various clones and subclones have been selected. For example transformation with a construct that includes p53 encoding DNA, produced cells designated C5pMCT53.

4. TF1004G24 Cells

As discussed above, cotransfection of EC3/7C5 cells with plasmids [pH132, pCH110 available from Pharmacia, see, also Hall et al. (1983) *J. Mol. Appl. Gen.* 2:101–109] and with A DNA [λcl 875 Sam 7 (New England Biolabs)] produced transformed cells. Among these is TF1004G24, which contains the DNA encoding the anti-HIV ribozyme in the neo-mini-chromosome. Recloning of TF1004G24 produced numerous cell lines. Among these is the NHHL24 cell line. This cell line also has the anti-HIV ribozyme in the neo-minichromosome and expresses high levels of β-gal. It has been fused with CHO-K20 cells to produce various hybrids.

5. TF1004G19-Derived cells

Recloning and selection of the TF1004G transformants produced the cell line TF1004G19, discussed above in EXAMPLE 4, which contains the unstable sausage chromosome and the neo-minichromosome. Single cell cloning produced the TF1004G-19C5 [see FIG. 4] cell line, which has a stable sausage chromosome and the neo-minchromosome. TF1004G-19C5 has been fused with CHO cells and the hybrids grown under selective conditions to produce the 19C5xHa4 and 19C5xHa3 cell lines [see, EXAMPLE 4] and others. Recloning of the 19C5xHa3 cell line yielded a cell line containing a gigachromosome, i.e., cell line 19C5xHa47, see FIG. 2E. BrdU treatment of 19C5xHa4 cells and growth under selective conditions [neomycin (G) and/or hygromycin (H)] has produced hybrid cell lines such as the G3D5 and G4D6 cell lines and others. G3D5 has the neo-minichromosome and the megachromosome. G4D6 has only the neo-minichromosome.

Recloning of 19C5xHa4 cells in H medium produced numerous clones. Among these is H1D3 [see FIG. 4], which has the stable megachromosome. Repeated BrdU treatment and recloning of H1D3 cells has produced the HB31 cell line, which has been used for transformations with the pTEMPUD, pTEMPU and pTEMPU3 vectors [see, Example 12, below].

H1D3 has been fused with a CD4⁺ Hela cell line that carries DNA encoding CD4 and neomycin resistance on a plasmid [see, e.g., U.S. Pat. Nos. 5,413,914, 5,409,810, 5,266,600, 5,223,263, 5,215,914 and 5,144,019, which describe these Hela cells]. Selection with GH has produced hybrids, including H1xHE41 [see FIG. 4], which carries the megachromosome and also a single human chromosome that includes the CD4neo construct. Repeated BrdU treatment and single cell cloning has produced cell lines with the megachromosome [cell line 1B3, see FIG. 4]. About 25% of the 1B3 cells have a truncated megachromosome [~90–120 Mb]. Another of these subclones, designated 2C5, was cultured on hygromycin-containing medium and megachromosome-free cell lines were obtained and grown in G418-containing medium. Recloning of these cells yielded cell lines such as IB4 and others that have a dwarf megachromosome [~150–200 Mb], and cell lines, such as 11C3, which have a micro-megachromosome [~60–90 Mb].

EXAMPLE 8

Replication of the megachromosome

The homogeneous architecture of the megachromomes provides a unique opportunity to perform a detailed analysis of the replication of the constitutive heterochromatin.

A. Materials and methods

1. Culture of cell lines

H1D3 mouse-hamster hybrid cells carrying the megachromosome [see, EXAMPLE 4] were cultured in F-12 medium containing 10% fetal calf serum [FCS] and 400 µg/ml Hygromycin B [Calbiochem]. G3D5 hybrid cells [see, Example 4] were maintained in F-12 medium containing 10% FCS, 400 µg/ml Hygromycin B (Calbiochem), and 400 µg/ml G418 [SIGMA]. Mouse A9 fibroblast cells were cultured in F-12 medium supplemented with 10% FCS.

2. BrdU labelling

In typical experiments, 20–24 parallel semi-confluent cell cultures were set up in 10 cm Petri dishes. Bromodeoxyuridine (BrdU) (Fluka) was dissolved in distilled water alkalized with a drop of NaOH, to make a $10^{-2}$ M stock solution. Aliquots of 10–50 µl of this BrdU stock solution were added to each 10 ml culture, to give a final BrdU concentration of 10–50 µM. The cells were cultured in the presence of BrdU for 30 min, and then washed with warm complete medium, and incubated without BrdU until required. At this point, 5 µg/ml colchicine was added to a sample culture every 1 or 2 h. After 1–2 h colchicine treatment, mitotic cells were collected by "shake-off" and regular chromosome preparations were made for immunolabelling.

3. Immunolabelling of chromosomes and in situ hybridization

Immunolabelling with fluorescein-conjugated anti-BrdU monoclonal antibody (Boehringer) was done according to the manufacturer's recommendations, except that for mouse A9 chromosomes, 2 M hydrochloric acid was used at 37° C. for 25 min, while for chromosomes of hybrid cells, 1 M hydrochloric acid was used at 37° C. for 30 min. In situ hybridization with biotin-labelled probes, and indirect immunofluorescence and in situ hybridization on the same preparation, were performed as described previously [Hadlaczky et al. (1991) *Proc. Natl. Acad. Sci. U.S.A.* 88:8106–8110, see, also U.S. Pat. No. 5,288,625].

4. Microscopy

All observations and microphotography were made by using a Vanox AHBS (Olympus) microscope. Fujicolor 400 Super G or Fujicolor 1600 Super HG high-speed colour negatives were used for photographs.

B. Results

The replication of the megachromosome was analyzed by BrdU pulse labelling followed by immunolabelling. The basic parameters for DNA labelling in vivo were first established. Using a 30-min pulse of 50 µM BrdU in parallel cultures, samples were taken and fixed at 5 min intervals from the beginning of the pulse, and every 15 min up to 1 h after the removal of BrdU. Incorporated BrdU was detected by immunolabelling with fluorescein-conjugated anti-BrdU monoclonal antibody. At the first time point (5 min) 38% of the nuclei were labelled, and a gradual increase in the number of labelled nuclei was observed during incubation in the presence of BrdU, culminating in 46% in the 30-min sample, at the time of the removal of BrdU. At further time points (60, 75, and 90 min) no significant changes were observed, and the fraction of labelled nuclei remained constant [44.5–46%].

These results indicate that (i) the incorporation of the BrdU is a rapid process, (ii) the 30 min pulse-time is sufficient for reliable labelling of S-phase nuclei, and (iii) the BrdU can be effectively removed from the cultures by washing.

The length of the cell cycle of the H1D3 and G3D5 cells was estimated by measuring the time between the appearance of the earliest BrdU signals on the extreme late replicating chromosome segments and the appearance of the same pattern only on one of the chromatids of the chromosomes after one completed cell cycle. The length of G2 period was determined by the time of the first detectable BrdU signal on prophase chromosomes and by the labelled mitoses method [Qastler et al. (1959) *Exp. Cell Res.* 17:420–438]. The length of the S-phase was determined in three ways: (i) on the basis of the length of cell cycle and the fraction of nuclei labelled during the 30–120 min pulse; (ii) by measuring the time between the very end of the replication of the extreme late replicating chromosomes and the detection of the first signal on the chromosomes at the beginning of S phase; (iii) by the labelled mitoses method. In repeated experiments, the duration of the cell cycle was found to be 22–26 h, the S phase 10–14 h, and the G2 phase 3.5–4.5 h.

Analyses of the replication of the megachromosome were made in parallel cultures by collecting mitotic cells at two hour intervals following two hours of colchicine treatment. In a repeat experiment, the same analysis was performed using one hour sample intervals and one hour colchicine treatment. Although the two procedures gave comparable results, the two hour sample intervals were viewed as more appropriate since approximately 30% of the cells were found to have a considerably shorter or longer cell cycle than the average. The characteristic replication patterns of the individual chromosomes, especially some of the late replicating hamster chromosomes, served as useful internal markers for the different stages of S-phase. To minimize the error caused by the different lengths of cell cycles in the different experiments, samples were taken and analyzed throughout the whole cell cycle until the appearance of the first signals on one chromatid at the beginning of the second S-phase.

The sequence of replication in the megachromosome is as follows. At the very beginning of the S-phase, the replication of the megachromosome starts at the ends of the chromosomes. The first initiation of replication in an interstitial position can usually be detected at the centromeric region. Soon after, but still in the first quarter of the S-phase, when the terminal region of the short arm has almost completed its replication, discrete initiation signals appear along the chromosome arms. In the second quarter of the S-phase, as replication proceeds, the BrdU-labelled zones gradually widen, and the checkered pattern of the megachromosome becomes clear [see, e.g., FIG. 2F]. At the same time, pericentric regions of mouse chromosomes also show intense incorporation of BrdU. The replication of the megachromosome peaks at the end of the second quarter and in the third quarter of the S-phase. At the end of the third quarter, and at the very beginning of the last quarter of the S-phase, the megachromosome and the pericentric heterochromatin of the mouse chromosomes complete their replication. By the end of S-phase, only the very late replicating segments of mouse and hamster chromosomes are still incorporating BrdU.

The replication of the whole genome occurs in distinct phases. The signal of incorporated BrdU increased continuously until the end of the first half of the S-phase, but at the beginning of the third quarter of the S-phase chromosome segments other than the heterochromatic regions hardly incorporated BrdU. In the last quarter of the S-phase, the BrdU signals increased again when the extreme late replicating segments showed very intense incorporation.

Similar analyses of the replication in mouse A9 cells were performed as controls. To increase the resolution of the immunolabelling pattern, pericentric regions of A9 chromosomes were decondensed by treatment with Hoechst 33258. Because of the intense replication of the surrounding euchromatic sequences, precise localization of the initial BrdU signal in the heterochromatin was normally difficult, even on undercondensed mouse chromosomes. On those chromosomes where the initiation signal(s) were localized unambiguously, the replication of the pericentric heterochromatin of A9 chromosomes was similar to that of the megachromosome. Chromosomes of A9 cells also exhibited replication patterns and sequences similar to those of the mouse chromosomes in the hybrid cells. These results indicate that the replicators of the megachromosome and mouse chromosomes retained their original timing and specificity in the hybrid cells.

By comparing the pattern of the initiation sites obtained after BrdU incorporation with the location of the integration sites of the "foreign" DNA in a detailed analysis of the first quarter of the S-phase, an attempt was made to identify origins of replication (initiation sites) in relation to the amplicon structure of the megachromosome. The double band of integrated DNA on the long arm of the megachromosome served as a cytological marker. The results showed a colocalization of the BrdU and in situ hybridization signals found at the cytological level, indicating that the "foreign" DNA sequences are in close proximity to the origins of replication, presumably integrated into the non-satellite sequences between the replicator and the satellite sequences [see, FIG. 3]. In the pericentric region of several other chromosomes, dot-like BrdU signals can also be observed that are comparable to the initiation signals on the megachromosome. These signals may represent similar initiation sites in the heterochromatic regions of normal chromosomes.

At a frequency of $10^{-4}$, "uncontrolled" amplification of the integrated DNA sequences was observed in the megachromosome. Consistent with the assumption (above) that "foreign" sequences are in proximity of the replicators, this spatially restricted amplification is likely to be a consequence of uncontrolled repeated firings of the replication origin(s) without completing the replication of the whole segment.

C. Discussion

It has generally been thought that the constitutive heterochromatin of the pericentric regions of chromosomes is late replicating [see, e.g., Miller (1976) Chromosoma 55:165–170]. On the contrary, these experiments evidence that the replication of the heterochromatic blocks starts at a discrete initiation site in the first half of the S-phase and continues through approximately three-quarters of S-phase. This difference can be explained in the following ways: (i) in normal chromosomes, actively replicating euchromatic sequences that surround the satellite DNA obscure the initiation signals, and thus the precise localization of initiation sites is obscured; (ii) replication of the heterochromatin can only be detected unambiguously in a period during the second half of the S-phase, when the bulk of the heterochromatin replicates and most other chromosomal regions have already completed their replication, or have not yet started it. Thus, low resolution cytological techniques, such as analysis of incorporation of radioactively labelled precursors by autoradiography, only detect prominent replication signals in the heterochromatin in the second half of S-phase, when adjacent euchromatic segments are no longer replicating.

In the megachromosome, the primary initiation sites of replication colocalize with the sites where the "foreign" DNA sequences are integrated at the amplicon borders. Similar initiation signals were observed at the same time in the pericentric heterochromatin of mouse chromosomes that do not have "foreign" DNA, indicating that the replication initiation sites at the borders of amplicons may reside in the non-satellite flanking sequences of the satellite DNA blocks. The presence of a primary initiation site at each satellite DNA doublet implies that this large chromosome segment is a single huge unit of replication [megareplicon] delimited by the primary initiation site and the termination point at each end of the unit. Several lines of evidence indicate that, within this higher-order replication unit, "secondary" origins and replicons contribute to the complete replication of the megareplicon:

1. The total replication time of the heterochromatic regions of the megachromosome was ~9–11 h. At the rate of movement of replication forks, 0.5–5 kb per minute, that is typical of eukaryotic chromosomes [Kornberg et al. (1992) DNA Replication. 2nd. ed.., New York: W. H. Freeman and Co, p. 474], replication of a ~15 Mb replicon would require 50–500 h. Alternatively, if only a single replication origin was used, the average replication speed would have to be 25 kb per minute to complete replication within 10 h. By comparing the intensity of the BrdU signals on the euchromatic and the heterochromatic chromosome segments, no evidence for a 5- to 50-fold difference in their replication speed was found.

2. Using short BrdU pulse labelling, a single origin of replication would produce a replication band that moves along the replicon, reflecting the movement of the replication fork. In contrast, a widening of the replication zone that finally gave rise to the checkered pattern of the megachromosome was observed, and within the replication period, the most intensive BrdU incorporation occurred in the second half of the S-phase. This suggests that once the megareplicator has been activated, it permits the activation and firing of "secondary" origins, and that the replication of the bulk of the satellite DNA takes place from these "secondary" origins during the second half of the S-phase. This is supported by the observation that in certain stages of the replication of the megachromosome, the whole amplicon can apparently be labelled by a short BrdU pulse.

Megareplicators and secondary replication origins seem to be under strict temporal and spatial control. The first initiation within the megachromosomes usually occurred at the centromere, and shortly afterward all the megareplicators become active. The last segment of the megachromosome to complete replication was usually the second segment of the long arm. Results of control experiments with mouse A9 chromosomes indicate that replication of the heterochromatin of mouse chromosomes corresponds to the replication of the megachromosome amplicons. Therefore, the pre-existing temporal control of replication in the heterochromatic blocks is preserved in the megachromosome. Positive [Hassan et al. (1994) *J. Cell. Sci.* 107:425–434] and negative [Haase et al. (1994) *Mol. Cell. Biol.* 14:2516–2524] correlations between transcriptional activity and initiation of replication have been proposed. In the megachromosome, transcription of the integrated genes seems to have no effect on the original timing of the replication origins. The concerted, precise timing of the megareplicator initiations in the different amplicons suggests the presence of specific, cis-acting sequences, origins of replication.

Considering that pericentric heterochromatin of mouse chromosomes contains thousands of short, simple repeats spanning 7–15 Mb, and the centromere itself may also contain hundreds of kilobases, the existence of a higher-order unit of replication seems probable. The observed uncontrolled intrachromosomal amplification restricted to a replication initiation region of the megachromosome is highly suggestive of a rolling-circle type amplification, and provides additional evidence for the presence of a replication origin in this region.

The finding that a specific replication initiation site occurs at the boundaries of amplicons suggests that replication might play a role in the amplification process. These results suggest that each amplicon of the megachromosome can be regarded as a huge megareplicon defined by a primary initiation site [megareplicator] containing "secondary" origins of replication. Fusion of replication bubbles from different origins of bi-directional replication [DePamphilis (1993) *Ann. Rev. Biochem.* 62:29–63] within the megareplicon could form a giant replication bubble, which would correspond to the whole megareplicon. In the light of this, the formation of megabase-size amplicons can be accommodated by a replication-directed amplification mechanism. In H and E-type amplifications, intrachromosomal multiplication of the amplicons was observed [see, above EXAMPLES], which is consistent with the unequal sister chromatid exchange model. Induced or spontaneous unscheduled replication of a megareplicon in the constitutive heterochromatin may also form new amplicon(s) leading to the expansion of the amplification or to the heterochromatic polymorphism of "normal" chromosomes. The "restoration" of the missing segment on the long arm of the megachromosome may well be the result of the re-replication of one amplicon limited to one strand.

Taken together, without being bound by any theory, a replication-directed mechanism is a plausible explanation for the initiation of large-scale amplifications in the centromeric regions of mouse chromosomes, as well as for the de novo chromosome formations. If specific [amplificator, i.e., sequences controlling amplification] sequences play a role in promoting the amplification process, sequences at the primary replication initiation site [megareplicator] of the megareplicon are possible candidates.

Preliminary sequence data indicate the presence of highly G+C-rich sequence elements less than 10 kb from the integrated heterologous "foreign" DNA in the megachromosome. These sequences may represent the non-satellite DNA flanking of the A+T-rich satellite DNA blocks and may be the location of the primary replication initiation site in each megareplicon.

EXAMPLE 9

Generation of chromosomes with amplified regions derived from mouse chromosome 1

To show that the events described in EXAMPLES 2–7 are not unique to mouse chromosome 7 and to show that the EC7/3 cell line is not required for formation of the artificial chromosomes, the experiments have been repeated using different initial cell lines and DNA fragments. Any cell or cell line should be amenable to use or can readily be determined to be amenable or not.

A. Materials

The LP11 cell line was produced by the "scrape-loading" transfection method [Fechheimer et al. (1987) *Proc. Natl. Acad. Sci. U.S.A.* 84:8463–8467] using 25 µg plasmid DNA for 5×10$^6$ recipient cells. LP11 cells were maintained in F-12 medium containing 3–15 µg/ml Puromycin [SIGMA].

B. Amplification in LP11 cells

The large-scale amplification described in the above Examples is not restricted to the transformed EC3/7 cell line or to the chromosome 7 of mouse. In an independent transformation experiment, LMTK$^-$ cells were transfected using the calcium phosphate precipitation procedure with a selectable puromycin-resistance gene-containing construct designated pPuroTel [see Example 1.E.2. for a description of this plasmid], to establish cell line LP11. Cell line LP11 carries chromosome(s) with amplified chromosome segments of different lengths [~150–600 Mb]. Cytological analysis of the LP11 cells indicated that the amplification occurred in the pericentric region of the long arm of a submetacentric chromosome formed by Robertsonian translocation. This chromosome arm was identified by G-banding as chromosome 1. C-banding and in situ hybridization with mouse major satellite DNA probe showed that an E-type amplification had occurred: the newly formed region was composed of an array of euchromatic chromosome segments containing different amounts of heterochromatin. The size and C-band pattern of the amplified segments were heterogeneous. In several cells, the number of these amplified units exceeded 50; single-cell subclones of LP11 cell lines, however, carry stable marker chromosomes with 10–15 segments and constant C-band patterns.

Sublines of the thymidine kinase-deficient LP11 cells (e.g., LP11-15P 1C5/7 cell line) established by single-cell cloning of LP11 cells were transfected with a thymidine kinase gene construct. Stable TK$^+$ transfectants were established.

EXAMPLE 10

Purification of SATACS and other chromosomes with a typical base content and/or size I. Purification of artificial chromosomes from genomic chromosomes A. Cell lines 1B3 mouse-hamster-human hybrid cells [see, FIG. 4] carrying the megachromosome or the truncated megachromosome were grown in F-12 medium supplemented with 10% fetal calf serum, 150 µg/ml hygromycin B and 400 µg/ml G418. GHB42 [a cell line recloned from G3D5 cells] mouse-hamster hybrid cells carrying the megachromosome and the minichromosome were cultured in F-12 medium containing 10% fetal calf serum, 150 µg/ml hygromycin B and 400, µg/ml G418. The doubling time of both cell lines was about 24 hours.

B. Chromosome isolation

To accumulate mitotic cells, 5,µg/ml colchicine was added for 12 hours to the cultures. Mitotic cells were then harvested by gentle pipetting of the medium on the layer cells. The mitotic index obtained was 60–80%. The mitotic cells were collected by selective detachment. The cells were sedimented by centrifugation at 200×g for 10 minutes.

Two procedures were used to prepare metaphase chromosomes from these cells, one based on a polyamine buffer system [Cram et al. (1990) *Methods in Cell Biology* 33:377–382], and the other on a modified hexylene glycol buffer system [Hadlaczky et al. (1982) *Chromosoma* 86:643–65].

1. Polyamine procedure

In the polyamine procedure, about $10^7$ mitotic cells were incubated in 10 ml hypotonic buffer (75 mM KCl, 0.2 mM spermine, 0.5 mM spermidine) for 10 minutes at room temperature to swell the cells. The cells were then centrifuged at 100×g for 8 minutes. The cell pellet was drained carefully and about $10^7$ cells were resuspended in 1 ml polyamine buffer [15 mM Tris-HCl, 20 mM NaCl, 80 mM KCl, 2 mM EDTA, 0.5 mM EGTA, 14 mM β-mercaptoethanol, 0.1% digitonin, 0.2 mM Spermine, 0.5 mM spermidine]. Chromosomes were then released by gently drawing the cell suspension up and expelling it through a 22 G needle attached to a 3 ml plastic syringe. The chromosome concentration was about $1-3\times10^8$ chromosomes/ml.

2. Hexylene glycol buffer system

In the second procedure, about $8\times10^6$ mitotic cells were resuspended in 10 ml glycine-hexylene glycol buffer [100 mM glycine, 1% hexylene glycol, pH 8.4–8.6 adjusted with saturated Ca-hydroxide solution] and incubated for 10 minutes at 37° C., followed by centrifugation for 10 minutes to pellet the nuclei. The supernatant was centrifuged again at 200×g for 20 minutes to pellet the chromosomes. Chromosomes were resuspended in 1 ml isolation buffer/$1-3\times10^8$ chromosomes.

C. Staining of chromosomes with DNA-specific dyes

Subsequent to isolation, the chromosome preparation was stained with Hoechst 33258 at 6, µg/ml and chromomycin A3 at 200, µg/ml. Fifteen minutes prior to analysis, 25 mM Na-sulphite and 10 mM Na-citrate were added to the chromosome suspension.

D. Flow sorting of chromosomes

Chromosomes in suspension were passed through a dual-laser cell sorter [FACStar Plus or FAXStar Vantage Becton Dickinson Immunocytometry System] in which two lasers were set to excite the dyes separately, allowing a bivariate analysis of the chromosome by size and base-pair composition. Because of the difference between the base composition of the SATACs and the other chromosomes and the resulting difference in interaction with the dyes, as well as size differences, the SATACs were separated from the other chromosomes.

E. Storage of the sorted artificial chromosomes

The isolated artificial chromosomes are stored in GH buffer (100 mM glycine, 1 % hexylene glycol pH 8.4–8.6 adjusted with saturated Ca-hydroxide solution) [see, e.g., Hadlaczky et al. (1982) *Chromosoma* 86:643–659] for one day and embedded by centrifugation into agarose. The sorted chromosomes were centrifuged into an agarose bed and the plugs are stored in 500 mM EDTA at 4° C. When microinjection is the intended use, they are stored in 30% glycerol at −20° C.

F. Quality control

1. Analysis of the purity

The purity of the sorted chromosomes was checked by fluorescence in situ hybridization (FISH) with a biotin-labeled mouse satellite DNA probe [see, Hadlaczky et al. (1991) *Proc. Natl. Acad. Sci. U.S.A.* 88:8106–8110]. Purity of the isolated chromosomes was about 97–99%.

2. Characteristics of the sorted chromosomes

Pulsed field gel electrophoresis and Southern hybridization were carried out to determine the size distribution of the DNA content of the sorted artificial chromosomes.

G. Functioning of the purified artificial chromosomes

To check whether their activity is preserved, the purified artificial chromosomes may be microinjected (using methods such as those described in Example 13) into primary cells, somatic cells and stem cells which are then analyzed for expression of the heterologous genes carried by the artificial chromosomes, e.g., such as analysis for growth on selective medium and assays of β-galactosidase activity.

II. Sorting of mammalian artificial chromosome-containing microcells

A. Micronucleation

Cells were grown to 80–90% confluency in 4 T150 flasks. Colcemid was added to a final concentration of 0.06 µg/ml, and then incubated with the cells at 37° C. for 24 hours.

B. Enucleation

Ten µg/ml cytochalasin B was added and the resulting microcells were centrifuged at 15,000 rpm for 70 minutes at 28–33° C.

C. Purification of microcells by filtration

The microcells were purified using Swinnex filter units and Nucleopore filters [5 µm and 3 µm].

D. Staining and sorting microcells

As above, the cells were stained with Hoechst and chromomycin A3 dyes. The microcells were sorted by cell sorter to isolate the microcells that contain the mammalian artificial chromosomes.

E. Fusion

The microcells that contain the artificial chromosome are fused, for example, as described in Example 1.A.5., to selected primary cells, somatic cells, embryonic stem cells to generate transgenic animals and for gene therapy purposes, and to other cells to deliver the chromosomes to the cells.

EXAMPLE 11

Introduction of mammalian artificial chromosomes into insect cells

Insect cells are useful hosts for MACs, particularly for use in the production of gene products, for a number of reasons, including:

1. A mammalian artificial chromosome provides an extra-genomic specific integration site for introduction of genes encoding proteins of interest [reduced chance of mutation in production system].

2. The large size of an artificial chromosome permits megabase size DNA integration so that genes encoding an entire pathway leading to a protein or nonprotein of therapeutic value, such as an alkaloid [digitalis, morphine, taxol] can be accomodated by the artificial chromosome.

3. Amplification of genes encoding useful proteins can be accomplished in the artificial mammalian chromosome to obtain higher protein yields in insect cells.

4. Insect cells support required post-translational modifications (glycosylation, phosphorylation) essential for protein biological function.

5. Insect cells do not support mammalian viruses—eliminates cross-contamination of product with human infectious agents.

6. The ability to introduce chromosomes circumvents traditional recombinant baculovirus systems for production of nutritional, industrial or medicinal proteins in insect cell systems.

7. The low temperature optimum for insect cell growth (28° C.) permits reduced energy cost of production.

8. Serum free growth medium for insect cells will result in lower production costs.

9. Artificial chromosome-containing cells can be stored indefinitely at low temperature.

10. Insect larvae will serve as biological factories for the production of nutritional, medicinal or industrial proteins by microinjection of fertilized insect eggs.

A. Demonstration that insect cells recognize mammalian promoters

Gene constructs containing a mammalian promoter, such as the CMV promoter, linked to a detectable marker gene [Renilla luciferase gene (see, e.g., U.S. Pat. No. 5,292,658 for a description of DNA encoding the Renilla luciferase, and plasmid pTZrLuc-1, which can provide the starting material for construction of such vectors, see also SEQ ID No. 10] and also including the simian virus 40 (SV40) promoter operably linked to the βgalactosidase gene were introduced into the cells of two species *Trichoplusia ni* [cabbage looper] and *Bombyx mori* [silk worm].

After transferring the constructs into the insect cell lines either by electroporation or by microinjection, expression of the marker genes was detected in luciferase assays (see e.g., Example 12.C.3) and in β-galactosidase assays (such as lacZ staining assays) after a 24-h incubation. In each case a positive result was obtained in the samples containing the genes which was absent in samples in which the genes were omitted. In addition, a *B. mori*, β-actin promoter-Renilla luciferase gene fusion was introduced into the *T. ni* and *B. mori* cells which yielded light emission after transfection. Thus, certain mammalian promoters function to direct expression of these marker genes in insect cells. Therefore, MACs are candidates for expression of heterologous genes in insect cells.

B. Construction of vectors for use in insect cells and fusion with mammalian cells 1. Transform LMTK⁻ cells with expression vector with:
   a. *B. mori* β-actin promoter—Hyg$^r$ selectable marker gene for insect cells, and
   b. SV40 or CMV promoters controlling a puromycin$^r$ selectable marker gene for mammalian cells.

2. Detect expression of the mammalian promoter in LMTK cells (puromycin$^r$ LMTK cells)

3. Use puromycin$^r$ cells in fusion experiments with Bombyx and Trichoplusia cells, select Hyg$^r$ cells.

C. Insertion of the MACs into insect cells

These experiments are designed to detect expression of a detectable marker gene [such as the, β-galactosidase gene expressed under the control of a mammalian promoter, such as pSV40] located on a MAC that has been introduced into an insect cell. Data indicate that, β-gal was expressed.

Insect cells are fused with mammalian cells containing mammalian artificial chromosomes, e.g., the minichromosome [EC3/7C5] or the mini and the megachromosome [such as GHB42, which is a cell line recloned from G3D5] or a cell line that carries only the megachromosome [such as H1D3 or a redone therefrom]. Fusion is carried out as follows:

1. mammalian+insect cells (50/50%) in log phase growth are mixed;
2. calcium/PEG cell fusion: (10 min–0.5 h);
3. heterokaryons (+72 h) are selected.

The following selection conditions to select for insect cells that contain a MAC can be used: [+=positive selection;−=negative selection]:

1. growth at 28° C. (+insect cells,−mammalian cells);
2. Graces insect cell medium [SIGMA] (−mammalian cells);
3. no exogenous $CO_2$ (−mammalian cells); and/or
4. antibiotic selection (Hyg or G418) (+transformed insect cells).

Immediately following the fusion protocol, many heterokaryons [fusion events] are observed between the mammalian and each species of insect cells [up to 90% heterokaryons]. After growth [2+weeks] on insect medium containing G418 and/or hygromycin at selection levels used for selection of transformed mammalian cells, individual colonies are detected growing on the fusion plates. By virtue of selection for the antibiotic resistance conferred by the MAC and selection for insect cells, these colonies should contain MACs.

The *B. mori*, β-actin gene promoter has been shown to direct expression of the β-galactosidase gene in *B. mori* cells and mammalian cells (e.g., EC3/7C5 cells). The *B. mori* β-actin gene promoter is, thus, particularly useful for inclusion in MACs generated in mammalian cells that will subsequently be transferred into insect cells because the presence of any marker gene linked to the promoter can be determined in the mammalian and resulting insect cell lines.

EXAMPLE 12

Preparation of chromosome fragmentation vectors and other vectors for targeted integration of DNA into MACs Fragmentation of the megachromosome should ultimately result in smaller stable chromosomes that contain about 15 Mb to 50 Mb that will be easily manipulated for use as vectors. Vectors to effect such fragmentation should also aid in determination and identification of the elements required for preparation of an in vitro-produced artificial chromosome.

Reduction in the size of the megachromosome can be achieved in a number of different ways including: stress treatment, such as by starvation, or cold or heat treatment; treatment with agents that destabilize the genome or nick DNA, such as BrdU, coumarin, EMS and others; treatment with ionizing radiation [see, e.g., Brown (1992) *Curr. Opin. Genes Dev.* 2:479–486]; and telomere-directed in vivo chromosome fragmentation [see, e.g., Farr et al. (1995) *EMBO J.* 14:5444–5454].

A. Preparation of vectors for fragmentation of the artificial chromosome and also for targeted integration of selected gene products 1. Construction of pTEMPUD Plasmid pTEMPUD [see FIG. 5] is a mouse homologous recombination "killer" vector for in vivo chromosome fragmentation, and also for inducing large-scale amplification via site-specific integration. With reference to FIG. 5, the ~3,625-bp SalI-PstI fragment was derived from the pBabe-puro retroviral vector [see, Morgenstern et al. (1990) *Nucleic Acids Res.* 18:3587–3596]. This fragment contains DNA encoding ampicillin resistance, the pUC origin of replication, and the puromycin N-acetyl transferase gene under control of the SV40 early promoter. The URA3 gene portion comes from the pYAC5 cloning vector [SIGMA]. URA3 was cut out of pYAC5 with SalI-XhoI digestion, cloned into pNEB193 [New England Biolabs], which was then cut with EcoRI-SalI and ligated to the SalI site of pBabepuro to produce pPU.

A 1293-bp fragment [see SEQ ID No. 1] encoding the mouse major satellite, was isolated as an EcoRI fragment from a DNA library produced from mouse LMTK⁻ fibroblast cells and inserted into the EcoRI site of pPU to produce pMPU.

The TK promoter-driven diphtheria toxin gene [DT-A] was derived from pMC1DT-A [see, Maxwell et al. (1986) *Cancer Res.* 46:4660–4666] by BglII-XhoI digestion and cloned into the pMC1neo poly A expression vector [STRATAGENE, La Jolla, Calif.] by replacing the neomycin-resistance gene coding sequence. The TK promoter, DT-A gene and poly A sequence were removed from this vector, cohesive ends were filled with Klenow and the resulting fragment blunt end-ligated and ligated into the SnaBI [TACGTA] of pMPU to produce pMPUD.

The Hute1 2.5-kb fragment [see SEQ ID No.3] was inserted at the Pstl site [see the 6100 Pstl - 3625 Pstl fragment on pTEMPUD] of pMPUD to produce pTEM-PUD. This fragment includes a human telomere. It includes a unique Bglll site [see nucleotides 1042–1047 of SEQ ID No.3], which will be used as a site for introduction of a synthetic telomere that will include multiple repeats [80] of GGGATT with BamHl and Bglll ends for insertion into the Bglll site which will then remain unique, since the BamHl overhang is compatible with the Bglll site. Ligation of a BamHl fragment to a Bglll destroys the Bglll site, so that only a single Bglll site will remain. Selection for the unique Bglll site insures that the synthetic telomere will be inserted in the correct orientation. The unique Bglll site is the site at which the vector is linearized.

2. Use of pTEMPUD for in vivo chromosome fragmentation

Linearization of pTEMPUD by Bglll results in a linear molecule with a human telomere at one end. Integration of this linear fragment into the chromosome, such as the megachromosome in hybrid cells or any mouse chromosome which contains repeats of the mouse major satellite sequence results in integration of the selectable marker puromycin-resistance gene and cleavage of the plasmid by virtue of the telomeric end. The DT gene prevents that entire linear fragment from integrating by random events, since upon integration and expression it is toxic. Thus random integration will be toxic. Thus, site-directed integration into the targeted DNA will be selected. Such integration will produce fragmented chromosomes.

The fragmented truncated chromosome with the new telomere will survive, and the other fragment without the centromere will be lost. Repeated in vivo fragmentations will ultimately result in selection of the smallest functioning artificial chromosome possible. Thus, this vector can be used to produce minichromosomes from mouse chromosomes, or to fragment the megachromosome. In principle, this vector can be used to target any selected DNA sequence in any chromosome to achieve fragmentation.

3. pTEMPhu and pTEMPhu3

Vectors that specifically target human chromosomes can be constructed from pTEMPUD. These vectors can be used to fragment specific human chromosomes, depending upon the selected satellite sequence, to produce human minichromosomes, and also to isolate human centromeres.

a. pTEMPhu

To render pTEMPUD suitable for fragmenting human chromosomes, the mouse major satellite sequence is replaced with human satellite sequences. Unlike mouse chromosomes, each human chromosome has a unique satellite sequence. For example, the mouse major satellite has been replaced with a human hexameric α-satellite [or alphoid satellite] DNA sequence. This sequence is an 813-bp fragment [nucleotide 232–1044 of SEQ ID No. 2] from clone pS12, deposited in the EMBL database under Accession number X60716, isolated from a human colon carcinoma cell line Colo320 [deposited under Accession No. ATCC CCL 220.1]. The 813-bp alphoid fragment can be obtained from the pS12 clone by nucleic acid amplification using synthetic primers, each of which contains an EcoRI site, as follows:

GGGGAATTCAT TGGGATGTTT CAGTTGA forward primer [SEQ ID No. 4]
CGAAAGTCCCC CCTAGGAGAT CTTAAGGA reverse primer [SEQ ID No. 5].

Digestion of the amplified product with EcoRI results in a fragment with EcoRI ends that includes the human α-satellite sequence. This sequence is inserted into pTEM-PUD in place of the EcoRI fragment that contains the mouse major satellite.

b. pTEMPhu3

In pTEMPhu3, the mouse major satellite sequence is replaced by the 3 kb human chromosome 3-specific α-satellite from D3Z1 [deposited under ATCC Accession No. 85434; see, also Yrokov (1989) *Cytogenet. Cell Genet.* 51:1114].

4. Use of the pTEMPHU3 to induce amplification on human chromosome #3

Each human chromosome contains unique chromosome-specific alphoid sequence. Thus, pTEMPHU3, which is targeted to the chromosome 3-specific α-satellite, can be introduced into human cells under selective conditions, whereby large-scale amplification of the chromosome 3 centromeric region and production of a de novo chromosome ensues. Such induced large-scale amplification provides a means for inducing de novo chromosome formation and also for in vivo cloning of defined human chromosome fragments up to megabase size.

For example, the break-point in human chromosome 3 is on the short arm near the centromere. This region is involved in renal cell carcinoma formation. By targeting pTEMPhu3 to this region, the induced large-scale amplification may contain this region, which can then be cloned using the bacterial and yeast markers in the pTEMPhu3 vector.

The pTEMPhu3 cloning vector allows not only selection for homologous recombinants, but also direct cloning of the integration site in YACS. This vector can also be used to target human chromosome 3, preferably with a deleted short arm, in a mouse-human mono-chromosomal microcell hybrid line. Homologous recombinants can be screened by nucleic acid amplification (PCR), and amplification can be screened by DNA hybridization, Southern hybridization, and in situ hybridization. The amplified region can be cloned into a YAC. This vector and these methods also permit a functional analysis of cloned chromosome regions by reintroducing the cloned amplified region into mammalian cells.

B. Preparation of libraries in YAC vectors for cloning of centromeres and identification of functional chromosomal units Another method that may be used to obtain smaller-sized functional mammalian artificial chromosome units and to clone centromeric DNA involves screening of mammalian DNA YAC vector-based libraries and functional analysis of potential positive clones in a transgenic mouse model system. A mammalian DNA library is prepared in a YAC vector, such as YRT2 [see Schedl et al. (1993) *Nuc. Acids Res.* 21:4783–4787], which contains the murine tyrosinase gene. The library is screened for hybridization to mammalian telomere and centromere sequence probes. Positive clones are isolated and microinjected into pronuclei of fertilized oocytes of NMRI/Han mice following standard techniques. The embryos are then transferred into NMRI/Han foster mothers. Expression of the tyrosinase gene in transgenic offspring confers an identifiable phenotype (pigmentation). The clones that give rise to tyrosinase-expressing transgenic mice are thus confirmed as containing functional mammalian artificial chromosome units.

Alternatively, fragments of SATACs may be introduced into the YAC vectors and then introduced into pronuclei of fertilized oocytes of NMRI/Han mice following standard techniques as above. The clones that give rise to tyrosinase-expressing transgenic mice are thus confirmed as containing functional mammalian artificial chromosome units, particularly centromeres.

C. Incorporation of Heterologous Genes into Mammalian Artificial Chromosomes through The Use of Homology Targeting Vectors As described above, the use of mammalian artificial chromosomes for expression of heterologous genes obviates certain negative effects that may result from random integration of heterologous plasmid DNA into the recipient cell genome. An essential feature of the mammalian artificial chromosome that makes it a useful tool in avoiding the negative effects of random integration is its presence as an extra-genomic gene source in recipient cells. Accordingly, methods of specific, targeted incorporation of heterologous genes exclusively into the mammalian artificial chromosome, without extraneous random integration into the genome of recipient cells, are desired for heterologous gene expression from a mammalian artificial chromosome.

One means of achieving site-specific integration of heterologous genes into artificial chromosomes is through the use of homology targeting vectors. The heterologous gene of interest in subcloned into a targeting vector which contains nucleic acid sequences that are homologous to nucleotides present in the artificial chromosome. The vector is then introduced into cells containing the artificial chromosome for specific site-directed integration into the artificial chromosome through a recombination event at sites of homology between the vector and the chromosome. The homology targeting vectors may also contain selectable markers for ease of identifying cells that have incorporated the vector into the artificial chromosome as well as lethal selection genes that are expressed only upon extraneous integration of the vector into the recipient cell genome. Two exemplary homology targeting vectors, λCF-7 and pλCF-7-DTA, are described below.

1. Construction of Vector λCF-7

Vector λCF-7 contains the cystic fibrosis transmembrane conductance regulator [CFTR] gene as an exemplary therapeutic molecule-encoding nucleic acid that may be incorporated into mammalian artificial chromosomes for use in gene therapy applications. This vector, which also contains the puromycin-resistance gene as a selectable marker, as well as the *Saccharomyces cerevisiae* ura3 gene [orotidine-5-phosphate decarboxylase], was constructed in a series of steps as follows.

a. Construction of pURA

Plasmid pURA was prepared by ligating a 2.6-kb SalI XhoI fragment from the yeast artificial chromosome vector pYAC5 [Sigma; see also Burke et al. (1987) *Science* 236:806–812 for a description of YAC vectors as well as GenBank Accession no. U01086 for the complete sequence of pYAC5] containing the *S. cerevisiae* ura3 gene with a 3.3-kb SalI/SmaI fragment of pHyg [see, e.g., U.S. Pat. Nos. 4,997,764, 4,686,186 and 5,162,215. and the description above]. Prior to ligation the XhoI end was treated with Klenow polymerase for blunt end ligation to the SmaI end of the 3.3 kb fragment of pHyyg. Thus, pURA contains the *S. cerevisiae* ura3 gene, and the *E. coli* ColE1 origin of replication and the ampicillin-resistance gene. The uraE gene is included to provide a means to recover the integrated construct from a mammalian cell as a YAC clone.

b. Construction of pUP2

Plasmid pURA was digested with SalI and ligated to a 1.5-kb SalI fragment of pCEPUR. Plasmid pCEPUR is produced by ligating the 1.1 kb SnaBl-NhaI fragment of pBabe-puro [Morgenstern et al. (1990) *Nucl. Acids Res.* 18:3587–3596; provided by Dr. L. Székely (Microbiology and Tumorbiology Center, Karolinska Institutet, Stockholm); see, also Tonghua et al. (1995) *Chin. Med. J. (Beijing, Engl. Ed.)* 108:653–659; Couto et al. (1994) *Infect. Immun.* 62:2375–2378; Dunckley et al. (1992) FEBS Lett. 296:128–34; French et al. (1995) *Anal. Biochem.* 228:354–355; Liu et al. (1995) *Blood* 85:1095–1103; International PCT application Nos. WO 9520044; WO 9500178, and WO 9419456] to the NheI-NruI fragment of pCEP4 [Invitrogen].

The resulting plasmid, pUP2, contains the all the elements of pURA plus the puromycin-resistance gene linked to the SV40 promoter and polyadenylation signal from pCEPUR.

C. Construction of pUP-CFTR

The intermediate plasmid pUP-CFTR was generated in order to combine the elements of pUP2 into a plasmid along with the CFTR gene. First, a 4.5-kb SalI fragment of pCMV-CFTR that contains the CFTR-encoding DNA [see, also, Riordan et al. (1989) *Science* 245:1066–1073, U.S. Pat. No. 5,240,846, and Genbank Accession no. M28668 for the sequence of the CFTR gene] containing the CFTR gene only was ligated to XhoI-digested pCEP4 [Invitrogen and also described herein] in order to insert the CFTR gene in the multiple cloning site of the Epstein Barr virus-based (EBV) vector pCEP4 [Invitrogen, San Diego, Calif.; see also Yates et al. (1985) *Nature* 313:812–815; see, also U.S. Pat. No. 5,468,615] between the CMV promoter and SV40 polyadenylation signal. The resulting plasmid was designated pCEP-CFTR. Plasmid pCEP-CFTR was then digested with SalI and the 5.8-kb fragment containing the CFTR gene flanked by the CMV promoter and SV40 polyadenylation signal was ligated to SalI-digested pUP2 to generate pUP-CFTR. Thus, pUP-CFTR contains all elements of pUP2 plus the CFTR gene linked to the CMV promoter and SV40 polyadenylation signal.

d. Construction of λCF-7

Plasmid pUP-CFTR was then linearized by partial digestion with EcoRI and the 13 kb fragment containing the CFTR gene was ligated with EcoRI-digested Charon 4Aλ [see Blattner et al. (1977) *Science* 196:161; Williams and Blattner (1979) *J. Virol.* 29:555 and Sambrook et al. (1989) *Molecular Cloning, A Laboratory Manual,* Second Ed., Cold Spring Harbor Laboratory Press, Volume 1, Section 2.18, for descriptions of Charon 4Aλ]. The resulting vector, λCF8, contains the Charon 4Aλ bacteriophage left arm, the CFTR gene linked to the CMV promoter and SV40 polyadenylation signal, the ura3 gene, the puromycin-resistance gene linked to the SV40 promoter and polyadenylation signal, the thymidine kinase promoter [TK], the ColE1 origin of replicaton, the amplicillan resistance gene and the Charon 4Aλ bacteriophage right arm. The λCF8 construct was then digested with XhoI and the resulting 27.1 kb was ligated to the 0.4 kb XhoI/EcoRI fragment of pJBP86 [described below], containing the SV40 polyA signal and the EcoRI-digested Charon 4A λ right arm. The resulting vector λCF-7 contains the Charon 4A λ left arm, the CFTR encoding DNA linked to the CMV promoter and SV40 polyA signal, the ura3 gene, the puromycin resistance gene linked to the SV40 promoter and polyA signal and the Charon 4A λ right arm. The λ DNA fragments provide encode sequences homologous to nucleotides present in the exemplary artificial chromosomes.

The vector is then introduced into cells containing the artificial chromosomes exemplified herein. Accordingly, when the linear λCF-7 vector is introduced into megachromosome-carrying fusion cell lines, such as described herein, it will be specifically integrated into the megachromosome through recombination between the homologous bacteriophage λ sequences of the vector and the artificial chromosome.

2. Construction of Vector λCF-7-DTA

Vector λCF-7-DTA also contains all the elements contained in λCF-7, but additionally contains a lethal selection marker, the diptheria toxin-A (DT-A) gene as well as the ampicillin-resistance gene and an origin of replication. This vector was constructed in a series of steps as follows.

a. Construction of pJBP86

Plasmid pJBP86 was used in the construction of λCF-7, above. A 1.5-kb SalI fragment of pCEPUR containing the puromycin-resistance gene linked to the SV40 promoter and polyadenylation signal was ligated to HindIII-digested pJB8 [see, e.g., Ish-Horowitz et al. (1981) Nucleic Acids Res. 9:2989–2998; available from ATCC as Accession No. 37074; commercially available from Amersham, Arlington Heights, Ill.]. Prior to ligation the SalI ends of the 1.5 kb fragment of pCEPUR and th4 HindIII linearized pJB8 ends were treated with Klenow polymerase. The resulting vector pJBP86 contains the puromycin resistance gene linked to the SV40 promoter and polyA signal, the 1.8 kb COS region of Charon 4Aλ, the ColE1 origin of replication and the ampicillin resistance gene.

b. Construction of pMEP-DTA

A 1.1-kb XhoI/SalI fragment of pMC1-DT-A [see, e.g., Maxwell et al. (1986) Cancer Res. 46:4660–4666] containing the diptheria toxin-A gene was ligated to XhoI-digested pMEP4 [invitrogen, San Diego, Calif.] to generate pMEP-DTA. To produce pMC1-DT-A, the coding region of the DTA gene was isolated as a 800 bp PstIHindIII fragment from p2249-1 and inserted into pMC1neopolyA [pMC1 available from Stratagene] in place of the neo gene and under the control of the TK promotoer. The resulting construct pMC1DT-A was digested with HindIII, the ends filled by Klenow and SalI linkers were ligated to produce a 1061 bp TK-DTA gene cassette with an XhoI end [5'] and a SalI end containing the 270 bp TK promoter and the ~790 bp DT-A fragment. This fragment was ligated into XhoI-digested pMEP4.

Plasmid pMEP-DTA thus contains the DT-A gene linked to the TK promoter and SV40, ColE1 origin of replication and the ampicillin-resistance gene.

c. Construction of pJB83-DTA9

Plasmid pJB8 was digested with HindIII and ClaI and ligated with an oligonucleotide [see SEQ ID NOs. 7 and 8 for the sense and antisense strands of the oligonucleotide, respectively] to generate pJB83. The oligonucleotide that was ligated to ClaI/HindIII-digested pJB8 contained the recognition sites of SwaI, PacI and SrfI restriction endonucleases. These sites will permit ready linearization of the pλCF-7-DTA construct.

Next, a 1.4-kb XhoI/SalI fragment of pMEP-DTA, containing the DT-A gene was ligated to SalI-digested pJB83 to generate pJB83-DTA9.

d. Construction of λCF-7-DTA

The 12-bp overhangs of λCF-7 were removed by Mung bean nuclease and subsequent T4 polymerase treatments. The resulting 41.1-kb linear λCF-7 vector was then ligated to pFB83-DTA9 which had been digested with ClaI and treated with T4 polymerase. The resulting vector, λCF-7-DTA, contains all the elements of λCF-7 as well as the DT-A gene linked to the TK promoter and the SV40 polyadenylation signal, the 1.8 kB Charon 4A λ COS region, the ampicilin-resistance gene [from pJB83-DTA9] and the Col E1 origin of replication [from pJB83-DT9A].

D. Targeting vectors using luciferase markers: Plasmid pMCT-RUC

Plasmid pMCT-RUC [14 kbp] was constructed for site-specific targeting of the Renilla luciferase [see, e.g., U.S. Pat. Nos. 5,292,658 and 5,418,155 for a description of DNA encoding Renilla luciferase, and plasmid pTZrLuc-1, which can provide the starting material for construction of such vectors] gene to a mammalian artificial chromosome. The relevant features of this plasmid are the Renilla luciferase gene under transcriptional control of the human cytomegalovirus immediate-early gene enhancer/promoter; the hygromycin-resistance gene a, positive selectable marker, under the transcriptional control of the thymidine kinase promoter. In particular, this plasmid contains plasmid pAG60 [see, e.g., U.S. Pat. Nos. 5,118,620, 5,021,344, 5,063,162 and 4,946,952; see, also Colbert-Garapin et al. (1981) J. Mol. Biol. 150:1–14], which includes DNA (i.e., the neomycin-resistance gene) homologous to the minichromosome, as well as the Renilla and hygromycin-resistance genes, the HSV-tk gene under control of the tk promoter as a negative selectable marker for homologous recombination, and a unique HpaI site for linearizing the plasmid.

This construct was introduced, via calcium phosphate transfection, into EC3/7C5 cells [see, Lorenz et al. (1996) J. Biolum. Chemilum. 11:31–37]. The EC3/7C5 cells were maintained as a monolayer [see, Gluzman (1981) Cell 23:175–183]. Cells at 50% confluency in 100 mm Petri dishes were used for calcium phosphate transfection [see, Harper et al. (1981) Chromosoma 83:431–439] using 10 μg of linearized pMCT-RUC per plate. Colonies originating from single transfected cells were isolated and maintained in F-12 medium containing hygromycin (300 μg/mL) and 10% fetal bovine serum. Cells were grown in 100 mm Petri dishes prior to the Renilla luciferase assay.

The Renilla luciferase assay was performed [see, e.g., Matthews et al. (1977) Biochemistry 16:85–91]. Hygromycin-resistant cell lines obtained after transfection of EC3/7C5 cells with linearized plasmid pMCT-RUC ["B" cell lines] were grown to 100% confluency for measurements of light emission in vivo and in vitro. Light emission was measured in vivo after about 30 generations as follows: growth medium was removed and replaced by 1 mL RPMI 1640 containing coelenterazine [1 mmol/L final concentration]. Light emission from cells was then visualized by placing the Petri dishes in a low light video image analyzer [Hamamatsu Argus-100]. An image was formed after 5 min. of photon accumulation using 100% sensitivity of the photon counting tube. For measuring light emission in vitro, cells were trypsinized and harvested from one Petri dish, pelleted, resuspended in 1 mL assay buffer [0.5 mol/L NaCl, 1 mmol/L EDTA, 0.1 mol/L potassium phosphate, pH 7.4] and sonicated on ice for 10 s. Lysates were than assayed in a Turner TD-20e luminometer for 10 s after rapid injection of 0.5 mL of 1 mmol/L coelenterazine, and the average value of light emission was recorded as LU [1 LU=1.6×106 hu/s for this instrument].

Independent cell lines of EC3/7C5 cells transfected with linearized plasmid pMCT-RUC showed different levels of Renilla luciferase activity. Similar differences in light emission were observed when measurements were performed on lysates of the same cell lines. This variation in light emission was probably due to a position effect resulting from the random integration of plasmid pMCT-RUC into the mouse genome, since enrichment for site targeting of the luciferase gene was not performed in this experiment.

To obtain transfectant populations enriched in cells in which the luciferase gene had integrated into the minichromosome, transfected cells were grown in the presence of ganciclovis. This negative selection medium selects against cells in which the added pMCT-RUC plasmid integrated into the host EC3/7C5 genome. This selection thereby enriches the surviving transfectant population with cells containing pMCT-RUC in the minichromosome. The cells surviving this selection were evaluated in luciferase assays which revealed a more uniform level of luciferase expression. Additionally, the results of in situ hybridization assays indicated that the Renilla luciferase gene was contained in the minichromosome in these cells, which further indicates successful targeting of pMCT-RUC into the minichromosome.

Plasmid pNEM-1, a variant of pMCT-RUC which also contains λ DNA to provide an extended region of homology to the minichromosome [see, other targeting vectors, below], was also used to transfect EC3/7C5 cells. Site-directed targeting of the Renilla luciferase gene and the hygromycin-resistance gene in pNEM-1 to the minichromosome in the recipient EC3/7C5 cells was achieved. This was verified by DNA amplification analysis and by in situ hybridization. Additionally, luciferase gene expression was confirmed in luciferase assays of the transfectants.

E. Protein secretion targeting vectors

Isolation of heterologous proteins produced intracellularly in mammalian cell expression systems requires cell disruption under potentially harsh conditions and purification of the recombinant protein from cellular contaminants. The process of protein isolation may be greatly facilitated by secretion of the recombinantly produced protein into the extracellular medium where there are fewer contaminants to remove during purification. Therefore, secretion targeting vectors have been constructed for use with the mammalian artificial chromosome system.

A useful model vector for demonstrating production and secretion of heterologous protein in mammalian cells contains DNA encoding a readily detectable reporter protein fused to an efficient secretion signal that directs transport of the protein to the cell membrane and secretion of the protein from the cell. Vectors pLNCX-ILRUC and pLNCX-ILRUCλ, described below, are examples of such vectors. These vectors contain DNA encoding an interleukin-2 (IL2) signal peptide-*Renilla reniformis* luciferase fusion protein. The IL-2 signal peptide [encoded by the sequence set forth in SEQ ID No. 9] directs secretion of the luciferase protein, to which it is linked, from mammalian cells. Upon secretion from the host mammalian cell, the IL-2 signal peptide is cleaved from the fusion protein to deliver mature, active, luciferase protein to the extracellular medium. Successful production and secretion of this heterologous protein can be readily detected by performing luciferase assays which measure the light emitted upon exposure of the medium to the bioluminescent luciferin substrate of the luciferase enzyme. Thus, this feature will be useful when artificial chromosomes are used for gene therapy. The presence of a functional artificial chromosome carrying an IL-Ruc fusion with the accompanying therapeutic genes will be readily monitored. Body fluids or tissues can be sampled and tested for luciferase expression by adding luciferin and appropriate cofactors and observing the bioluminescence.

1. Construction of Protein Secretion Vector pLNCX-ILRUC

Vector pLNCX-ILRUC contains a human IL-2 signal peptide-*R. reniformis* fusion gene linked to the human cytomegalovirus (CMV) immediate early promoter for constitutive expression of the gene in mammalian cells. The construct was prepared as follows.

a. Preparation of the IL-2 signal sequence-encoding DNA

A 69-bp DNA fragment containing DNA encoding the human IL-2 signal peptide was obtained through nucleic acid amplification, using appropriate primers for IL-2, of an HEK 293 cell line [see, e.g., U.S. Pat. No. 4,518,584 for an IL-2 encoding DNA; see, also SEQ ID No. 9; the IL-2 gene and corresponding amino acid sequence is also provided in the Genbank Sequence Database as accession nos. K02056 and J00264]. The signal peptide includes the first 20 amino acids shown in the translations provided in both of these Genbank entries and in SEQ ID NO. 9. The corresponding nucleotide sequence encoding the first 20 amino acids is also provided in these entries [see, e.g., nucleotides 293-52 of accession no. K02056 and nucleotides 478–537 of accession no. J00264), as well as in SEQ ID NO. 9. The amplification primers included an EcoRI site [GAATTC] for subcloning of the DNA fragment after ligation into pGEMT [Promega]. The forward primer is set forth in SEQ ID No. 11 and the sequence of the reverse primer is set forth in SEQ ID No. 12. TTTGAATTCATGTACAGGATGCAACTCCTG forward [SEQ ID No. 11] TTTGAATTCAGTAGGTGCACT-GTTTGTGAC revserse [SEQ ID No. 12]

b. Preparation of the *R. reniformis* luciferase-encoding DNA

The initial source of the *R. reniformis* luciferase gene was plasmid pLXSN-RUC. Vector pLXSN [see, e.g., U.S. Pat. Nos. 5,324,655, 5,470,730, 5,468,634, 5,358,866 and Miller et al. (1989) *Biotechniques* 7:980] is a retroviral vector capable of expressing heterologous DNA under the transcriptional control of the retroviral LTR; it also contains the neomycin-resistance gene operatively linked for expression to the SV40 early region promoter. The *R. reniformis* luciferase gene was obtained from plasmid pTZrLuc-1 [see, e.g., U.S. Pat. No. 5,292,658; see also the Genbank Sequence Database accession no. M63501; and see also Lorenz et al. (1991) *Proc. Natl. Acad. Sci. U.S.A.* 88:4438–4442] and is shown as SEQ ID NO. 10. The 0.97 kb EcoRI/Smal fragment of pTZrLuc-1 contains the coding region of the Renilla luciferase-encodig DNA. Vector pLXSN was digested with and ligated with the luciferase gene contained on a pLXSN-RUC, which contains the luciferase gene located operably linked to the viral LTR and upstream of the SV40 promoter, which directs expression of the neomycin-resistance gene.

c. Fusion of DNA encoding the IL-2 Signal Peptide and the *R. reniformis* Luciferase Gene to Yield pLXSN-ILRUC The pGEMT vector containing the IL-2 signal peptide-encoding DNA described in 1.a. above was digested with EcoRI, and the resulting fragment encoding the signal peptide was ligated to EcoRl-digested pLXSN-RUC. The resulting plasmid, called pLXSN-ILRUC, contains the IL-2 signal peptide-encoding DNA located immediately upstream of the *R. reniformis* gene in pLXSN-RUC. Plasmid pLXSN-ILRUC was then used as a template for nucleic acid amplification of the fusion gene in order to add a Smal site at the 3' end of the fusion gene. The amplification product was subcloned into linearized [EcoRI/Smal-digested] pGEMT [Promega] to generate ILRUC-pGEMT.

d. Introduction of the Fusion Gene into a Vector Containing Control Elements for Expression in Mammalian Cells Plasmid ILRUC-pGEMT was digested with KSpl and Smal to release a fragment containing the IL-2 signal peptide-luciferase fusion gene which was ligated to Hpal-digested pLNCX. Vector pLNCX [see, e.g., U.S. Pat. Nos. 5,324,655 and 5,457,182; see, also Miller and Rosman (1989) *Biotechniques* 7:980–990] is a retroviral vector for expressing heterologous DNA under the control of the CMV promoter; it also contains the neomycin-resistance gene under the transcriptional control of a viral promoter. The vector resulting from the ligation reaction was designated pLNCX-ILRUC. Vector pLNCX-ILRUC contains the IL-2 signal peptide-luciferase fusion gene located immediately downstream of the CMV promoter and upstream of the viral 3' LTR and polyadenylation signal in pLNCX. This arrangement provides for expression of the fusion gene under the control of the CMV promoter. Placement of the heterologous protein-encoding DNA [i.e., the luciferase gene] in operative linkage with the IL-2 signal peptide-encoding DNA provides for expression of the fusion in mammalian cells transfected with the vector such that the heterologous protein is secreted from the host cell into the extracellular medium.

2. Construction of Protein Secretion Targeting Vector pLNCX-ILRUCλ

Vector pLNCX-ILRUC may be modified so that it can be used to introduce the IL-2 signal peptide-luciferase fusion gene into a mammalian artificial chromosome in a host cell. To facilitate specific incorporation of the pLNCX-ILRUC expression vector into a mammalian artificial chromosome, nucleic acid sequences that are homologous to nucleotides present in the artificial chromosome are added to the vector to permit site directed recombination.

Exemplary artificial chromosomes described herein contain λ phage DNA. Therefore, protein secretion targeting vector pLNCX-ILRUCλ was prepared by addition of λ phage DNA [from Charon 4A arms] to produce the secretion vector pLNCX-ILRUC.

3. Expression and Secretion of R. reniformis Luciferase from Mammalian Cells a. Expression of R. reniformis Luciferase Using pLNCX-ILRUC Mammalian cells [LMTK⁻ from the ATCC] were transiently transfected with vector pLNCX-ILRUC [~10 μg] by electroporation [BIORAD, performed according to the manufacturer's instructions]. Stable transfectants produced by growth in G418 for neo selection have also been prepared.

Transfectants were grown and then analyzed for expression of luciferase. To determine whether active luciferase was secreted from the transfected cells, culture media were assayed for luciferase by addition of coelentrazine [see, e.g., Matthews et al. (1977) Biochemistry 16:85–91].

The results of these assays establish that vector pLNCX-ILRUC is capable of providing constitutive expression of heterologous DNA in mammalian host cells. Furthermore, the results demonstrate that the human IL-2 signal peptide is capable of directing secretion of proteins fused to the C-terminus of the peptide. Additionally, these data demonstrate that the R. reniformis luciferase protein is a highly effective reporter molecule, which is stable in a mammalian cell environment, and forms the basis of a sensitive, facile assay for gene expression.

b. Renilla reniformis luciferase appears to be secreted from LMTK⁻ cells.

(i) Renilla luciferase assay of cell pellets
The following cells were tested:
cells with no vector: LMTK⁻ cells without vector as a negative control;
cells transfected with pLNCX only;
cells transfected with RUC-pLNCX [Renilla luciferase gene in pLNCX vector];
cells transfected with pLNCX-ILRUC [vector containing the IL-2 leader sequence+Renilla luciferase fusion gene in pLNCX vector].

Forty-eight hours after electroporation, the cells and culture medium were collected. The cell pellet from 4 plates of cells was resuspended in 1 ml assay buffer and was lysed by sonication. Two hundred μl of the resuspended cell pellet was used for each assay for luciferase activity [see, e.g., Matthews et al. (1977) Biochemistry 16:85–91]. The assay was repeated three times and the average bioluminescence measurement was obtained.

The results showed that there was relatively low background bioluminescence in the cells transformed with pLNCX or the negative control cells; there was a low level observed in the cell pellet from cells containing the vector with the IL-2 leader sequence-luciferase gene fusion and more than 5000 RLU in the sample from cells containing RUC-pLNCX.

(ii) Renilla luciferase assay of cell medium
Forty milliliters of medium from 4 plates of cells were harvested and spun down. Two hundred microliters of medium was used for each luciferase activity assay. The assay was repeated several times and the average bioluminescence measurement was obtained. These results showed that a relatively high level of bioluminescence was detected in the cell medium from cells transformed with pLNCX-ILRUC; about 10-fold lower levels [slightly above the background levels in medium from cells with no vector or transfected with pLNCX only] was detected in the cells transfected with RUC-pLNCX.

(iii) conclusions
The results of these experiments demonstrated that Renilla luciferase appears to be secreted from LMTK⁻ cells under the direction of the IL-2 signal peptide. The medium from cells transfected with Renilla luciferase-encoding DNA linked to the DNA encoding the IL-2 secretion signal had substantially higher levels of Renilla luciferase activity than controls or cells containing luciferase-encoding DNA without the signal peptide-encoding DNA. Also, the differences between the controls and cells containing luciferase encoding-DNA demonstrate that the luciferase activity is specifically from luciferase, not from a non-specific reaction. In addition, the results from the medium of RUC-pLNCX transfected cells, which is similar to background, show that the luciferase activity in the medium does not come from cell lysis, but from secreted luciferase.

c. Expression of R. reniformis Luciferase Using pLNCX-ILRUCλ

To express the IL-2 signal peptide-R. reniformis fusion gene from an mammalian artificial chromosome, vector pLNCX-ILRUCλ is targeted for site-specific integration into a mammalian artificial chromosome through homologous recombination of the λ DNA sequences contained in the chromosome and the vector. This is accomplished by introduction of pLNCX-ILRUCλ into either a fusion cell line harboring mammalian artificial chromosomes or mammalian host cells that contain mammalian artificial chromosomes. If the vector is introduced into a fusion cell line harboring the artificial chromosomes, for example through microinjection of the vector or transfection of the fusion cell line with the vector, the cells are then grown under selective conditions. The artificial chromosomes, which have incorporated vector pLNCX-ILRUCλ, are isolated from the surviving cells, using purification procedures as described above, and then injected into the mammalian host cells.

Alternatively, the mammalian host cells may first be injected with mammalian artificial chromosomes which have been isolated from a fusion cell line. The host cells are then transfected with vector pLNCX-ILRUCλ and grown.

The recombinant host cells are then assayed for luciferase expression as described above.

F. Other targeting vectors

These vectors, which are based on vector pMCT-RUC, rely on positive and negative selection to insure insertion and selection for the double recombinants. A single crossover results in incorporation of the DT-A, which kills the cell, double crossover recombinations delete the DT-1 gene.

1. Plasmid pNEM1 contains

DT-A: Diphtheria toxin gene (negative selectable marker)
Hyg: Hygromycin gene (positive selectable marker)
ruc: Renilla luciferase gene (non-selectable marker)
1: LTR-MMTV promoter
2: TK promoter
3: CMV promoter
MMR: Homology region (plasmid pAG60)

2. plasmid pNEM-2 and -3 are similar to pNEM 1 except for different negative selectable markers pNEM-1: diphtheria toxin gene as "—" selectable marker
pNEM-2: hygromycin antisense gene as "—" selectable marker
pNEM-3: thymidine kinase HSV-1 gene as "—" selectable marker 3. Plasmid - λ DNA based homology pNEMλ-1: base vector
pNEMλ-2: base vector containing p5=gene
1: LTR MMTV promoter
2: SV40 promoter
3: CMV promoter
4: $\mu$TIIA promoter (metallothionein gene promoter)—homology region (plasmid pAG60)
λ L.A. and λ R.A. homology regions for λ left and right arms (λ gt-WES).

EXAMPLE 13

Microinjection of mammalian cells with plasmid DNA

These procedures will be used to microinject MACs into eukaryotic cells, including mammalian and insect cells.

The microinjection technique is based on the use of small glass capillaries as a delivery system into cells and has been used for introduction of DNA fragments into nuclei [see, e.g., Chalfie et al. (1994) *Science* 263:802–804]. It allows the transfer of almost any type of molecules, e.g., hormones, proteins, DNA and RNA, into either the cytoplasm or nuclei of recipient cells This technique has no cell type restriction and is more efficient than other methods, including $Ca^{2+}$—mediated gene transfer and liposome-mediated gene transfer. About 20–30% of the injected cells become successfully transformed.

Microinjection is performed under a phase-contrast microscope. A glass microcapillary, prefilled with the DNA sample, is directed into a cell to be injected with the aid of a micromanipulator. An appropriate sample volume (1–10 pl) is transferred into the cell by gentle air pressure exerted by a transjector connected to the capillary. Recipient cells are grown on glass slides imprinted with numbered squares for convenient localization of the injected cells.

a. Materials and equipment

Nunclon tissue culture dishes 35×10 mm, mouse cell line EC3/7C5 Plasmid DNA pCH110 [Pharmacia], Purified Green Florescent Protein (GFP) [GFPs from Aequorea and Renilla have been purified and also DNA encoding GFPs has been cloned; see, e.g., Prasher et al. (1992) *Gene* 111:229–233; International PCT Application No. WO 95/07463, which is based on U.S. application Ser. No. 08/119,678 and U.S. application Ser. No. 08/192,274], ZEISS Axiovert 100 microscope, Eppendorf transjector 5246, Eppendorf micromanipulator 5171, Eppendorf Cellocate coverslips, Eppendorf microloaders, Eppendorf femtotips and other standard equipment.

b. Protocol for injecting (1) Fibroblast cells are grown in 35 mm tissue culture dishes (37° C., 5% $CO_2$) until the cell density reaches 80% confluency. The dishes are removed from the incubator and medium is added to about a 5 mm depth.

(2) The dish is placed onto the dish holder and the cells observed with 10×objective; the focus is desirably above the cell surface.

(3) Plasmid or chromosomal DNA solution [1 ng/$\mu$l] and GFP protein solution are further purified by centrifuging the DNA sample at a force sufficient to remove any particular debris [typically about 10,000 rpm for 10 minutes in a microcentrifuge].

(4) Two 2, $\mu$l of the DNA solution (1 ng/$\mu$l) is loaded into a microcapillary with an Eppendorf microloader. During loading, the loader is inserted to the tip end of the microcapillary. GFP (1 mg/ml) is loaded wit the same procedure.

(5) The protecting sheath is removed from the microcapillary and the microcapillary is fixed onto the capillary holder connected with the micromanipulator.

(6) The capillary tip is lowered to the surface of the medium and is focussed on the cells gradually until the tip of the capillary reaches the surface of a cell. The capillary is lowered further so that the it is inserted into the cell. Various parameters, such as the level of the capillary, the time and pressure, are determined for the particular equipment. For example, using the fibroblast cell line C5 and the above-noted equipment, the best conditions are: injection time 0.4 second, pressure 80 psi. DNA can then be automatically injected into the nuclei of the cells.

(7) After injection, the cells are returned to the incubator, and incubated for about 18–24 hours.

(8) After incubation the number of transformants can be determined by a suitable method, which depends upon the selection marker. For example, if green fluorescent protein is used, the assay can be performed using UV light source and fluorescent filter set at 0–24 hours after injection. If β-gal-containing DNA, such as DNA-derived from pHC110, has been injected, then the transformants can be assayed for β-gal.

(c) Detection of β-galactosidase in cells injected with plasmid DNA

The medium is removed from the culture plate and the cells are fixed by addition of 5 ml of fixation Solution I: (1% glutaraldehyde; 0.1M sodium phosphate buffer, pH 7.0; 1 mM $MgCl_2$), and incubated for 15 minutes at 37° C. Fixation Solution I is replaced with 5 ml of X-gal Solution II: [0.2% X-gal, 10 mM sodium phosphate buffer (pH 7.0), 150 mM NaCl, 1 mM $MgCl_2$, 3.3 mM $K_4Fe(CN)_6H_2O$, 3.3 mM $K_3Fe(CN)_6$], and the plates are incubated for 30–60 minutes at 37° C.

The X-gal solution is removed and 2 ml of 70% glycerol is added to each dish. Blue stained cells are identified under a light microscope.

This will be used to introduce a MAC, particularly the MAC with the anti-HIV megachromosome, to produce a mouse model for anti-HIV activity.

EXAMPLE 14

Transgenic animals

Transgenic animals can be generated that express heterologous genes which confer desired traits, e.g., disease resistance, in the animals. A transgenic mouse is prepared to serve as model of a disease-resistant animal. Genes that encode vaccines or that encode therapeutic molecules can be introduced into embryos or ES cells to produce animals that express the gene product and thereby are resistant to or less susceptible to a particular disorder.

The mammalian artificial megachromosome and others of the artificial chromosomes, particularly the SATACs, can be used to generate transgenic animals, including mammals and birds, that stably express genes conferring desired traits, such as genes conferring resistance to pathogenic viruses. The artificial chromosomes can also be used to produce transgenic animals, such as pigs, that can produce immunologically humanized organs for xenotransplantation.

For example, transgenic mice containing a transgene encoding an anti-HIV ribozyme provide a useful model for the development of stable transgenic animals using these methods. The artificial chromosomes can be used to produce transgenic animals, particularly, cows, goats, mice, oxen, camels, pigs and sheep, that produce the proteins of interest in their milk; and to produce transgenic chickens and other egg-producing fowl, that produce therapeutic proteins or other proteins of interest in their eggs. For example, use of mammary gland-specific promoters for expression of heterologous DNA in milk is known [see, e.g. U.S. Pat. No. 4,873,316]. In particular, a milk-specific promoter or a promoter, preferably linked to a milk-specific signal peptide, specifically activated in mammary tissue is operatively linked to the DNA of interest, thereby providing expression of that DNA sequence in milk.

1. Development of Control Transgenic Mice Expressing Anti-HIV Ribozyme

Control transgenic mice are generated in order to compare stability and amounts of transgene expression in mice developed using transgene DNA carried on a vector (control mice) with expression in mice developed using transgenes carried in an artificial megachromosome.

a. Development of Control Transgenic Mice Expressing β-galactosidase

One set of control transgenic mice was generated by microinjection of mouse embryos with the β-galactosidase gene alone. The microinjection procedure used to introduce the plasmid DNA into the mouse embryos is as described in Example 13, but modified for use with embryos [see, e.g., Hogan et al. (1994) *Manipulating the Mouse Embryo, A Laboratory Manual,* Cold Spring Harbor Laboratory Press, Cold Spring Harbor, N.Y., see, especially pages 255–264 and Appendix 3]. Fertilized mouse embryos [Strain CB6 obtained from Charles River Co.] were injected with 1 ng of plasmid pCH110 (Pharmacia) which had been linearized by digestion with BamHl. This plasmid contains the β-galactosidase gene linked to the SV40 late promoter. The β-galactosidase gene product provides a readily detectable marker for successful transgene expression. Furthermore, these control mice provide confirmation of the microinjection procedure used to introduce the plasmid into the embryos. Additionally, because the mega-chromosome that is transferred to the mouse embryos in the model system (see below) also contains the β-galactosidase gene, the control transgenic mice that have been generated by injection of pCH110 into embryos serve as an analogous system for comparison of heterologous gene expression from a plasmid versus from a gene carried on an artifical chromosome.

After injection, the embryos are cultured in modified HTF medium under 5% $CO_2$ at 37° C. for one day until they divide to form two cells. The two-cell embryos are then implanted into surrogate mother female mice [for procedures see, *Manipulating the Mouse Embryo, A Laboratory Manual* (1994) Hogan et al., eds., Cold Spring Harbor Laboratory Press, Cold Spring Harbor, N.Y., pp. 127 et seq.].

b. Development of Control Transgenic Mice Expressing Anti-HIV Ribozyme

One set of anti-HIV ribozyme gene-containing control transgenic mice was generated by microinjection of mouse embryos with plasmid pCEPUR-132 which contains three different genes: (1) DNA encoding an anti-HIV ribozyme, (2) the puromycin-resistance gene and (3) the hygromycin-resistance gene. Plasmid pCEPUR-132 was constructed by ligating portions of plasmid pCEP-132 containing the anti-HIV ribozyme gene (referred to as ribozyme D by Chang et al. [(1990) *Clin. Biotech.* 2:23–31]; see also U.S. Pat. No. 5,144,019 to Rossi et al., particularly FIG. 4 of the patent) and the hygromycin-resistance gene with a portion of plasmid pCEPUR containing the puromycin-resistance gene.

Plasmid pCEP-132 was constructed as follows. Vector pCEP4 (Invitrogen, San Diego, Calif.; see also Yates et al. (1985) *Nature* 313:812–815) was digested with Xhol which cleaves in the multiple cloning site region of the vector. This ~10.4-kb vector contains the hygromycin-resistance gene linked to the thymidine kinase gene promoter and polyadenylation signal, as well as the ampicillin-resistance gene and ColE1 origin of replication and EBNA-1 (Epstein-Barr virus nuclear antigen) genes and OriP. The multiple cloning site is flanked by the cytomegalovirus promoter and SV40 polyadenylation signal.

Xhol-digested pCEP4 was ligated with a fragment obtained by digestion of plasmid 132 (see Example 4 for a description of this plasmid) with Xhol and Sall. This Xhol/Sall fragment contains the anti-HIV ribozyme gene linked at the 3' end to the SV40 polyadenylation signal. The plasmid resulting from this ligation was designated pCEP-132. Thus, in effect, pCEP-132 comprises pCEP4 with the anti-HIV ribozyme gene and SV40 polyadenylation signal inserted in the multiple cloning site for CMV promoter-driven expression of the anti-HIV ribozyme gene.

To generate pCEPUR-132, pCEP-132 was ligated with a fragment of pCEPUR. pCEPUR was prepared by ligating a 7.7-kb fragment generated upon Nhel/Nrul digestion of pCEP4 with a 1.1-kb Nhel SnaBl fragment of pBabe [see Morgenstern and Land (1990) *Nucleic Acids Res.* 18:3587–3596 for a description of pBabe] that contains the puromycin-resistance gene linked at the 5' end to the SV40 promoter. Thus, pCEPUR is made up of the ampicillin-resistance and EBNA1 genes, as well as the ColE1 and OriP elements from pCEP4 and the puromycin-resistance gene from pBabe. The puromycin-resistance gene in pCEPUR is flanked by the SV40 promoter (from pBabe) at the 5' end and the SV40 polyadenylation signal (from pCEP4) at the 3' end.

Plasmid pCEPUR was digested with Xhol and Sall and the fragment containing the puromycin-resistance gene linked at the 5' end to the SV40 promoter was ligated with Xhol-digested pCEP-132 to yield the ~12.1-kb plasmid designated pCEPUR-132. Thus, pCEPUR-132, in effect, comprises pCEP-132 with puromycin-resistance gene and SV40 promoter inserted at the Xhol site. The main elements of pCEPUR-1 32 are the hygromycin-resistance gene linked to the thymidine kinase promoter and polyadenylation signal, the anti-HIV ribozyme gene linked to the CMV promoter and SV40 polyadenylation signal, and the puromycin-resistance gene linked to the SV40 promtoer and polyadenylation signal. The plasmid also contains the ampicillin-resistance and EBNA1 genes and the ColE1 origin of replication and OriP.

Zygotes were prepared from (C57BL/6JxCBA/J) F1 female mice [see, e.g., *Manipulating the Mouse Embryo, A Laboratory Manual* (1994) Hogan et al., eds., Cold Spring Harbor Laboratory Press, Cold Spring Harbor, N.Y., p. 429], which had been previously mated with a (C57BL/6JxCBA/J) F1 male. The male pronuclei of these F2 zygotes were injected [see, *Manipulating the Mouse Embryo, A Laboratory Manual* (1994) Hogan et al., eds., Cold Spring Harbor Laboratory Press, Cold Spring Harbor, N.Y.] with pCEPUR-132 (~3 μg/ml), which had been linearized by digestion with NruI. The injected eggs were then implanted in surrogate mother female mice for development into transgenic offspring.

These primary carrier offspring were analyzed (as described below) for the presence of the transgene in DNA isolated from tail cells. Seven carrier mice that contained transgenes in their tail cells (but that may not carry the transgene in all their cells, i.e., they may be chimeric) were allowed to mate to produce non-chimeric or germ-line heterozygotes. The heterozygotes were, in turn, crossed to generate homozygote transgenic offspring.

2. Development of Model Transgenic Mice Using Mammalian Artificial Chromosomes

Fertilized mouse embryos are microinjected (as described above) with megachromosomes (1–10 pL containing 0–1 chromosomes/pL) isolated from fusion cell line G3D5 or H1D3 (described above). The megachromosomes are isolated as described herein. Megachromosomes isolated from either cell line carry the anti-HIV ribozyme (ribozyme D) gene as well as the hygromycin-resistance and β-galactosidase genes. The injected embryos are then developed into transgenic mice as described above.

Alternatively, the megachromosome-containing cell line G3D5* or H1D3* is fused with mouse embryonic stem cells [see, e.g., U.S. Pat. No. 5,453,357, commerically available; see *Manipulating the Mouse Embryo, A Laboratory Manual* (1994) Hogan et al., eds., Cold Spring Harbor Laboratory Press, Cold Spring Harbor, N.Y., pages 253–289] following standard procedures see also, e.g., *Guide to Techniques in Mouse Development* in *Methods in Enzymology* Vol. 25, Wassarman and De Pamphilis, eds. (1993), pages 803–932]. (It is also possible to deliver isolated megachromosomes into embryonic stem cells using the Microcell procedure [such as that described above].) The stem cells are cultured in the presence of a fibroblast [e.g., STO fibroblasts that are resistant to hygromycin and puromycin]. Cells of the resultant fusion cell line, which contains megachromosomes carrying the transgenes [i.e., anti-HIV ribozyme, hygromycin-resistance and β-galactosidase genes], are then transplanted into mouse blastocysts, which are in turn implanted into a surrogate mother female mouse where development into a transgenic mouse will occur.

Mice generated by this method are chimeric in that the transgenes will be expressed in only certain areas of the mouse, e.g., the head, and thus may not be expressed in all cells.

3. Analysis of Transgenic Mice for Transgene Expression

Beginning when the transgenic mice, generated as described above, are three-to-four weeks old, they can be analyzed for stable expression of the transgenes that were transferred into the embryos [or fertilized eggs] from which they develop. The transgenic mice may be analyzed in several ways as follows.

a. Analysis of Cells Obtained from the Transgenic Mice

Cell samples [e.g., spleen cells, lymphocytes, tail cells] are obtained from the transgenic mice. Any cells may be tested for transgene expression. If, however, the mice are chimeras generated by microinjection of fertilized eggs with fusions of embryonic stem cells with megachromosome-containing cells, only cells from areas of the mouse that carry the transgene are expected to express the transgene. If the cells survive growth on hygromycin [or hygromycin and puromycin or neomycin, if the cells are obtained from mice generated by transfer of both antibiotic-resistance genes], this is one indication that they are stably expressing the transgenes. RNA isolated from the cells according to standard methods may also be analyzed by northern blot procedures to determine if the cells express transcripts that hybridize to nucleic acid probes based on the antibiotic-resistance genes.

Additionally, cells obtained from the transgenic mice may also be analyzed for β-galactosidase expression using standard assays for this marker enzyme [for example, by direct staining of the product of a reaction involving β-galactosidase and the X-gal substrate, see, e.g., Jones (1986) *EMBO* 5:3133–3142, or by measurement of β-galactosidase activity, see, e.g., Miller (1972) in *Experiments in Molecular Genetics* pp. 352–355, Cold Spring Harbor Press]. Analysis of β-galactosidase expression is particularly used to evaluate transgene expression in cells obtained from control transgenic mice in which the only transgene transferred into the embryo was the β-galactosidase gene.

Stable expression of the anti-HIV ribozyme gene in cells obtained from the transgenic mice may be evaluated in several ways. First, DNA isolated from the cells according to standard procedures may be subjected to nucleic acid amplification using primers corresponding to the ribozyme gene sequence. If the gene is contained within the cells, an amplified product of pre-determined size is detected upon hybridization of the reaction mixture to a nucleic acid probe based on the ribozyme gene sequence. Furthermore, DNA isolated from the cells may be analyzed using Southern blot methods for hybridization to such a nucleic acid probe. Second, RNA isolated from the cells may be subjected to northern blot hybridization to determine if the cells express RNA that hybridizes to nucleic acid probes based on the ribozyme gene. Third, the cells may be analyzed for the presence of anti-HIV ribozyme activity as described, for example, in Chang et al. (1990) *Clin. Biotech.* 2:23–31. In this analysis, RNA isolated from the cells is mixed with radioactively labeled HIV gag target RNA which can be obtained by in vitro transcription of gag gene template under reaction conditions favorable to in vitro cleavage of the gag target, such as those described in Chang et al. (1990) *Clin. Biotech.* 2:23–31. After the reaction has been stopped, the mixture is analyzed by gel electrophoresis to determine if cleavage products smaller in size than the whole template are detected; presence of such cleavage fragments is indicative of the presence of stably expressed ribozyme.

b. Analysis of Whole Transgenic Mice

Whole transgenic mice that have been generated by transfer of the anti-HIV ribozyme gene [as well as selection and marker genes] into embryos or fertilized eggs can additionally be analyzed for transgene expression by challenging the mice with infection with HIV. It is possible for mice to be infected with HIV upon intraperitoneal injection with high-producing HIV-infected U937 cells [see, e.g., Locardi et al. (1992) *J. Virol.* 66:1649–1654]. Successful infection may be confirmed by analysis of DNA isolated from cells, such as peripheral blood mononuclear cells, obtained from transgenic mice that have been injected with HIV-infected human cells. The DNA of infected transgenic mice cells will contain HIV-specific gag and env sequences, as demonstrated by, for example, nucleic acid amplification using HIV-specific primers. If the cells also stably express the anti-HIV ribozyme, then analysis of RNA extracts of the cells should reveal the smaller gag fragments arising by cleavage of the gag transcript by the ribozyme.

Additionally, the transgenic mice carrying the anti-HIV ribozyme gene can be crossed with transgenic mice expressing human CD4 (i.e., the cellular receptor for HIV) [see Gillespie et al. (1993) *Mol. Cell. Biol.* 13:2952–2958; Hanna et al. (1994) *Mol. Cell. Biol.* 14:1084–1094; and Yeung et al. (1994) *J. Exp. Med.* 180:1911–1920, for a description of transgenic mice expressing human CD4]. The offspring of these crossed transgenic mice expressing both the CD4 and anti-HIV ribozyme transgenes should be more resistant to infection [as a result of a reduction in the levels of active HIV in the cells] than mice expressing CD4 alone [without expressing anti-HIV ribozyme].

4. Development of transgenic chickens using artificial chromosomes

The development of transgenic chickens has many applications in the improvement of domestic poultry, an agricultural species of commercial significance, such as disease resistance genes and genes encoding therapeutic proteins. It appears that efforts in the area of chicken transgenesis have been hampered due to difficulty in achieving stable expression of transgenes in chicken cells using conventional methods of gene transfer via random introduction into recipient cells. Artificial chromosomes are, therefore, particularly useful in the development of transgenic chickens because they provide for stable maintenance of transgenes in host cells.

a. Preparation of artificial chromosomes for introduction of transgenes into recipient chicken cells (i) Mammalian artificial chromosomes Mammalian artificial chromosomes, such as the SATACs and minichromosomes described herein, can be modified to incorporate detectable reporter genes and/or transgenes of interest for use in developing transgenic chickens. Alternatively, chicken-specific artifical chromosomes can be constructed using the methods herein. In particular, chicken artificial chromosomes [CACs] can be prepared using the methods herein for preparing MACs; or, as described above, the chicken librarires can be introduced into MACs provided herein and the resulting MACs introduced into chicken cells and those that are functional in chicken cells selected.

As described in Examples 4 and 7, and elsewhere herein, artificial chromosome-containing mouse LMTK⁻-derived cell lines, or minichromosome-containing cell lines, as well as hybrids thereof, can be transfected with selected DNA to generate MACs [or CACs] that have integrated the foreign DNA for functional expression of heterologous genes contained within the DNA.

To generate MACs or CACs containing transgenes to be expressed in chicken cells, the MAC-containing cell lines may be transfected with DNA that includes λ DNA and transgenes of interest operably linked to a promoter that is capable of driving expression of genes in chicken cells. Alternatively, the minichromosomes or MACs [or CACs], produced as described above, can be isolated and introduced into cells, followed by targeted integration of selected DNA. Vectors for targeted integration are provided herein or can be constructed as described herein.

Promoters of interest include constitutive, inducible and tissue (or cell)-specific promoters known to those of skill in the art to promote expression of genes in chicken cells. For example, expression of the lacZ gene in chicken blastodermal cells and primary chicken fibroblasts has been demonstrated using a mouse heat-shock protein 68 (hsp 68) promoter [phspPTlacZpA; see Brazolot et al. (1991) *Mol. Reprod. Devel.* 30:304–312], a $Zn^{2+}$-inducible chicken metallothionein (cMt) promoter [pCBcMtlacZ; see Brazolot et al. (1991) *Mol. Reprod. Devel.* 30:304–312], the constitutive Rous sarcoma virus and chicken β-actin promoters in tandem [pmiwZ; see Brazolot et al. (1991) *Mol. Reprod. Devel.* 30:304–312] and the constitutive cytomegalovirus (CMV) promoter. Of particular interest herein are egg-specific promoters that are derived from genes, such as ovalbumin and lysozyme, that are expressed in eggs.

The choice of promoter will depend on a variety of factors, including, for example, whether the transgene product is to be expressed throughout the transgenic chicken or restricted to certain locations, such as the egg. Cell-specific promoters functional in chickens include the steroid-responsive promoter of the egg ovalbumin protein-encoding gene [see Gaub et al. (1987) *EMBO J.* 6:2313–2320; Tora et al. (1988) *EMBO J.* 7:3771–3778; Park et al. (1995) *Biochem. Mol. Biol. Int.* (Australia) 36:811–816].

(ii) Chicken artificial chromosomes

Additionally, chicken artificial chromosomes may be generated using methods described herein. For example, chicken cells, such as primary chicken fibroblasts [see Brazolot et al. (1991) *Mol. Reprod. Devel.* 30:304–312], may be transfected with DNA that encodes a selectable marker [such as a protein that confers resistance to antibiotics] and that includes DNA (such as chicken satellite DNA) that targets the introduced DNA to the pericentric region of the endogenous chicken chromosomes. Transfectants that survive growth on selection medium are then analyzed, using methods described herein, for the presence of artificial chromosomes, including minichromosomes, and particularly SATACs. An artificial chromosome-containing transfectant cell line may then be transfected with DNA encoding the transgene of interest [fused to an appropriate promoter] along with DNA that targets the foreign DNA to the chicken artificial chromosome.

b. Introduction of artificial chromosomes carrying transgenes of interest into recipient chicken cells Cell lines containing artificial chromosomes that harbor transgene(s) of interest (i.e., donor cells) may be fused with recipient chicken cells in order to transfer the chromosomes into the recipient cells. Alternatively, the artificial chromosomes may be isolated from the donor cells, for example, using methods described herein [see, e.g., Example 10], and directly introduced into recipient cells.

Exemplary chicken recipient cell lines include, but are not limited to, stage X blastoderm cells [see, e.g., Brazolot et al. (1991) *Mol. Reprod. Dev.* 30:304–312; Etches et al. (1993) *Poultry Sci.* 72:882–889; Petitte et al. (1990) *Development* 108:185–189] and chick zygotes [see, e.g., Love et al. (1994) *Biotechnology* 12:60–63].

For example, microcell fusion is one method for introduction of artificial chromosomes into avian cells [see, e.g., Dieken et al. [(1996) *Nature Genet.* 12:174–182 for methods of fusing microcells with DT40 chicken pre-B cells]. In this method, microcells are prepared [for example, using procedures described in Example 1.A.5] from the artificial chromosome-containing cell lines and fused with chicken recipient cells.

Isolated artificial chromosomes may be directly introduced into chicken recipient cell lines through, for example, lipid-mediated carrier systems, such as lipofection procedures [see, e.g., Brazolot et al. (1991) *Mol. Reprod. Dev.* 30:304–312] or direct microinjection. Microinjection is generally preferred for introduction of the artificial chromosomes into chicken zygotes [see, e.g., Love et al. (1994) *Biotechnology* 12:60–63].

c. Development of transgenic chickens

Transgenic chickens may be developed by injecting recipient Stage X blastoderm cells (which have received the artificial chromosomes) into embryos at a similar stage of development [see, e.g., Etches et al. (1993) *Poultry Sci.* 72:882–889; Petitte et al. (1990) *Development* 108:185–189;

and Carsience et al. (1993) *Development* 117: 669–675]. The recipient chicken embryos within the shell are candled and allowed to hatch to yield a germline chimeric chicken that will express the transgene(s) in some of its cells.

Alternatively, the artificial chromosomes may be introduced into chick zygotes, for example through direct microinjection [see, e.g., Love et al. (1994) *Biotechnoloqy* 12:60–63], which thereby are incorporated into at least a portion of the cells in the chicken. Inclusion of a tissue-specific promoter, such an an egg-specific promoter, will ensure appropriate expression of operatively-linked heterologous DNA.

The DNA of interest may also be introduced into a minichromosome, by methods provided herein. The minichromosome may either be one provided herein, or one generated in chicken cells using the methods herein. The heterologous DNA will be introduced using a targeting vector, such as those provided herein, or constructed as provided herein.

Since modifications will be apparent to those of skill in this art, it is intended that this invention be limited only by the scope of the appended claims.

What is claimed:

1. A method of producing a product that is produced upon expression of a metabolic pathway, comprising culturing a cell comprising an artificial chromosome under conditions whereby the pathway is expressed to produce the product, wherein:
the artificial chromosome is selected from the group consisting of a satellite artificial chromosome and a minichromosome;
the artificial chromosome comprises multiple copies of a heterologous gene or a plurality of heterologous genes; and
the heterologous genes encode proteins that comprise the metabolic pathway.

2. The method of claim 1, wherein the product is a vitamin, a hormone, a nucleotide, an amino acid, a protein or a peptide.

3. The method of claim 1 wherein the artificial chromosome is a satellite artificial chromosome.

4. The method of claim 3 wherein the satellite artificial chromosome contains about 250 to about 400 megabases.

5. The method of claim 3 wherein the satellite artificial chromosome contains about 150 to about 200 megabases.

6. The method of claim 3 wherein the satellite artificial chromosome contains about 90 to about 120 megabases.

7. The method of claim 3 wherein the satellite artificial chromosome contains about 60 to about 100 megabases.

8. The method of claim 3 wherein the artificial chromosome is a megachromosome.

9. The method of claim 3 wherein the satellite artificial chromosome contains about 7.5 to about 60 megabases.

10. The method of claim 3 wherein the satellite artificial chromosome contains about 30 to about 50 megabases.

11. The method of claim 3 wherein the satellite artificial chromosome contains about 10 to about 15 megabases.

12. The method of claim 3 wherein the satellite artificial chromosome contains about 15 to about 50 megabases.

13. The method of claim 3, wherein the satellite artificial chromosome is produced by a method comprising:
introducing one or more DNA fragments into a cell, wherein the DNA fragment or fragments comprise a selectable marker;
growing the cell under selective conditions to produce cells that have incorporated the DNA fragment or fragments into their genomic DNA; and
selecting a cell that comprises a satellite artificial chromosome.

14. The method of claim 1, wherein the product is selected from the group consisting of growth factors, antibodies, transcription factors, tumor suppressor proteins, enzymes, heat shock proteins, receptors, cytokines, proteases and hormones.

15. The method of claim 1, wherein the artificial chromosome is a minichromosome.

16. The method of claim 15, wherein the minichromosome is a λ neo-chromosome.

17. The method of claim 15, wherein the minichromosome comprises a neocentromere.

18. The method of claim 15, wherein the minichromosome is produced by a method comprising:

introducing one or more DNA fragments into a cell, wherein the DNA fragment or fragments comprise a selectable marker;

growing the cell under selective conditions to produce cells that have incorporated the DNA fragment or fragments into their genomic DNA;

selecting a cell that comprises a minichromosome.

19. The method of claim 1, wherein the heterologous genes are expressed in the cell.

20. The method of claim 19, wherein the heterologous genes are expressed in the cell in the absence of selective conditions.

21. The method of claim 1, wherein the product is produced by expression of a series of genes that encode a metabolic pathway; and the satellite artificial chromosome comprises each of these genes.

22. A method for producing a gene product or products comprising:

introducing satellite artificial chromosomes comprising DNA encoding the gene product or products into cells; and culturing the cells under conditions whereby the gene product or products are expressed.

23. The method of claim 22, wherein the satellite artificial chromosomes are produced by a method comprising:

introducing one or more DNA fragments into a cell, wherein the DNA fragment or fragments comprise a selectable marker;

growing the cell under selective conditions to produce cells that have incorporated the DNA fragment or fragments into their genomic DNA;

selecting a cell that comprises a satellite artificial chromosome;

introducing DNA that comprises DNA encoding the gene product or products into the selected cell that comprises a satellite artificial chromosome; and selecting a cell that comprises a satellite artificial chromosome that comprises the DNA encoding the gene product or products.

24. The method of claim 22, wherein the satellite artificial chromosomes are purified prior to being introduced into the cells.

25. The method of claim 22, wherein the gene product or products are selected from the group consisting of growth factors, antibodies, transcription factors, tumor suppressor proteins, enzymes, heat shock proteins, receptors, cytokines, proteases and hormones.

26. The method of claim 22, wherein the gene product or products are therapeutically effective products.

27. The method of claim 22 wherein the satellite artificial chromosome contains about 250 to about 400 megabases.

28. The method of claim 22 wherein the satellite artificial chromosome contains about 150 to about 200 megabases.

29. The method of claim 22 wherein the satellite artificial chromosome contains about 90 to about 120 megabases.

30. The method of claim 22 wherein the satellite artificial chromosome contains about 60 to about 100 megabases.

31. The method of claim 22 wherein the artificial chromosome is a megachromosome.

32. The method of claim 22 wherein the satellite artificial chromosome contains about 7.5 to about 60 megabases.

33. The method of claim 22 wherein the satellite artificial chromosome contains about 30 to about 50 megabases.

34. The method of claim 22 wherein the satellite artificial chromosome contains about 10 to about 15 megabases.

35. The method of claim 22 wherein the satellite artificial chromosome contains about 15 to about 50 megabases.

36. A method for producing a gene product, comprising introducing a satellite artificial chromosome into a cell; and culturing the cell under conditions whereby the gene product is expressed, wherein the satellite artificial chromosome comprises the gene.

37. A method for producing a gene product or products, comprising culturing a cell containing a satellite artificial chromosome comprising DNA encoding the gene product or products under conditions whereby the gene product or products are expressed, wherein the satellite artificial chromosome is produced by a method, comprising:

introducing one or more DNA fragments into a cell, wherein the DNA fragment or fragments cornprise a selectable marker;

growing the cell under selective conditions to produce cells that have incorporated the DNA fragment or fragments into their genomic DNA; and selecting a cell that comprises a satellite artificial chromosome.

* * * * *

SEQUENCE LISTING (1) GENERAL INFORMATION:

(iii) NUMBER OF SEQUENCES: 15

(2) INFORMATION FOR SEQ ID NO:1:

(i) SEQUENCE CHARACTERISTICS:
        (A) LENGTH: 1293 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(ix) FEATURE:

(xi) SEQUENCE DESCRIPTION: SEQ ID NO:1:

```
GAATTCATCA TTTTTCANGT CCTCAAGTGG ATGTTTCTCA TTTNCCATGA TTTTAAGTTT      60

TCTCGCCATA TTCCTGGTCC TACAGTGTGC ATTTCTCCAT TTTNCACGTT TTNCAGTGAT     120

TTCGTCATTT TCAAGTCCTC AAGTGGATGT TTCTCATTTN CCATGAATTT CAGTTTTCTN     180

GCCATATTCC ACGTCCTACA GNGGACATTT CTAAATTTNC CACCTTTTTC AGTTTTCCTC     240

GCCATATTTC ACGTCCTAAA ATGTGTATTT CTCGTTTNCC GTGATTTTCA GTTTTCTCGC     300

CAGATTCCAG GTCCTATAAT GTGCATTTCT CATTTNNCAC GTTTTTCAGT GATTTCGTCA     360

TTTTTTCAAG TCGGCAAGTG GATGTTTCTC ATTTNCCATG ATTTNCAGTT TTCTTGNAAT     420

ATTCCATGTC CTACAATGAT CATTTTTAAT TTTCCACCTT TTCATTTTTC CACGCCATAT     480

TTCATGTCCT AAAGTGTATA TTTCTCCTTT TCCGCGATTT TCAGTTTTCT CGCCATATTC     540

CAGGTCCTAC AGTGTGCATT CCTCATTTTT CACCTTTTTC ACTGATTTCG TCATTTTTCA     600

AGTCGTCAAC TGGATCTTTC TAATTTTCCA TGATTTTCAG TTATCTTGTC ATATTCCATG     660

TCCTACAGTG GACATTTCTA AATTTTCCAA CTTTTTCAAT TTTTCTCGAC ATATTTGACG     720

TGCTAAAGTG TGTATTTCTT ATTTTCCGTG ATTTTCAGTT TTCTCGCCAT ATTCCAGGTC     780

CTAATAGTGT GCATTTCTCA TTTTTCACGT TTTTCAGTGA TTTCGTCATT TTTTCCAGTT     840

GTCAAGGGGA TGTTTCTCAT TTTCCATGAG TGTCAGTTTT CTTGCTATAT TCCATGTCCT     900

ACAGTGACAT TTCTAAATAT TATACCTTTT TCAGTTTTTC TCACCATATT TCACGTCCTA     960

AAGTATATAT TTCTCATTTT CCCTGATTTT CAGTTTCCTT GCCATATTCC AGGTCCTACA    1020
```

```
GTGTGCATTT CTCATTTTTC ACGTTTTTCA GTAATTTCTT CATTTTTTAA GCCCTCAAAT   1080

GGATGTTTCT CATTTTCCAT GATTTTCAGT TTTCTTGCCA TATACCATGT CCTACAGTGG   1140

ACATTTCTAA ATTATCCACC TTTTTCAGTT TTTCATCGGC ACATTTCACG TCCTAAAGTG   1200

TGTATTTCTA ATTTTCAGTG ATTTTCAGTT TTCTCGCCAT ATTCCAGGAC CTACAGTGTG   1260

CATTTCTCAT TTTTCACGTT TTTCAGTGAA TTC                                1293
```

(2) INFORMATION FOR SEQ ID NO:2:

(i) SEQUENCE CHARACTERISTICS:
        (A) LENGTH: 1044 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(ix) FEATURE:

(xi) SEQUENCE DESCRIPTION: SEQ ID NO:2:

```
AGGCCTATGG TGAAAAAGGA AATATCTTCC CCTGAAAACT AGACAGAAGG ATTCTCAGAA     60

TCTTATTTGT GATGTGCGCC CCTCAACTAA CAGTGTTGAA GCTTTCTTTT GATAGAGCAG    120

TTTTGAAACA CTCTTTTTGT AAAATCTGCA AGAGGATATT TGGATAGCTT TGAGGATTTC    180

CGTTGGAAAC GGGATTGTCT TCATATAAAC CCTAGACAGA AGCATTCTCA GAAGCTTCAT    240

TGGGATGTTT CAGTTGAAGT CACAGTGTTG AACAGTCCCC TTTCATAGAG CAGGTTTGAA    300

ACACTCTTTT TTGTAGTATC TGGAAGTGGA CATTTGGAGC GATCTCAGGA CTGCGGTGAA    360

AAAGGAAATA TCTTCCAATA AAAGCTAGAT AGAGGCAATG TCAGAAACCT TTTTCATGAT    420

GTATCTACTC AGCTAACAGA GTTGAACCTT CCTTTGAGAG AGCAGTTTTG AAACACTCTT    480

TTTGTGGAAT CTGCAAGTGG ATATTTGTCT AGCTTTGAGG ATTTCGTTGG GAAACGGGAT    540

TACATATAAA AAGCAGACAG CAGCATTCCC AGAAACTTCT TTGTGATGTT TGCATTCAAG    600

TCACAGAGTT GAACATTCCC TTTCATAGAG CAGGTTTGAA ACACACTTTT TGATGTATCT    660

GGATGTGGAC ATTTGCAGCG CTTTCAGGCC TAAGGTGAAA AGGAAATATC TTCCCCTGAA    720

AACTAGACAG AAGCATTCTC AGAAACTTAT TTGTGATGTG CGCCCTCAAC TAACAGTGTT    780

GAAGCTTTCT TTTGATAGAG GCAGTTTTGA AACACTCTTT TGTGGAATCT GCAAGTGGAT    840

ATTTGTCTAG CTTTGAGGAT TTCTTTGGAA ACGGGATTAC ATATAAAAG CAGACAGCAG     900

CATTCCCAGA ATCTTGTTTG TGATGTTTGC ATTCAAGTCA CAGAGTTGAA CATTCCCTTT    960

CAGAGAGCAG GTTGAACAC TCTTTTTATA GTATCTGGAT GTGGACATTT GGAGCGCTTT    1020

CAGGGGGAT CCTCTAGAAT TCCT                                           1044
```

(2) INFORMATION FOR SEQ ID NO:3:

(i) SEQUENCE CHARACTERISTICS:
        (A) LENGTH: 2492 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(ix) FEATURE:

(xi) SEQUENCE DESCRIPTION: SEQ ID NO:3:

```
CTGCAGCTGG GGGTCTCCAA TCAGGCAGGG GCCCCTTACT ACTCAGATGG GGTGGCCGAG    60

TAGGGGAAGG GGGTGCAGGC TGCATGAGTG GACACAGCTG TAGGACTACC TGGGGGCTGT   120

GGATCTATGG GGGTGGGGAG AAGCCCAGTG ACAGTGCCTA GAAGAGACAA GGTGGCCTGA   180

GAGGGTCTGA GGAACATAGA GCTGGCCATG TTGGGGCCAG GTCTCAAGCA GGAAGTGAGG   240

AATGGGACAG GCTTGAGGAT ACTCTACTCA GTAGCCAGGA TAGCAAGGAG GGCTTGGGGT   300

TGCTATCCTG GGGTTCAACC CCCCAGGTTG AAGGCCCTGG GGGAGATGGT CCCAGGACAT   360

ATTACAATGG ACACAGGAGG TTGGGACACC TGGAGTCACC AAACAAAACC ATGCCAAGAG   420

AGACCATGAG TAGGGGTGTC CAGTCCAGCC CTCTGACTGA GCTGCATTGT TCAAATCCAA   480

AGGGCCCCTG CTGCCACCTA GTGGCTGATG GCATCCACAT GACCCTGGGC CACACGCGTT   540

TAGGGTCTCT GTGAAGACCA AGATCCTTGT TACATTGAAC GACTCCTAAA TGAGCAGAGA   600

TTTCCACCTA TTCGAAACAA TCACATAAAA TCCATCCTGG AAAAAGCCTG GGGGATGGCA   660

CTAAGGCTAG GGATAGGGTG GGATGAAGAT TATAGTTACA GTAAGGGGTT TAGGGTTAGG   720

GATCAACGTT GGTTAGGAGT TAGGGATACA GTAGGGTACC GGTAGGGTTA GGGGTTAGGG   780

TTAGGGGTTA GGGTTAGGGT TAGGGTTAGG GTTAGGGTTA GGGGTTAGGG GTTAGGGTTA   840

GGGTTAGGTT TTGGGGTGGC GTATTTTGGT CTTATACGCT GTGTTCCACT GGCAATGAAA   900

AGAGTTCTTG TTTTTCCTTC AGCAATTTGT CATTTTTAAA AGAGTTTAGC AATTCTAACA   960

GATATAGACC AGCTGTGCTA TCTCATTGTG GTTTTCAATT GTAACCACAT TGTGGTTTCA  1020

ATGTGTTTAC TTGCCATCTG TAGATCTTCT TTGCGTGAGG TGTCTGTTCA GATGTGTGTG  1080

CATTTCTTGN NTTTNGGCTG TTTAACTTAT TGTTTAGTTT TAATAATTTT TTATATATTT  1140

GAAGACAAAT CTTTCTCAGA TGTGTATTTG CAAATATTTC TTCAATATGA GGCTTGCTTT  1200

TGTCTCTAAC AAGGTCTCTT CAGAGATAAC TTAAATATAA GAAATCCACA CTGTCACTTC  1260

TTTTGTGTAT ATCTACCTTT TGTGTCATTT GTTAAAATTC ATTACCAAAC CCAAAGGCAG  1320

ATAGCTTTTC TTCTATTGTT TCTTCTAGAA ATTTGTATAG TTTTGCATTT TTAGTGTAAG  1380

GATGATTTTG AGTGATTATT TGTGTAAGTT GTAAAGTTTT CGTCTATATC CATATCATTT  1440

CTTATGGTTT CCAATTAATC GTTCCCTCAC TATTTTTGGG AAAGACACAG GATAGTGGGC  1500

TTTGTTAGAG TAGATAGGTA GCTAGACATG AACAGGAGGG GGCCTCCTGG AAAAGGGAAA  1560

GTCTGGGAAG GCTCACCTGG AGGACCACCA AAAATTCACA TATTAGTAGC ATCTCTAGTG  1620

CTGGAGTGGA TGGGCACTTG TCAATTGTGG GTAGGAGGGA AAAGAGGTCC TATGCAGAAA  1680

GAAACTCCCT AGAACTCCTC TGAAGATGCC CCAATCATTC ACTCTGCAAT AAAAATGTCA  1740

GAATATTGCT AGCTACATGC TGATAAGGNN AAAGGGGACA TTCTTAAGTG AAACCTGGCA  1800

CCATAAGTAC AGATTAGGGC AGAGAAGGAC ATTCAAAAGA GGCAGGCGCA GTAGGTACAA  1860

ACGTGATCGC TGTCAGTGTG CCTGGGATGG CGGGAAGGAG GCTGGTGCCA GAGTGGATTC  1920

GTATTGATCA CCACACATAT ACCTCAACCA ACAGTGAGGA GGTCCCACAA GCCTAAGTGG  1980

GGCAAGTTGG GGAGCTAAGG CAGTAGCAGG AAAACCAGAC AAAGAAAACA GGTGGAGACT  2040
```

```
TGAGACAGAG GCAGGAATGT GAAGAAATCC AAAATAAAAT TCCCTGCACA GGACTCTTAG    2100

GCTGTTTAAT GCATCGCTCA GTCCCACTCC TCCCTATTTT TCTACAATAA ACTCTTTACA    2160

CTGTGTTTCT TTTCAATGAA GTTATCTGCC ATCTTTGTAT TGCCTCTTGG TGAAAATGTT    2220

TCTTCCAAGT TAAACAAGAA CTGGGACATC AGCTCTCCCC AGTAATAGCT CCGTTTCAGT    2280

TTGAATTTAC AGAACTGATG GGCTTAATAA CTGGCGCTCT GACTTTAGTG GTGCAGGAGG    2340

CCGTCACACC GGGACCAAGA GTGCCCTGCC TAGTCCCCAT CTGCCCGCAG GTGGCGGCTG    2400

CCTCGACACT GACAGCAATA GGGTCCGGCA GTGTCCCCAG CTGCCAGCAG GGGGCGTACG    2460

ACGACTACAC TGTGAGCAAG AGGGCCCTGC AG                                  2492
```

(2) INFORMATION FOR SEQ ID NO:4:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(ix) FEATURE:

(xi) SEQUENCE DESCRIPTION: SEQ ID NO:4:

```
GGGGAATTCA TTGGGATGTT TCAGTTGA                                         28
```

(2) INFORMATION FOR SEQ ID NO:5:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(ix) FEATURE:

(xi) SEQUENCE DESCRIPTION: SEQ ID NO:5:

```
CGAAAGTCCC CCCTAGGAGA TCTTAAGGA                                        29
```

(2) INFORMATION FOR SEQ ID NO:6:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (ii) MOLECULE TYPE: RNA (iii) HYPOTHETICAL: NO (iv) ANTI-SENSE: NO (v) FRAGMENT TYPE:

(vi) ORIGINAL SOURCE:

(ix) FEATURE:

(xi) SEQUENCE DESCRIPTION: SEQ ID NO:6:

CCGCTTAATA CTCTGATGAG TCCGTGAGGA CGAAACGCTC TCGCACC                47

(2) INFORMATION FOR SEQ ID NO:7:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(ix) FEATURE:

(xi) SEQUENCE DESCRIPTION: SEQ ID NO:7:

CGATTTAAAT TAATTAAGCC CGGGC                                        25

(2) INFORMATION FOR SEQ ID NO:8:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(ix) FEATURE:

(xi) SEQUENCE DESCRIPTION: SEQ ID NO:8:

TAAATTTAAT TAATTCGGGC CCGTCGA                                      27

(2) INFORMATION FOR SEQ ID NO:9:

(i) SEQUENCE CHARACTERISTICS:
            (A) LENGTH: 69 base pairs
            (B) TYPE: nucleic acid
            (C) STRANDEDNESS: single
            (D) TOPOLOGY: linear (ii) MOLECULE TYPE: Genomic DNA (ix) FEATURE:
            (D) OTHER INFORMATION: IL-2 signal sequence (xi) SEQUENCE DESCRIPTION: SEQ ID NO:9:

ATG TAC AGG ATG CAA CTC CTG TCT TGC ATT GCA CTA AGT CTT GCA CTT    48
Met Tyr Arg Met Gln Leu Leu Ser Cys Ile Ala Leu Ser Leu Ala Leu

```
GTC ACA AAC AGT GCA CCT ACT                                              69
Val Thr Asn Ser Ala Pro Thr
```

(2) INFORMATION FOR SEQ ID NO:10:

(i) SEQUENCE CHARACTERISTICS:
        (A) LENGTH: 945 base pairs
        (B) TYPE: nucleic acid
        (C) STRANDEDNESS: single
        (D) TOPOLOGY: linear (ii) MOLECULE TYPE: cDNA (vi) ORIGINAL SOURCE:

(ix) FEATURE:
        (A) NAME/KEY: Coding Sequence
        (B) LOCATION: 1...942
        (D) OTHER INFORMATION: Renilla Reinformis Luciferase (x) PUBLICATION INFORMATION:
        PATENT NO.: 5,418,155

(xi) SEQUENCE DESCRIPTION: SEQ ID NO:10:

```
AGC TTA AAG ATG ACT TCG AAA GTT TAT GAT CCA GAA CAA AGG AAA CGG        48
Ser Leu Lys Met Thr Ser Lys Val Tyr Asp Pro Glu Gln Arg Lys Arg
 1               5                  10                  15

ATG ATA ACT GGT CCG CAG TGG TGG GCC AGA TGT AAA CAA ATG AAT GTT        96
Met Ile Thr Gly Pro Gln Trp Trp Ala Arg Cys Lys Gln Met Asn Val
                20                  25                  30

CTT GAT TCA TTT ATT AAT TAT TAT GAT TCA GAA AAA CAT GCA GAA AAT       144
Leu Asp Ser Phe Ile Asn Tyr Tyr Asp Ser Glu Lys His Ala Glu Asn
            35                  40                  45

GCT GTT ATT TTT TTA CAT GGT AAC GCG GCC TCT TCT TAT TTA TGG CGA       192
Ala Val Ile Phe Leu His Gly Asn Ala Ala Ser Ser Tyr Leu Trp Arg
 50                  55                  60

CAT GTT GTG CCA CAT ATT GAG CCA GTA GCG CGG TGT ATT ATA CCA GAT       240
His Val Val Pro His Ile Glu Pro Val Ala Arg Cys Ile Ile Pro Asp
 65                  70                  75                  80

CTT ATT GGT ATG GGC AAA TCA GGC AAA TCT GGT AAT GGT TCT TAT AGG       288
Leu Ile Gly Met Gly Lys Ser Gly Lys Ser Gly Asn Gly Ser Tyr Arg
                85                  90                  95

TTA CTT GAT CAT TAC AAA TAT CTT ACT GCA TGG TTG AAC TTC TTA ATT       336
Leu Leu Asp His Tyr Lys Tyr Leu Thr Ala Trp Leu Asn Phe Leu Ile
            100                 105                 110

TAC CAA AGA AGA TCA TTT TTT GTC GGC CAT GAT TGG GGT GCT TGT TTG       384
Tyr Gln Arg Arg Ser Phe Phe Val Gly His Asp Trp Gly Ala Cys Leu
        115                 120                 125

GCA TTT CAT TAT AGC TAT GAG CAT CAA GAT AAG ATC AAA GCA ATA GTT       432
Ala Phe His Tyr Ser Tyr Glu His Gln Asp Lys Ile Lys Ala Ile Val
130                 135                 140

CAC GCT GAA AGT GTA GTA GAT GTG ATT GAA TCA TGG GAT GAA TGG CCT       480
His Ala Glu Ser Val Val Asp Val Ile Glu Ser Trp Asp Glu Trp Pro
145                 150                 155                 160

GAT ATT GAA GAA GAT ATT GCG TTG ATC AAA TCT GAA GAA GGA GAA AAA       528
Asp Ile Glu Glu Asp Ile Ala Leu Ile Lys Ser Glu Glu Gly Glu Lys
                165                 170                 175

ATG GTT TTG GAG AAT AAC TTC TTC GTG GAA ACC ATG TTG CCA TCA AAA       576
Met Val Leu Glu Asn Asn Phe Phe Val Glu Thr Met Leu Pro Ser Lys
            180                 185                 190

ATC ATG AGA AAG TTA GAA CCA GAA GAA TTT GCA GCA TAT CTT GAA CCA       624
Ile Met Arg Lys Leu Glu Pro Glu Glu Phe Ala Ala Tyr Leu Glu Pro
        195                 200                 205
```

```
TTC AAA GAG AAA GGT GAA GTT CGT CGT CCA ACA TTA TCA TGG CCT CGT       672
Phe Lys Glu Lys Gly Glu Val Arg Arg Pro Thr Leu Ser Trp Pro Arg
    210                 215                 220

GAA ATC CCG TTA GTA AAA GGT GGT AAA CCT GAC GTT GTA CAA ATT GTT       720
Glu Ile Pro Leu Val Lys Gly Gly Lys Pro Asp Val Val Gln Ile Val
225                 230                 235                 240

AGG AAT TAT AAT GCT TAT CTA CGT GCA AGT GAT GAT TTA CCA AAA ATG       768
Arg Asn Tyr Asn Ala Tyr Leu Arg Ala Ser Asp Asp Leu Pro Lys Met
                245                 250                 255

TTT ATT GAA TCG GAT CCA GGA TTC TTT TCC AAT GCT ATT GTT GAA GGC       816
Phe Ile Glu Ser Asp Pro Gly Phe Phe Ser Asn Ala Ile Val Glu Gly
            260                 265                 270

GCC AAG AAG TTT CCT AAT ACT GAA TTT GTC AAA GTA AAA GGT CTT CAT       864
Ala Lys Lys Phe Pro Asn Thr Glu Phe Val Lys Val Lys Gly Leu His
        275                 280                 285

TTT TCG CAA GAA GAT GCA CCT GAT GAA ATG GGA AAA TAT ATC AAA TCG       912
Phe Ser Gln Glu Asp Ala Pro Asp Glu Met Gly Lys Tyr Ile Lys Ser
    290                 295                 300

TTC GTT GAG CGA GTT CTC AAA AAT GAA CAA TAA                           945
Phe Val Glu Arg Val Leu Lys Asn Glu Gln
305                 310
```

(2) INFORMATION FOR SEQ ID NO:11:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(ix) FEATURE:

(xi) SEQUENCE DESCRIPTION: SEQ ID NO:11:

TTTGAATTC A TGTACAGGAT GCAACTCCTG            30

(2) INFORMATION FOR SEQ ID NO:12:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(ix) FEATURE:

(xi) SEQUENCE DESCRIPTION: SEQ ID NO:12:

TTTGAATTCA GTAGGTGCAC TGTTTGTCAC            30

(2) INFORMATION FOR SEQ ID NO:13:

(i) SEQUENCE CHARACTERISTICS:
    (A) LENGTH: 1434 base pairs
    (B) TYPE: nucleic acid
    (C) STRANDEDNESS: single
    (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:13:

```
CCTCCACGCA CGTTGTGATA TGTAGATGAT AATCATTATC AGAGCAGCGT TGGGGGATAA      60
TGTCGACATT TCCACTCCCA ATGACGGTGA TGTATAATGC TCAAGTATTC TCCTGCTTTT     120
TTACCACTAA CTAGGAACTG GGTTTGGCCT TAATTCAGAC AGCCTTGGCT CTGTCTGGAC     180
AGGTCCAGAC GACTGACACC ATTAACACTT TGTCAGCCTC AGTGACTACA GTCATAGATG     240
AACAGGCCTC AGCTAATGTC AAGATACAGA GAGGTCTCAT GCTGGTTAAT CAACTCATAG     300
ATCTTGTCCA GATACAACTA GATGTATTAT GACAAATAAC TCAGCAGGGA TGTGAACAAA     360
AGTTTCCGGG ATTGTGTGTT ATTTCCATTC AGTATGTTAA ATTTACTAGG ACAGCTAATT     420
TGTCAAAAAG TCTTTTTCAG TATATGTTAC AGAATTGGAT GGCTGAATTT GAACAGATCC     480
TTCGGGAATT GAGACTTCAG GTCAACTCCA CGCGCTTGGA CCTGTCGCTG ACCAAAGGAT     540
TACCCAATTG GATCTCCTCA GCATTTTCTT TCTTTAAAAA ATGGGTGGGA TTAATATTAT     600
TTGGAGATAC ACTTTGCTGT GGATTAGTGT TGCTTCTTTG ATTGGTCTGT AAGCTTAAGG     660
CCCAAACTAG GAGAGACAAG GTGGTTATTG CCCAGGCGCT TGCAGGACTA GAACATGGAG     720
CTTCCCCTGA TATATGGTTA TCTATGCTTA GGCAATAGGT CGCTGGCCAC TCAGCTCTTA     780
TATCCCACGA GGCTAGTCTC ATTGTACGGG ATAGAGTGAG TGTGCTTCAG CAGCCCGAGA     840
GAGTTGCAAG GCTAAGCACT GCAATGGAAA GGCTCTGCGG CATATATGTG CCTATTCTAG     900
GGGGACATGT CATCTTTCAT GAAGGTTCAG TGTCCTAGTT CCCTTCCCCC AGGCAAAACG     960
ACACGGGAGC AGGTCAGGGT TGCTCTGGGT AAAAGCCTGT GAGCCTGGGA GCTAATCCTG    1020
TACATGGCTC CTTTACCTAC ACACTGGGGA TTTGACCTCT ATCTCCACTC TCATTAATAT    1080
GGGTGGCCTA TTTGCTCTTA TTAAAAGGAA AGGGGGAGAT GTTGGGAGCC GCGCCCACAT    1140
TCGCCGTTAC AAGATGGCGC TGACAGCTGT GTTCTAAGTG GTAAACAAAT AATCTGCGCA    1200
TGTGCCGAGG GTGGTTCTTC ACTCCATGTG CTCTGCCTTC CCCGTGACGT CAACTCGGCC    1260
GATGGGCTGC AGCCAATCAG GGAGTGACAC GTCCTAGGCG AAGGAGAATT CTCCTTAATA    1320
GGGACGGGGT TTCGTTCTCT CTCTCTCTCT TGCTTCTCTC TCTTGCTTTT TCGCTCTCTT    1380
GCTTCCCGTA AAGTGATAAT GATTATCATC TACATATCAC AACGTGCGTG GAGG          1434
```

(2) INFORMATION FOR SEQ ID NO:14:

(i) SEQUENCE CHARACTERISTICS:
    (A) LENGTH: 1400 base pairs
    (B) TYPE: nucleic acid
    (C) STRANDEDNESS: single
    (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:14:

| | | | | | |
|---|---|---|---|---|---|
| CCTCCACGCA | CGTTGTGATA | TGTAGATGAT | AATCATTATC | AGAGCAGCGT | TGGGGGATAA | 60 |
| TGTCGACATT | TCCACTCCCA | ATGACGGTGA | TGTATAATGC | TCAAGTATTC | TCCTGCTTTT | 120 |
| TTACCACTAA | CTAGGAACTG | GGTTTGGCCT | TAATTCAGAC | AGCCTTGGCT | CTGTCTGGAC | 180 |
| AGGTCCAGAT | ACAACTAGAT | GTATTATGAC | AAATAACTCA | GCAGGGATGT | GAACAAAAGT | 240 |
| TTCCGGGATT | GCGTGTTATT | TCCATCCAGT | ATGTTAAATT | TACTAGGGCA | GCTAATTTGT | 300 |
| CAAAAAGTCT | TTTCCAGTAT | ATGTTACAGA | ATTGGATGGC | TGAATTTGAA | CAGATCCTTC | 360 |
| GGGAATTGAG | ACTTCAGGTC | AACTCCACGC | GCTTGGACCT | GTCCCTGACC | AAAGGATTAC | 420 |
| CCAATTGGAT | CTCCTCAGCA | TTTTCTTTCT | TTAAAAAATG | GGTGGGATTA | ATATTATTTG | 480 |
| GAGATACACT | TTGCTGTGGA | TTAGTGTTGC | TTCTTTGATT | GGTCTGTAAG | CTTAAGGCCC | 540 |
| AAACTAGGAG | AGACAAGGTG | GTTATTGCCC | AGGCGCTTGC | AGGACTAGAA | CATGGAGCTT | 600 |
| CCCCTGATAT | ATCTATGCTT | AGGCAATAGG | TCGCTGGCCA | CTCAGCTCTT | ATATCCCATG | 660 |
| AGGCTAGTCT | CATTGCACGG | GATAGAGTGA | GTGTGCTTCA | GCAGCCCGAG | AGAGTTGCAC | 720 |
| GGCTAAGCAC | TGCAATGGAA | AGGCTCTGCG | GCATATATGA | GCCTATTCTA | GGGAGACATG | 780 |
| TCATCTTTCA | AGAAGGTTGA | GTGTCCAAGT | GTCCTTCCTC | CAGGCAAAAC | GACACGGGAG | 840 |
| CAGGTCAGGG | TTGCTCTGGG | TAAAAGCCTG | TGAGCCTAAG | AGCTAATCCT | GTACATGGCT | 900 |
| CCTTTACCTA | CACACTGGGG | ATTTGACCTC | TATCTCCACT | CTCATTAATA | TGGGTGGCCT | 960 |
| ATTTGCTCTT | ATTAAAAGGA | AAGGGGAGA | TGTTGGGAGC | CGCGCCCACA | TTCGCCGTTA | 1020 |
| CAAGATGGCG | CTGACAGCTG | TGTTCTAAGT | GGTAAACAAA | TAATCTGCGC | ATGCGCCGAG | 1080 |
| GGTGGTTCTT | CACTCCATGT | GCTCTGCCTT | CCCCGTGACG | TCAACTCGGC | CGATGGGCTG | 1140 |
| CAGTCAATCA | GGGAGTGACA | CGTCCTAGGC | GAAGGAAAAT | TCTCCTTAAT | AGGGACGGGG | 1200 |
| TTTCGTTTTC | TCTCTCTCTT | GCTTCGCTCT | CTCTTGCTTC | TTGCTCTCTT | TTCCTGAAGA | 1260 |
| TGTAAGAATA | AAGCTTTGCC | GCAGAAGATT | CTGGTCTGTG | GTGTTCTTCC | TGGCCGGTCG | 1320 |
| TGAGAACGCG | TCTAATAACA | ATTGGTGCCG | AAACCCGGGT | GATAATGATT | ATCATCTACA | 1380 |
| TATCACAACG | TGCGTGGAGG | | | | | 1400 |

(2) INFORMATION FOR SEQ ID NO:15:

(i) SEQUENCE CHARACTERISTICS:
        (A) LENGTH: 1369 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:15:

| | | | | | |
|---|---|---|---|---|---|
| CCTCCACGCA | CGTTGTGATA | TGTAGATGAT | AATCATTATC | ACTTTACGGG | TCCTTTCACT | 60 |
| ACAACTGCCA | CGAGGCCCCG | TGCTCTGGTA | ATAGATCTTT | GCTGAAAAGG | CACACACATG | 120 |

```
ACACATTACT CAAGGTGGGC TCATCTGAGC TGCAGATTCA GCTTAATATG AATCTTGCCA    180

ATTGTGTGAA ATCATAAATC TTCAAAGTGA CACTCATTGC CAGACACAGG TGCCCACCTT    240

TGGCATAATA AACAAACACA AATTATCTAT TATATAAAGG GTGTTAGAAG ATGCTTTAGA    300

ATACAAATAA ATCATGGTAG ATAACAGTAA GTTGAGAGCT TAAATTTAAT AAAGTGATAT    360

ACCTAATAAA AATTAAATTA AGAAGGTGTG AATATACTAC AGTAGGTAAA TTATTTCATT    420

AATTTATTTT CTTTCTTAAT CCTTTATAAT GTTTTCTGCT ATTGTCAATT GCACATCCAT    480

ATGTTCAATT CTTCACTGTA ATGAAGAAAT GTAGTAAATA TACTTTCCGA ACAAGTTGTA    540

TCAAATATGT TACACTTGAT TCCGTGTGTT ACTTATCATT TTATTATTAT ATTGATTGCA    600

TTCCTTCGTT ACTTGATATT ATTACAAGGT ACATATTTAT TCTCTCAGAT CTTCATTATA    660

CTCTAACCAT TTTATAACAT ACTTTATTTA TTCATTTCTT ATGTGTGCTG TGAGGCACAA    720

ATGCCAGAGA GAACTTGAGC AGATAAGAGG ACAAATTGCA AGAGTCAGTT ACCTCCTGCT    780

GTTCCTTGGA AACTCAGGAT CAAATTCAGG TTGTCAGGCT TGGCAGCATG CACTTTTTAC    840

CAGTGCCTCC ATCTTGCTAG CCCTGAACAT CAAGCTTTGC AGACAGACAG GCTACACTAA    900

GTGAACTGGT CATTCACAGC ATGCATGGTG ATTTATTGTT ACTTTCTATT CCATGCCTTT    960

ACTATTTCTA CTAGGTGCTA GCTAGTACTG TATTTCGAGA TAGAAGTTAC TGAAAGAAAA   1020

TTACATTGTT TTCTATAGAT CCTTGATACT CTTTCAGCAG ATATAGAGTT TTAATCAGGT   1080

CCTAGACCCT TTCTTCACTC TTATTAAATA CTAAGTACAA ATTAAGTTTA TCCAAAACAG   1140

TACGGATGTT GATTTTGTGC AGTTCTACTA TGATAATAGT CTAGCTTCAT AAATCTGACA   1200

CACTTATTGG GAATGTTTTT GTTAATAAAA GATTCAGGTG TTACTCTAGG TCAAGAGAAT   1260

ATTAAACATC AGTCCCAAAT TACAAACTTC AATAAAAGAT TTGACTCTCC AGTGGTGGCA   1320

ATATAAAGTG ATAATGATTA TCATCTACAT ATCACAACGT GCGTGGAGG               1369
```